US009675923B2

(12) United States Patent
Long et al.

(10) Patent No.: US 9,675,923 B2
(45) Date of Patent: Jun. 13, 2017

(54) GAS SEPARATIONS WITH REDOX-ACTIVE METAL-ORGANIC FRAMEWORKS

(75) Inventors: Jeffrey R. Long, Oakland, CA (US);
Eric D. Bloch, Berkeley, CA (US);
Leslie Murray, Gainesville, FL (US)

(73) Assignee: The Regents of the University of California, Oakland, CA (US)

( * ) Notice: Subject to any disclaimer, the term of this patent is extended or adjusted under 35 U.S.C. 154(b) by 289 days.

(21) Appl. No.: 13/593,914

(22) Filed: Aug. 24, 2012

(65) Prior Publication Data
US 2013/0053585 A1 Feb. 28, 2013

Related U.S. Application Data

(60) Provisional application No. 61/527,331, filed on Aug. 25, 2011.

(51) Int. Cl.
| | | |
|---|---|---|
| C07C 11/04 | (2006.01) |
| C07C 11/06 | (2006.01) |
| C07C 29/50 | (2006.01) |
| C07C 7/12 | (2006.01) |
| C07C 45/32 | (2006.01) |
| C07C 9/04 | (2006.01) |
| C07D 301/04 | (2006.01) |
| C01B 21/22 | (2006.01) |
| C01B 21/24 | (2006.01) |
| B01D 53/02 | (2006.01) |
| C01B 13/02 | (2006.01) |
| C07C 45/35 | (2006.01) |
| C10L 3/10 | (2006.01) |
| B01J 31/16 | (2006.01) |
| B01J 31/22 | (2006.01) |

(52) U.S. Cl.
CPC ......... *B01D 53/02* (2013.01); *B01J 31/1691* (2013.01); *B01J 31/2239* (2013.01); *C01B 13/0262* (2013.01); *C01B 21/22* (2013.01); *C01B 21/24* (2013.01); *C07C 7/12* (2013.01); *C07C 29/50* (2013.01); *C07C 45/32* (2013.01); *C07C 45/35* (2013.01); *C07D 301/04* (2013.01); *C10L 3/101* (2013.01); *B01D 2253/204* (2013.01); *B01D 2256/12* (2013.01); *B01D 2256/24* (2013.01); *B01D 2257/102* (2013.01); *B01D 2257/404* (2013.01); *B01D 2257/7022* (2013.01); *B01J 2231/70* (2013.01); *B01J 2531/842* (2013.01); *Y02C 20/10* (2013.01); *Y02P 20/153* (2015.11); *Y02P 20/51* (2015.11)

(58) Field of Classification Search
CPC ......... C07C 11/04; C07C 11/06; C07C 29/50; C07C 45/32; C07D 301/04
See application file for complete search history.

(56) References Cited

U.S. PATENT DOCUMENTS

| 8,425,659 B2 * | 4/2013 | Matzger ................ B01D 53/02 |
| | | 95/139 |
| 2010/0258004 A1 | 10/2010 | Matzger et al. |
| 2011/0052650 A1 * | 3/2011 | Morris et al. ................. 424/401 |
| 2011/0172412 A1 * | 7/2011 | Serre et al. ................... 540/145 |

FOREIGN PATENT DOCUMENTS

WO  WO-2009/073739   6/2009

OTHER PUBLICATIONS

Yazaydin et al., J. Am. Chem. Soc., 2009, 131, 18198-18199.*
Ahmad, S. et al. (1988). "Raman Spectroscopic Evidence for Side-On Binding of Peroxide Ion to $Fe^{III}$(edta)," *Inorganic Chemistry* 27(13): 2230-2233.
Annaraj, J. et al. (2009). "Structural Characterization and Remarkable Axial Ligand Effect on the Nucleophilic Reactivity of a Nonheme Manganese (III)-Peroxo Complex," *Angewandte Chemie* 48: 4150-4153.
Bae, Y. et al. (Apr. 19, 2010). "Separation of gas mixtures using Co(II) carborane-based porous coordination polymers," *Chemical Communications* 46: 3478-3480.
Bhattacharjee, S. et al. (2010). "Solvothermal Synthesis of Fe-MOF-74 and Its Catalytic Properties in Phenol Hydroxylation," *Journal of Nanoscience and Nanotechnology* 10(1): 135-141.
Bloch, E. et al. (Sep. 17, 2010). "Metal Insertion in a Microporous Metal-Organic Framework Lined with 2,2'-Bipyridine," *Journal of the American Chemical Society* 132(41): 14382-14384.
Britt, D. et al. (Aug. 19, 2008). "Metal-organic frameworks with high capacity and selectivity for harmful gases," *Proceedings of the National Academy of Sciences* 105(33): 11623-11627.
Britt, D. et al. (Dec. 8, 2009). "Highly efficient separation of carbon dioxide by a metal-organic framework replete with open metal sites," *Proceedings of the National Academy of Sciences* 106(49): 20637-20640.
Caskey, S. et al. (Jul. 29, 2008). "Dramatic Tuning of Carbon Dioxide Uptake via Metal Substitution in a Coordination Polymer with Cylindrical Pores," *Journal of the American Chemical Society* 130(33): 10870-10871.
Chavan, S. et al. (Jul. 21, 2010). "Functionalization of UiO-66 Metal-Organic Framework and Highly Cross-Linked Polystyrene with Cr(CO)$_3$: In Situ Formation, Stability, and Photoreactivity," *Chemistry of Materials* 22(6): 4602-4611.
Chen, B. et al. (Aug. 2010). "Metal-Organic Frameworks with Functional Pores for Recognition of Small Molecules," *Accounts of Chemical Research* 43(8): 1115-1124.
Descamps, C. et al. (2008). "Efficiency of an Integrated Gasification Combined Cycle (IGCC) power plant including $CO_2$ removal," *Energy* 33: 874-881.

(Continued)

*Primary Examiner* — Sun Jae Yoo
(74) *Attorney, Agent, or Firm* — Morrison & Foerster LLP

(57) ABSTRACT

$Fe_2$(dobdc) has a metal-organic framework with a high density of coordinatively-unsaturated $Fe^{II}$ centers lining the pore surface. It can be effectively used to separate $O_2$ from $N_2$ and in a number of additional separation applications based on selective, reversible electron transfer reactions. In addition to being an effective $O_2$ separation material, it can be used for many other processes, including paraffin/olefin separation, nitric oxide/nitrous oxide separation, acetylene storage, and as an oxidation catalyst.

9 Claims, 41 Drawing Sheets

(56) References Cited

OTHER PUBLICATIONS

Dietzel, P. et al. (2005). "An In Situ High-Temperature Single-Crystal Investigation of a Dehydrated Metal-Organic Framework Compound and Field-Induced Magnetization of One-Dimensional Metal-Oxygen Chains," *Angewandte Chemie* 44: 6354-6358.

Dietzel, P. et al. (Jan. 20, 2006). "Hydrogen adsorption in a nickel based coordination polymer with open metal sites in the cylindrical cavities of the desolvated framework," *Chemical Communications* 959-961.

Dietzel, P. et al. (2008). "Base-Induced Formation of Two Magnesium Metal-Organic Framework Compounds with a Bifunctional Tetratopic Ligand," *European Journal of Inorganic Chemistry* 3624-3632.

Dietzel, P. et al. (Jan. 18, 2008). "Structural Changes and Coordinatively Unsaturated Metal Atoms on Dehydration of Honeycomb Analogous Microporous Metal-Organic Frameworks," *Chemistry-A European Journal* 14: 2389-2397.

Dietzel, P. et al. (May 28, 2010). "Interaction of hydrogen with accessible metal sites in the metal-organic frameworks $M_2$(dhtp) (CPO-27-M; M=Ni, Co, Mg)," *Chemical Communications* 46: 4962-4964.

Doonan, C. et al. (Jun. 17, 2009). "Isoreticular Metalation of Metal-Organic Frameworks," *Journal of the American Chemical Society* 131(27): 9492-9493.

Eddaoudi, M. et al. (Jan. 18, 2002). "Systematic Design of Pore Size and Functionality in Isoreticular MOFs and Their Application in Methane Storage," *Science* 295: 469-472.

Egan, J. et al. (1990). "Crystal Structure of a Side-On Superoxo Complex of Cobalt and Hydrogen Abstraction by a Reactive Terminal Oxo Ligand," *Journal of the American Chemical Society* 112: 2445-2446.

Feig, A. et al. (1994). "Reactions of Non-Heme Iron (II) Centers with Dioxygen in Biology and Chemistry," *Chemical Reviews* 94(3): 759-805.

Férey, G. (2008). "Hybrid porous solids: past, present, future," *Chemical Society Reviews* 37: 191-214.

Furukawa, H. et al. (May 10, 2007). "Independent verification of the saturation hydrogen uptake in MOF-177 and establishment of a benchmark for hydrogen adsorption in metal-organic frameworks," *Journal of Materials Chemistry* 17: 3197-3204.

Hadjipaschalis, I. et al. (2009). "Assessment of oxyfuel power generation technologies," *Renewable and Sustainable Energy Reviews* 13: 2637-2644.

Halder, G. et al. (Nov. 19, 2008). "Elucidating the Mechanism of a Two-Step Spin Transition in a Nanoporous Metal-Organic Framework," *Journal of the American Chemical Society* 130(51): 17552-17562.

Hayashi, H. et al. (Jul. 2007). "Zeolite A imidazolate frameworks," *Nature Materials* 6: 501-506.

Homer, O. et al. (Jun. 18, 2004). "Mössbauer Characterization of an Unusual High-Spin Side-On Peroxo-$Fe^{3}+$ Species in the Active Site of Superoxide Reductase from *Desulfoarculus baarsii*. Density Functional Calculations on Related Models," *Biochemistry* 43(27): 8815-8825.

Ingleson, M. et al. (May 9, 2008). "Framework functionalisation triggers metal complex binding," *Chemical Communications* 2680-2682.

Jee, J. et al. (Jul. 10, 2001). "Air Separation by a Small-Scale Two-Bed Medical $O_2$ Pressure Swing Adsorption," *Industrial & Engineering Chemical Research* 40(16): 3647-3658.

Karlsson, A. et al. (Feb. 14, 2003). "Crystal Structure of Naphthalene Dioxygenase: Side-On Binding of Dioxygen to Iron," *Science* 229:1039-1042.

Kather, A. et al. (Jun. 4, 2009). "The oxycoal process with cryogenic oxygen supply," *Naturwissenschaften* 96: 993-1010.

Kitagawa, S. et al. (2004). "Functional Porous Coordination Polymers," *Angewandte Chemie* 43: 2334-2375.

Kovaleva, E et al. (Apr. 20, 2007). "Crystal Structures of $Fe^{2+}$Dioxygenase Superoxo, Alkylperoxo, and Bound Product Intermediates," *Science* 316: 453-457.

Kovaleva, E. et al. (Jun. 14, 2007). "Finding Intermediates in the $O_2$ Activation Pathways of Non-Heme Iron Oxygenases," *Accounts of Chemical Research* 40(7): 475-483.

Kramer, M. et al. (Apr. 12, 2006). "Synthesis and properties of the metal-organic framework $Mo_3(BTC)_2$ (TUDMOF-1)," *Journal of Materials Chemistry* 16: 2245-2248.

Krishna, R. et al. (Jun. 2, 2011). "Screening Metal-Organic Frameworks by Analysis of Transient Breakthrough of Gas Mixtures in a Fixed Bed Adsorber," *The Journal of Physical Chemistry* 115: 12941-12950.

Kumar, R. (1996). "Vacuum Swing Adsorption Process for Oxygen Production—A Historical Perspective," *Separation Science and Technology* 31(7): 877-893.

Lamberti, C. et al. (Nov. 1, 2010). "Probing the surfaces of heterogeneous catalysts by in situ IR spectroscopy," *Chemical Society Reviews* 39: 4951-5001.

Li, J. et al. (Mar. 26, 2009). "Selective gas adsorption and separation in metal-organic frameworks," *Chemical Society Reviews* 38: 1477-1504.

Li, Y. et al. (Nov. 22, 2007). "Gas Adsorption and Storage in Metal-Organic Framework MOF-177," *Langmuir* 23(26): 12937-12944.

Liss, K. et al. (2006). "Echidna—the new high-resolution power diffractometer being built at OPAL," *Physica B* 385-386: 1010-1012.

Liu, J. et al. (2009). "Spectroscopic Characterization of a Hydroperoxo-Heme Intermediate: Conversion of a Side-On Peroxo to an End-On Hydroperoxo Complex," *Angewandte Chemie* 48: 9262-9267.

Llewellyn, P. et al. (Mar. 21, 2008). "High Uptakes of $CO_2$ and $CH_4$ in Mesoporous Metal-Organic Frameworks MIL-100 and MIL-101," *Langmuir* 24(14): 7245-7250.

Ma, S. et al. (Dec. 29, 2007). "Metal-Organic Framework from an Anthracene Derivative Containing Nanoscopic Cages Exhibiting High Methane Uptake," *Journal of the American Chemical Society* 130(3): 1012-1016.

Ma, S. et al. (May 20, 2009). "Investigation of Gas Adsorption Performances and $H_2$ Affinities of Porous Metal-Organic Frameworks with Different Entatic Metal Centers," *Inorganic Chemistry* 48(12): 5398-5402.

Maji, T. (Feb. 2007). "A flexible interpenetrating coordination framework with a bimodal porous functionality," *Nature Materials* 6: 142-148.

Matsuda, R. et al. (Jul. 14, 2005). "Highly controlled acetylene accommodation in a metal-organic microporous material," *Nature* 436: 238-241.

McCandlish, E. et al. (Jun. 4, 1980). "Reactions of Superoxide with Iron Porphyrins in Aprotic Solvents. A High Spin Ferric Porphyrin Peroxo Complex," *Journal of the American Chemical Society* 102(12): 4268-4271.

Millward, A. et al. (Dec. 1, 2005). "Metal-Organic Frameworks with Exceptionally High Capacity for Storage of Carbon Dioxide at Room Temperature," *Journal of the American Chemical Society* 127(51): 17998-17999.

Morris, R. et al. (May 5, 2008). "Gas Storage in Nanoporous Materials," *Angewandte Chemie* 47: 4966-4981.

Mu, B. et al. (Mar. 19, 2010). "Gas Adsorption Study on Mesoporous Metal-Organic Framework UMCM-1," *The Journal of Physical Chemistry* 114(14): 6464-6471.

Mulfort, K. et al. (Jul. 18, 2007). "Chemical Reduction of Metal-Organic Framework Materials as a Method to Enhance Gas Uptake and Binding," *Journal of the American Chemical Society* 129(31): 9604-9605.

Murray, L. et al. (Mar. 25, 2009). "Hydrogen storage in metal-organic frameworks," *Chemical Society Reviews* 38: 1294-1314.

Murray, L. et al. (May 19, 2010). "Highly-Selective and Reversible $O_2$ Binding in $Cr_3(1,3,5\text{-benzenetricarboxylate})_2$," *Journal of the American Chemical Society* 132(23): 7856-7857.

(56) References Cited

OTHER PUBLICATIONS

Nandi, S. et al. (1976). "Separation of Oxygen and Nitrogen Using 5A Zeolite and Carbon Molecular Sieves," *Separation Science and Technology* 11(5): 441-453.

Owen, T. et al. (2008). "Synthesis and Characterization of Two Intensely Colored Tris(benzoylcyanoxime)iron(II) Anionic Complexes," *Inorganic Chemistry* 47(19): 8704-8713.

Que, Jr., L. et al. (1996). "Modeling the Oxygen Activation Chemistry of Methane Monooxygenase and Ribonucleotide Reductase," *Accounts of Chemical Research* 29(4): 190-196.

Roelfes, G. et al. (2003). "End-On and Side-On Peroxo Derivatives of Non-Heme Iron Complexes with Pentadentate Ligands: Models for Putative Intermediates in Biological Iron/Dioxygen Chemistry," *Inorganic Chemistry* 42(8): 2639-2653.

Rosi, N. et al. (Jan. 13, 2005). "Rod Packings and Metal-Organic Frameworks Constructed from Rod-Shaped Secondary Building Units," *Journal of the American Chemical Society* 127(5): 1504-1518.

Schuetz, M. et al. (1992). "Study on the $CO_2$-Recovery From an ICGCC-Plant," *Energy Conversion and Management* 33(5-8): 357-363.

Sono, M. et al. (1996). "Heme-Containing Oxygenases," *Chemical Reviews* 96(7): 2841-2887.

Southon, P. et al. (Jun. 3, 2011). "Reversible and Selective $O_2$ Chemisorption in a Porous Metal-Organic Host Material," *Journal of the American Chemical Society* 133: 10885-10891.

Sumida, K. (Jun. 18, 2010). "Hydrogen storage and carbon dioxide capture in an iron-based sodalite-type metal-organic framework (Fe-BTT) discovered via high-throughput methods," *Chemical Science* 1: 184-191.

Stomberg, R. et al. (1968). "The Crystal Structure of two Modifications of Oxidodiperoxido-2,2'-dipyridylchromium (VI), [$CrO(O_2)_2$ ($C_{10}H_8N_2$)]," *Acta Chemica Scandinavica* 22(5): 1439-1451.

Tanabe, K. et al. (Sep. 1, 2009). "Engineering a Metal-Organic Framework Catalyst by Using Postsynthetic Modification," *Angewandte Chemie* 48: 7424-7427.

Toby, B. (2001). "*EXPGUI*, a graphical user interface for GSAS," *Journal of Applied Crystallography* 34: 210-213.

Valenzano, L. et al. (Jun. 3, 2010). "Computational and Experimental Studies on the Adsorption of CO, $N_2$, and $CO_2$ on Mg-MOF-74," *The Journal of Physical Chemistry* 114(25): 11185-11191.

Vaska, L. (1976). "Dioxygen-Metal Complexes: Toward a Unified View," *Accounts of Chemical Research* 9: 175-183.

Watanabe, T. et al. (1984). "Matrix Isolation Infrared Spectra of Dioxygen Adducts of Iron(II) Porphyrins and Related Compounds," *The Journal of Physical Chemistry* 88(3): 440-445.

Wu, C. et al. (Jun. 4, 2005). "A Homochiral Porous Metal-Organic Framework for Highly Enantioselective Heterogeneous Asymmetric Catalysis," *Journal of the American Chemical Society* 127(25): 8940-8941.

Xue, M. et al. (Mar. 19, 2010). "Selective gas adsorption within a five-connected porous metal-organic framework," *Journal of Materials Chemistry* 20: 3984-3988.

Yao, S. et al. (2008). "A 'Side-on' Superoxonickel Complex [$LNi(O_2)$] with a Square-Planar Tetracoordinate Nickel (II) Center and Its Conversion into [$LNi(\mu\text{-}OH)_2NiL$]," *Angewandte Chemie* 47: 7110-7113.

Yoon, J.W. et al. (Jun. 14, 2007). "Gas-Sorption Selectivity of CUK-1: A Porous Coordination Solid Made of Cobalt (II) and Pyridine-2,4-Dicarboxylic Acid," *Advanced Materials* 19: 1830-1834.

Zecchina, A. et al. (1986). "Dioxygen Adducts of Iron (II) at the Surface of MgO-FeO Solid Solutions," *Journal of Molecular Catalysis* 38: 287-293.

Zhou, W. et al. (Oct. 25, 2008). "Enhanced $H_2$ Adsorption in Isostructural Metal-Organic Frameworks with Open Metal Sites: Strong Dependence of the Binding Strength on Metal Ions," *Journal of the American Chemical Society* 130(46): 15268-15269.

* cited by examiner

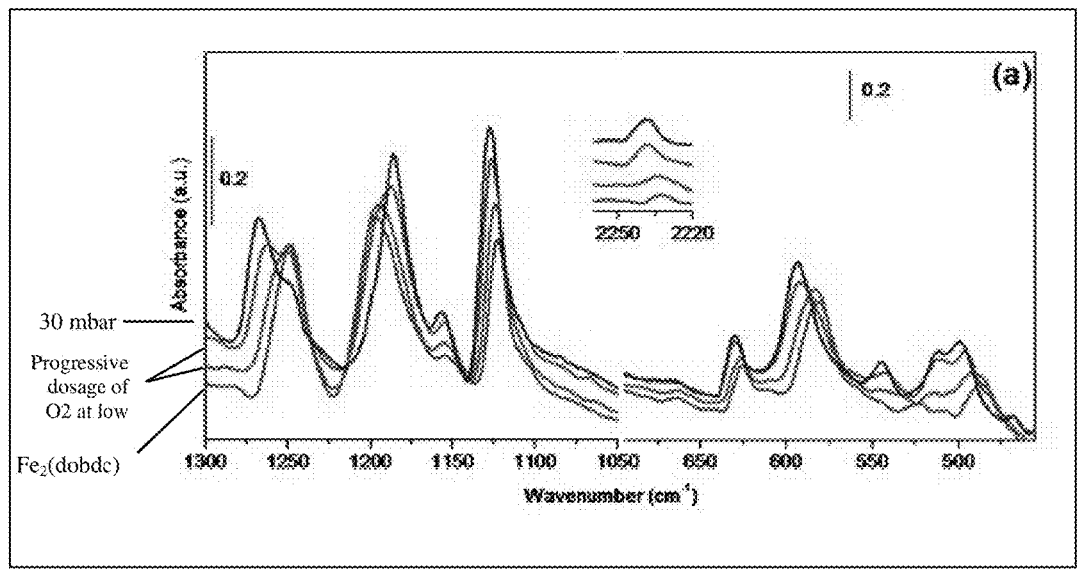
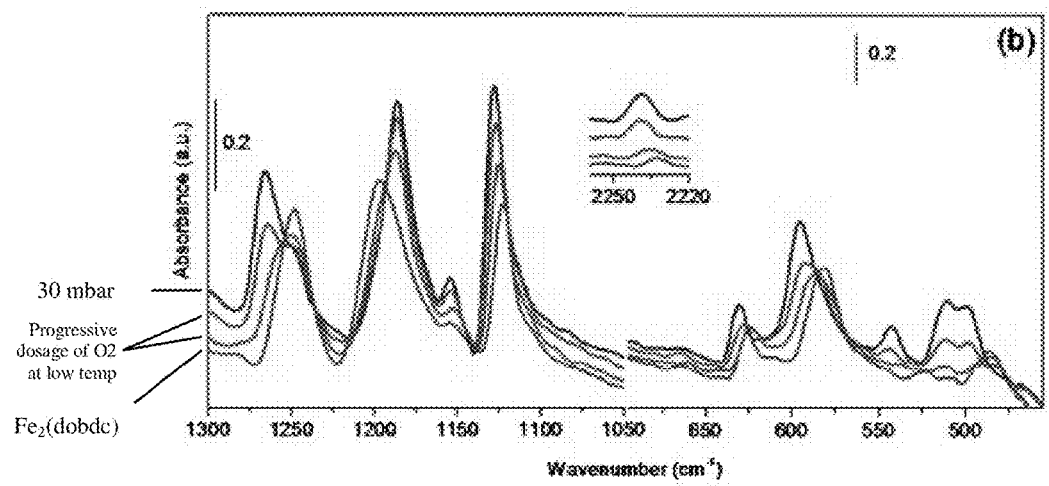
FIG. 24

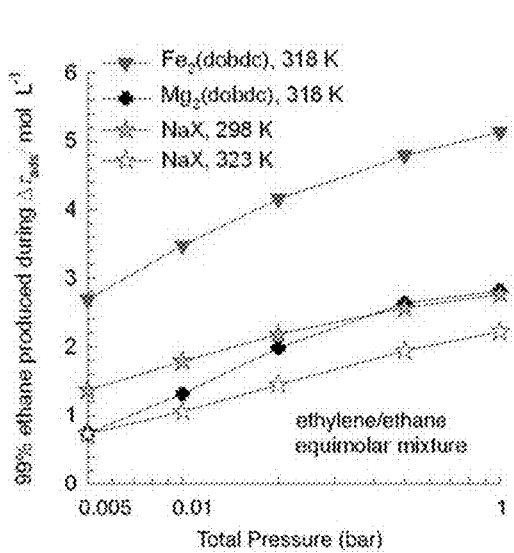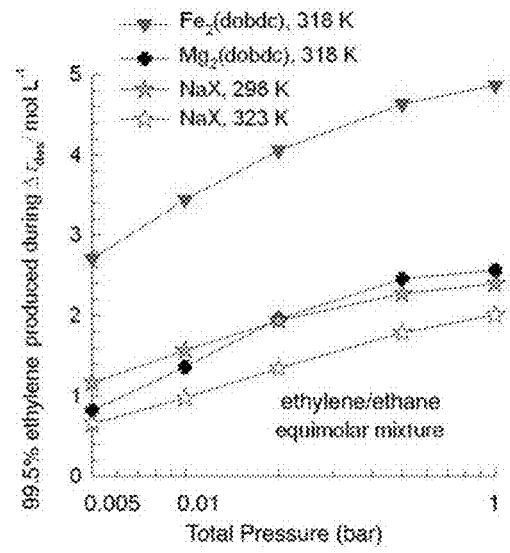
FIG. 35

FIG. 45. Dual-site Langmuir-Freundlich parameters for $O_2$ isotherms in $Fe_2(dobdc)$ at different temperatures

| Temperature | Site A | | | Site B | | |
|---|---|---|---|---|---|---|
| K | $q_{i,A,sat}$ mol kg$^{-1}$ | $b_{i,A}$ Pa$^{-v_i}$ | $v_{i,A}$ dimensionless | $q_{i,B,sat}$ mol kg$^{-1}$ | $b_{i,B}$ Pa$^{-v_i}$ | $v_{i,B}$ dimensionless |
| 201 | 7.26 | 1.38×10$^{-4}$ | 1.33 | 23.86 | 7.14×10$^{-7}$ | 1.03 |
| 209.4 | 6.62 | 1.31×10$^{-5}$ | 1.49 | 16.71 | 1.29×10$^{-5}$ | 0.78 |
| 211.4 | 5.62 | 1.15×10$^{-5}$ | 1.48 | 15.58 | 1.12×10$^{-5}$ | 0.78 |
| 214.6 | 5.34 | 5.89×10$^{-6}$ | 1.51 | 4.23 | 1.58×10$^{-5}$ | 0.87 |
| 226 | 4.51 | 4.24×10$^{-7}$ | 1.62 | 33.47 | 1.21×10$^{-4}$ | 0.51 |

FIG. 46. Dual-site Langmuir-Freundlich parameters for $N_2$ isotherms in $Fe_2(dobdc)$ at different temperatures

| Temperature | Site A | | | Site B | | |
|---|---|---|---|---|---|---|
| K | $q_{i,A,sat}$ mol kg$^{-1}$ | $b_{i,A}$ Pa$^{-v_i}$ | $v_{i,A}$ dimensionless | $q_{i,B,sat}$ mol kg$^{-1}$ | $b_{i,B}$ Pa$^{-v_i}$ | $v_{i,B}$ dimensionless |
| 201 | 123.46 | 4.19×10$^{-8}$ | 1 | 7.01 | 1.09×10$^{-4}$ | 1 |
| 211.4 | 2.66 | 3.31×10$^{-9}$ | 1 | 6.85 | 2.81×10$^{-5}$ | 1 |
| 214.6 | 3.20 | 3.77×10$^{-9}$ | 1 | 7.07 | 2.22×10$^{-5}$ | 1 |
| 226 | 3.17 | 3.75×10$^{-9}$ | 1 | 6.56 | 1.18×10$^{-5}$ | 1 |

FIG. 47. Mössbauer Spectral Parameters for $Fe_2(dobdc)$ Obtained Before and After Oxygenation[a]

| T, K | $\delta$, mm/s[b] | $\Delta E_Q$, mm/s | $\Gamma$, mm/s | Area, % | Absolute Area, (%ε)/(mm/s) | Assignment |
|---|---|---|---|---|---|---|
| 296 | 1.094(3) | 2.02(1) | 0.30(1) | 100 | - | $Fe_2(dobdc)$ |
| 94 | 1.208(1) | 2.430(1) | 0.289(1) | 91.48(2) | 16.09(1) | $Fe_2(dobdc)$ |
|  | 1.292(1) | 2.860(1) | 0.289(1) | 5.12(1) | - | $Fe_2(dobdc)$ |
|  | 1.070(1) | 0.219(2) | 0.468(2) | 3.40(1) | - | $Fe_2(dobdc)$ |
| 45 | 1.223(1) | 2.497(1) | 0.286(2) | 91.4(8) | 18.1(1) | $Fe_2(dobdc)$ |
|  | 1.31(1) | 2.95(2) | 0.286(2) | 5.4(4) | - | $Fe_2(dobdc)$ |
|  | 1.09(2) | 0.24(5) | 0.39(1) | 3.2(3) | - | $Fe_2(dobdc)$ |
| 94 | 0.772(1) | 0.624(2) | 0.320(2) | 86.4(7) | 17.50(14) | $Fe_2(O_2)_2(dobdc)$ |
|  | 1.24(1) | 2.57(2) | 0.52(3) | 13.6(7) | - | $Fe_2(dobdc)$ |
| 114 | 0.768(1) | 0.651(2) | 0.303(2) | 86.3(8) | 17.06(15) | $Fe_2(O_2)_2(dobdc)$ |
|  | 1.19(1) | 2.51(2) | 0.49(4) | 13.7(8) | - | $Fe_2(dobdc)$ |
| 193 | 0.734(1) | 0.539(1) | 0.304(1) | 85.7(8) | 13.93(10) | $Fe_2(O_2)_2(dobdc)$ |
|  | 1.11(1) | 2.24(3) | 0.66(4) | 14.3(8) | - | $Fe_2(dobdc)$ |
| 203 | 0.732(1) | 0.523(1) | 0.305(2) | 85.1(8) | 13.35(11) | $Fe_2(O_2)_2(dobdc)$ |
|  | 1.07(1) | 2.22(3) | 0.74(5) | 14.9(8) | - | $Fe_2(dobdc)$ |
| 212 | 0.735(1) | 0.518(1) | 0.324(2) | 84.6(8) | 13.00(10) | $Fe_2(O_2)_2(dobdc)$ |
|  | 1.06(1) | 2.22(3) | 0.73(5) | 15.4(8) | - | $Fe_2(dobdc)$ |
| 222 | 0.55(1) | 1.31(3) | 0.35(5) | 5.3(7) | - | $Fe_2(O_2)(dobdc)$ |
|  | 0.739(1) | 0.509(2) | 0.318(2) | 81(1) | 12.11(11) | $Fe_2(O_2)_2(dobdc)$ |
|  | 1.04(1) | 2.18(2) | 0.75(7) | 14(2) | - | $Fe_2(dobdc)$ |
| 242 | 0.619(5)[c] | 1.21(2)[c] | 0.91(3)[c] | 71(1)[c] | 11.80(11) | $Fe_2(O_2)(dobdc)$ |
|  | 0.725(3) | 0.50(2) | 0.32(2) | 23(1) | - | $Fe_2(O_2)_2(dobdc)$ |
|  | 1.03(1) | 2.10(2) | 0.52(2) | 6(1) | - | $Fe_2(dobdc)$ |
| 252 | 0.454(1)[c] | 1.449(6)[c] | 0.502(4)[c] | 94.4(3)[c] | 11.49(4) | $Fe_2(O_2)(dobdc)$ |
|  | 1.00(1) | 2.87(2) | 0.47(3) | 5.6(3) | - | $Fe_2(dobdc)$ |
| 298 | 0.415(5)[c] | 1.24(1)[c] | 0.41(1)[c] | 94.4(1)[c] | 10.91(11) | $Fe_2(O_2)(dobdc)$ |
|  | 0.84(3) | 2.93(6) | 0.50(1) | 5.6(1) | - | $Fe_2(dobdc)$ |
| 94[d] | 0.497(1)[c] | 1.200(1)[c] | 0.389(1)[c] | 93.6(1)[c] | 19.83(4) | $Fe_2(O_2)(dobdc)$ |
|  | 1.395(4) | 2.52(1) | 0.34(1) | 6.4(1) | - | $Fe_2(dobdc)$ |
| 298[d] | 0.427(1)[c] | 1.153(1)[c] | 0.388(1)[c] | 94.4(1)[c] | 12.56(1) | $Fe_2(O_2)(dobdc)$ |
|  | 0.922(3) | 2.93(1) | 0.45(1) | 5.6(1) | - | $Fe_2(dobdc)$ |

[a] The parameters are listed in the order of measurement and the statistical fitting errors are given in parentheses. The total errors are two to three times larger. [b] The isomer shifts are given relative to 295 K α-iron foil. [c] The weighted average of or sum of the three components. [d] Obtained after heating to 298 K.

FIG. 48. Unit Cell lengths and volumes

|  | $a = b$ (Å) | $c$ (Å) | $V$ (Å) |
|---|---|---|---|
| $Fe_2(dobdc)$ | 26.098(1) | 6.8512(2) | 4041.3 |
| $Fe_2(O_2)_2(dobdc)$ | 25.518(1) | 6.9661(4) | 3928.3 |
| $Fe_2(O_2)(dobdc)$ | 26.009(1) | 6.8131(7) | 3991.3 |
| $Fe_2(N_2)_2(dobdc)$ | 26.015(1) | 6.9480(2) | 4072.3 |

FIG. 49
The oxidation of propylene to acetone using $O_2$ as the oxidant.
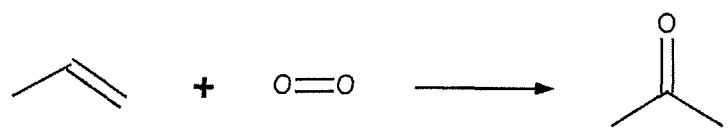
FIG. 50
Representative oxidation reactions.
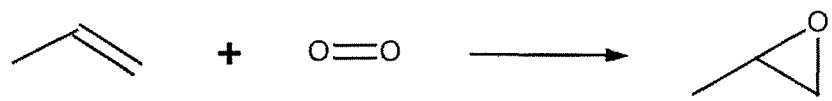
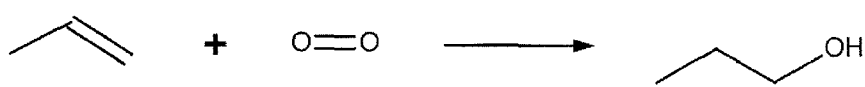
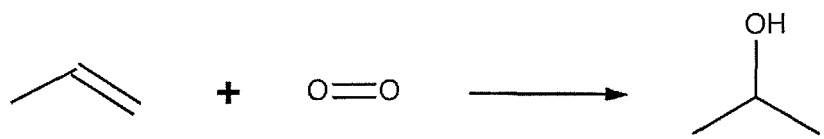

GAS SEPARATIONS WITH REDOX-ACTIVE METAL-ORGANIC FRAMEWORKS

CROSS-REFERENCE TO RELATED APPLICATION

This application claims the benefit of U.S. Provisional Application Ser. No. 61/527,331, filed Aug. 25, 2011, the contents of which is incorporated herein by reference.

FIELD OF THE INVENTION

This invention relates to $Fe_2(dobdc)$, a novel material that has a metal-organic framework with a high density of coordinatively-unsaturated $Fe^{II}$ centers lining the pore surface. This material can be used for the separation of $O_2$ from $N_2$ and in a number of additional separation applications based on selective, reversible electron transfer reactions. In addition, it can be used for many other processes, including paraffin/olefin separations, nitric oxide/nitrous oxide separation, carbon monoxide removal, acetylene storage, and as an oxidation catalyst.

BACKGROUND OF THE INVENTION

With over 100 million tons produced annually, $O_2$ is one of the most widely used commodity chemicals in the world.[1] Its potential utility in processes associated with the reduction of carbon dioxide emissions from fossil fuel-burning power plants, however, means that the demand for pure $O_2$ could grow enormously. For example, when implementing pre-combustion $CO_2$ capture, pure $O_2$ is used for the gasification of coal, which produces the feedstock for the water-gas shift reaction used to produce $CO_2$ and $H_2$.[2] In addition, oxyfuel combustion has received considerable attention for its potential utility as an alternative to post-combustion $CO_2$ capture. Here, pure $O_2$ is diluted to 0.21 bar with $CO_2$ and fed into a power plant for fuel combustion. Since $N_2$ is absent from the resulting flue gas, the requirement for post-combustion separation of $CO_2$ from $N_2$ is eliminated.[3]

The separation of $O_2$ from air is currently carried out on a large scale using an energy-intensive cryogenic distillation process.[4] Zeolites are also used for $O_2/N_2$ separation,[5] both industrially and in portable medical devices. However, this process is inherently inefficient as the materials used adsorb $N_2$ over $O_2$ with poor selectivity. By employing materials that selectively adsorb $O_2$ and can operate near ambient temperatures, lower energy and capital costs could be realized. Metal-organic frameworks ("MOFs"), which have already received considerable attention for applications in gas storage[6] and separation,[7] represent a promising new class of potential $O_2$ separation materials.

The energy cost associated with the separation of hydrocarbons, as currently carried out at enormous scale via cryogenic distillation, could potentially be lowered through development of selective solid adsorbents that operate at higher temperatures and lower pressures. As a consequence of the similar sizes and volatilities of the hydrocarbons, separations, for example, of olefin/paraffin mixtures, such as ethylene/ethane and propylene/propane, must currently be performed at low temperatures and high pressures, and are among the most energy-intensive separations carried out at large scale in the chemical industry. Because these hydrocarbon gaseous mixtures are produced by cracking long-chain hydrocarbons at elevated temperatures, a substantial energy penalty arises from cooling the gases to the low temperatures required for distillation. Thus, tremendous energy savings could be realized if materials enabling the efficient separation of hydrocarbons at higher temperatures, than currently used in distillation, and atmospheric pressure were achieved.

Current competing approaches for separating hydrocarbons include membrane designs, organic solvent-based sorbents, as well as porous solid adsorbents featuring selective chemical interactions with the carbon-carbon double bond in olefins. In this latter category, MOFs, which offer high surface areas, adjustable pore dimensions, and chemical tenability, have received considerable attention as adsorbents in gas storage and separation applications, with particular emphasis on the dense storage of methane and hydrogen, and on the efficient removal of carbon dioxide from flue gas and natural gas deposits. More recently, MOFs represent a promising new class of potential hydrocarbon separation materials.

In addition to the separation of binary olefin/paraffin mixtures, there is tremendous current interest in separating ethane, ethylene, and acetylene from methane for the purification of natural gas. Indeed, a number of porous materials are able to selectively separate methane from mixtures including $C_2$ hydrocarbons (ethane, ethylene, and acetylene). These materials, however, are unable to simultaneously purify the ethane, ethylene, and acetylene being removed from the gas stream. A separation process that utilizes the same adsorptive material for the separation and purification of all four components of a $C_1/C_2$ mixture could potentially lead to substantial efficiency and energy savings over current processes.

Ethylene produced in a naphtha cracker contains an impurity of approximately 1% acetylene. However, there are strict limitations to the amount of acetylene that can be tolerated in the feed to an ethylene polymerization reactor. The current technology for this purpose uses absorption with liquid DMF, but the use of solid adsorbents could potentially provide an energy-efficient alternative.

In addition, early efforts in developing metal-organic framework catalysts have largely focused on new synthetic methods for incorporating catalytic functionalities onto the pore surface, as well as proof-of-concept studies, such as the heterogenization of well-known homogeneous catalysts or simple acid/base activation of substrates. While these examples demonstrate the viability of metal-organic frameworks as heterogeneous catalysts, they provide little improvement over existing systems and do not take full advantage of properties unique to metal-organic frameworks, including the ability to design specific and spatially separated active sites. In particular, framework incorporation of reactive transition metal intermediates, such as metal-ligand multiple bonds or low-coordinate metal centers, is a promising area that has yet to be explored. In principle, redox catalysis involving the formation of metal species in unusual coordination environments, geometries, and/or oxidation states that are entirely unfeasible in homogeneous systems could proceed easily in the context of metal-organic frameworks wherein each metal center is held fixed and isolated.

SUMMARY OF THE INVENTION

Metal-organic frameworks have received considerable attention for a variety of gas separation applications. However, the use of $Fe_2(dobdc)$, a metal-organic framework featuring redox-active metal centers for gas separations based on selective, reversible (partial) electron transfer reactions represents a novel advance in the field. This material may be used for numerous separation and storage applications including, but not limited to, paraffin/olefin separations, oxygen/nitrogen separation, carbon monoxide removal, acetylene storage, and nitric oxide/nitrous oxide separations. This material displays incredible separation properties at temperatures that are much more favorable to those currently used in industrial applications.

One embodiment is a material including $Fe_2(2,5\text{-dioxido-}1,4\text{-benzenedicarboxylate})$. A method of making $Fe_2(dobdc)$ (dobdc=2,5-dioxido-1,4-benzenedicarboxylate) may include reacting $FeCl_2$ with $H_4dobdc$ (dobdc=2,5-dioxido-1,4-benzenedicarboxylate) in a reaction mixture to produce $Fe_2(dobdc)$. The reaction mixture may also include dimethylformamide (DMF) and methanol.

$Fe_2(dobdc)$ may use to separate a variety of mixtures. A embodiment of a method of separating a mixture stream including $O_2$ and $N_2$ may include contacting a mixture stream comprising $O_2$ and $N_2$ with a material comprising $Fe_2(dobdc)$ to obtain a stream richer in $O_2$ as compared to the mixture stream, and obtain a stream richer in $N_2$ as compared to the mixture stream.

An embodiment of a method of separating a mixture including a first chemical and a second chemical may include contacting a mixture stream including the first chemical and the second chemical with a material comprising $Fe_2(dobdc)$, obtaining a stream richer in the first chemical as compared to the mixture stream, and obtaining a stream richer in the second chemical as compared to the mixture stream.

For example, the first chemical may be a paraffin and the second chemical may be an olefin. The first chemical may be ethane and the second chemical may be ethene. The first chemical may be propane and the second chemical may be propene. The first chemical may be nitric oxide and the second chemical may be nitrous oxide.

An embodiment of a method of storing acetylene may include contacting acetylene with $Fe_2(dobdc)$.

A method of oxidizing a material may include contacting the material with $Fe_2(dobdc)$.

BRIEF DESCRIPTION OF THE DRAWINGS

FIG. 24 shows graphs of the effects of progressive dosage of $O_2$ at low temperature and of outgassing at low temperature on the IR spectra of activated $Fe_2(dobdc)$.

FIG. 35 is a series of graphs showing production capacities of 99% pure ethane (left) and 99.5% pure ethylene (right) as a function of the total pressure at the inlet to the adsorber for $Fe_2(dobdc)$, $Mg_2(dobdc)$, and NaX zeolite.

FIG. 45 is a table showing dual-site Langmuir-Freundlich parameters for O2 isotherms in Fe2(dobdc) at different temperatures.

FIG. 46 is a table shownig dual-site Langmuir-Freundlich parameters for N2 isotherms in Fe2(dobdc) at different temperatures.

FIG. 47 is a table showing Mössbauer Spectral Parameters for Fe2(dobdc) Obtained Before and After Oxygenation.

FIG. 48 is a table showing unit cell lengths and volumes.

FIG. 49 is a diagram showing the oxidation of propylene to acetone using $O_2$ as the oxidant.

FIG. 50 shows representative oxidation reactions.

DETAILED DESCRIPTION OF THE INVENTION

Figure 1:
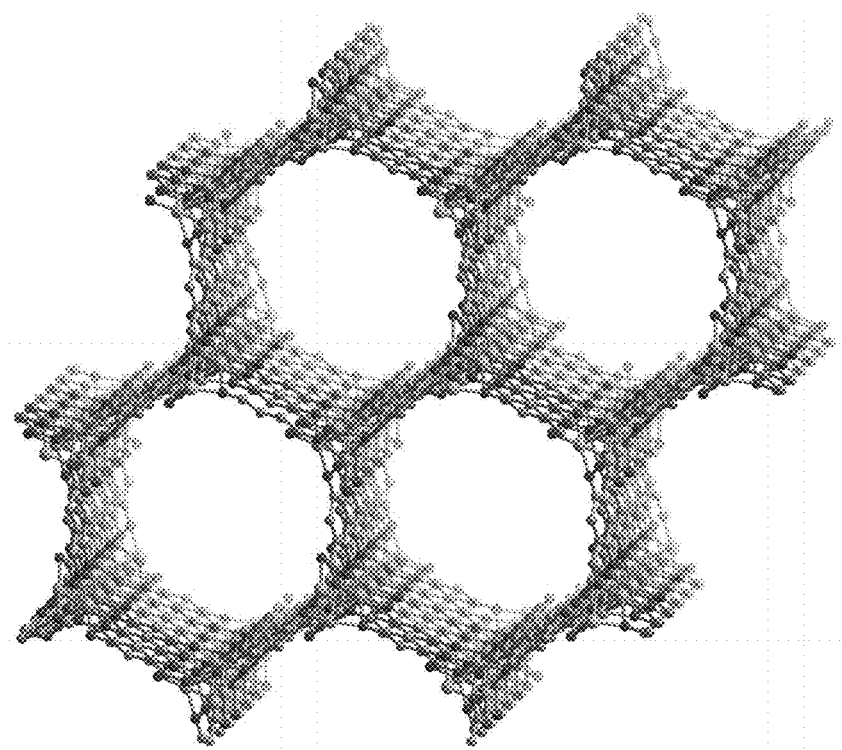
FIG. 1 is a graphical representation of a portion of the crystal structure of desolvated $Fe_2(dobdc)$ as viewed approximately along the [001] direction.

Described is a method of separating a target component from a chemical mixture using $Fe_2(dobdc)$. FIG. 1 is a portion of the crystal structure of desolvated $Fe_2(dobdc)$ as viewed approximately along the [001] direction (H atoms have been omitted for clarity.) This material has a metal-organic framework with a high density of coordinatively-unsaturated $Fe^{II}$ centers lining the pore surface. This material can be used for the separation of $O_2$ from $N_2$ and in a number of additional separation applications based on selective, reversible electron transfer reactions. In addition to being used as an $O_2$ separation material, it can be used for many other processes, including paraffin/olefin separations, nitric oxide/nitrous oxide separation, carbon monoxide removal, acetylene storage, and as an oxidation catalyst.

The high surface areas and open metal coordination sites possible within metal-organic frameworks make them particularly attractive for the development of an adsorption-based process for the separation of $O_2$ from air. While coordinatively-unsaturated metal centers have been generated in such materials via chelation by post-synthetically modified bridging ligands,[8] or via insertion into open ligand sites,[9] they are most often created by evacuation of frameworks that have metal-bound solvent molecules. This strategy has been employed to expose $M^{2+}$ cation sites in some of the most widely-studied frameworks, such as $M_2(dobdc)$ (M=Mg, Mn, Co, Ni, Zn; $dobdc^{4-}$=2,5-dioxido-1,4-benzenedicarboxylate)[10] and $M_3(BTC)_2$ (M=Cu, Cr, Mo; $BTC^{3-}$=1,3,5-benzenetricarboxylate).[11]

To achieve a high selectivity for the coordination of $O_2$ over $N_2$, one can take advantage of the greater electron affinity of the former molecule. Indeed, coordinatively-unsaturated $Cr^{II}$ centers in $Cr_3(BTC)_2$ give rise to an exceptionally strong preference for adsorbing $O_2$ relative to $N_2$ via charge transfer. Although the interaction with $O_2$ proved too strong to achieve full reversibility with this material, the result demonstrates the potential power of frameworks with redox-active metal centers for the separation of $O_2$ and $N_2$. In view of its widespread deployment as an $O_2$ carrier in biology,[12] $Fe^{II}$ was chosen.

The air-free reaction between $FeCl_2$ and $H_4dobdc$ ($dobdc^{4-}$=2,5-dioxido-1,4-benzenedicarboxylate) in a mixture of DMF and methanol affords $Fe_2(dobdc).4DMF$, a metal-organic framework adopting the MOF-74 (or CPO-27) structure type. The desolvated form of this material displays a BET surface area of 1350-1360 $m^2/g$ and features a hexagonal array of one-dimensional 11 Å wide channels lined with coordinatively-unsaturated $Fe^{II}$ centers. With a compact tetra-anionic bridging ligand, the structure features a unprecedented high surface density of 2.9 $Fe^{II}$ coordination sites available per 100 11 $Å^2$ on its surface, with spacings of just 6.84(1) and 8.98(2) Å between iron atoms along and around a channel, respectively. Thus, it appears to provide a near optimal platform for the high-capacity adsorption of small olefins, such as ethylene and propylene. Furthermore, the $Mg^{2+}$ or $Co^{2+}$ analogues of this structure type have recently been shown to disply selective adsorption for olefins over paraffins. The higher the surface area and softer metal character of $Fe_2(dobdc)$ as compared to the recently reported materials should lend both higher selectivity and capacity to the iron(II) framework.

Gas adsorption isotherms at 298 K indicate that $Fe_2$(dobdc) binds $O_2$ preferentially over $N_2$, with an irreversible capacity of 9.3 wt %, corresponding to the adsorption of one $O_2$ molecule per two iron centers. Remarkably, at 211 K, $O_2$ uptake is fully reversible and the capacity increases to 18.2 wt %, corresponding to the adsorption of one $O_2$ molecule per iron center. Mössbauer and infrared spectra are consistent with partial charge transfer from iron(II) to $O_2$ at low temperature and complete charge transfer to form iron(III) and $O_2^{2-}$ at room temperature. The results of Rietveld analyses of powder neutron diffraction data (4 K) confirm this interpretation, revealing $O_2$ bound to iron in a symmetric side-on mode with $d_{O-O}$=1.25(1) Å at low temperature and in a slipped side-on mode with $d_{I-O}$=1.6(1) Å when oxidized at room temperature. Application of ideal adsorbed solution theory in simulating breakthrough curves show $Fe_2(dobdc)$ to be a promising material for the separation of $O_2$ from air at temperatures well above those currently employed in industrial settings.

Herein, we report the synthesis and $O_2$ binding properties of $Fe_2$(dobdc), a metal-organic framework with a high density of coordinatively-unsaturated $Fe^{II}$ centers lining the pore surface.

This invention will be better understood with reference to the following experimental examples, which are intended to illustrate specific embodiments within the overall scope of the invention.

Experimental Section

General. Unless otherwise noted, all procedures were performed under an $N_2$ atmosphere using standard glovebox or Schlenk techniques. Anhydrous, air-free N,N-dimethylformamide (DMF) and methanol were purchased from commercial vendors and further deoxygenated by purging with $N_2$ for at least 1 h prior to being transferred to an inert atmosphere glovebox. All other reagents were obtained from commercial vendors at reagent grade purity or higher and used without further purification.

Synthesis of $Fe_2$(dobdc). Anhydrous ferrous chloride (1.1 g, 9.0 mmol), 1,4-dihydroxyterephthalic acid (0.71 g, 3.6 mmol), DMF (300 mL) and methanol (36 mL) were added to a 500-mL Schlenk flask. The reaction mixture was heated at 393 K and stirred for 18 h to afford a red-orange precipitate. The solid was collected by filtration and washed with 100 mL of DMF to yield 2.0 g (91%) of $Fe_2$(dobdc)· 4DMF. Anal. Calcd. for $C_{20}H_{30}Fe_2N_4O_{10}$: C, 40.16; H, 5.06; N, 9.37. Found: C, 40.26; H, 5.08; N, 9.24. A sample of this compound (1.9 g, 3.3 mmol) was soaked in 100 mL of DMF at 393 K for 24 h after which the solvent was decanted, and the solid was then soaked in 100 mL of methanol at 343 K for 24 h. The methanol exchange was repeated three times, and the solid was collected by filtration to yield 1.25 g (87%) of $Fe_2$(dobdc)·4MeOH as a yellow-ochre powder. Anal. Calcd. for $Fe_2Cl_2H_{18}O_{10}$: C, 33.21; H, 4.18. Found: C, 33.42; H, 4.09. A sample of this compound was fully desolvated by heating under dynamic vacuum (<10 μbar) at 433 K for 24 h to yield $Fe_2$(dobdc) as a light green powder. Anal. Calcd. for $Fe_2C_8H_2O_6$: C, 31.42; H, 0.66. Found: C, 31.55; H, 0.50.

Low-Pressure Gas Adsorption Measurements. For all gas adsorption measurements 200-225 mg of $Fe_2$(dobdc)· 4MeOH was transferred to a pre-weighed glass sample tube under an atmosphere of nitrogen and capped with a Transeal. Samples were then transferred to Micromeritics ASAP 2020 gas adsorption analyzer and heated at a rate of 0.1 K/min from room temperature to a final temperature of 433 K. Samples were considered activated when the outgas rate at 433 K was less than 2 Oar/min. Evacuated tubes containing degassed samples were then transferred to a balance and weighed to determine the mass of sample, typically 150-175 mg. The tube was transferred to the analysis port of the instrument where the outgas rate was again determined to be less than 2 Oar/min at 433 K. Nitrogen gas adsorption isotherms at 77 K were measured in liquid nitrogen, while $O_2$ measurements between 200 and 273 K were measured using liquid nitrogen/solvent slurry baths. All measurements above 273 K were performed using a recirculating dewar connected to an isothermal bath.

Transmission Infrared and Diffuse Reflectance UV-vis-NIR Spectroscopy. Prior to $O_2$ dosing, $Fe_2$(dobdc)·4MeOH samples were activated under dynamic vacuum (residual pressure<0.1 μbar) at 433 K for 18 h. Infrared spectra were collected on thin deposits of sample supported on a silicon wafer in an airtight quartz cell that allows for collection of spectra under controlled atmospheres. The film was prepared from a suspension of $Fe_2$(dobdc) in methanol. Transmission FTIR spectra were collected at 2-$cm^{-1}$ resolution on a Bruker IFS 66 FTIR spectrometer equipped with a DTGS detector. Diffuse Reflectance UV-vis-NIR spectra were recorded on a Cary 5000 spectrophotometer equipped with reflectance sphere. Spectra of the desolvated framework were recorded on a thick self-supported wafer of the sample. Attenuated total reflection (ATR) spectra were recorded on a Bruker single reflection ALPHA-Platinum ATR spectrometer with a diamond crystal accessory.

Neutron Diffraction Data Collection and Refinement. Neutron powder diffraction (NPD) experiments were carried out on 0.9698 g and 0.6200 g of $Fe_2$(dobdc) and $Fe_2(O_2)$ (dobdc) respectively using the high-resolution neutron diffractometer, BT1, at the National Institute of Standards and Technology Center for Neutron Research (NIST). Both samples were placed in a He purged glove box, loaded into a vanadium can equipped with a gas loading valve, and sealed using an indium O-ring. Neutron diffraction data were collected using a Ge(311) monochromator with an in-pile 60' collimator corresponding to a wavelength of 2.0782 Å. The samples were loaded into a top-loading closed cycle refrigerator and then data were collected at 4 K. After data collection of the bare material, $O_2$ loading was then carried out. The sample was warmed to 125 K and then exposed to a predetermined amount of gas (2.0 $O_2$ per $Fe^{2+}$). Upon reaching an equilibrium pressure at the loading temperature, the sample was then slowly cooled to ensure complete adsorption of the $O_2$. Data was then collected at 4 K.

NPD measurements of $N_2$-loaded $Fe_2$(dobdc) were performed on the Echidna instrument[14] located at the Opal research reactor and operated by the Bragg Institute within the Australian Nuclear Science and Technology Organisation (ANSTO). A desolvated sample weighing 1.079 g was transferred to a vanadium cell in an Ar-filled glovebox. The cell was equipped with heaters for the gas line and valve to allow condensable gases to be loaded in the sample when mounted in the closed cycle refrigerator. The high-resolution diffractometer was configured with a Ge(331) monochromator using a take-off angle of 140° with no collimation at the monochromator and fixed tertiary 5' collimation, resulting in a wavelength of 2.4406 Å. Diffraction data were collected at ~9 K for the evacuated framework and with sequential loadings of 0.5, 1.0 and 2.0 $N_2$:Fe, where the cryostat and sample were heated above 80 K to facilitate adsorption of the 99.999% pure $N_2$ gas.

All NPD data were analyzed using the Rietveld method as implemented in EXPGUI/GSAS. The activated $Fe_2$(dobdc) model was refined with all structural and peak profile parameters free to vary, resulting in a structure very similar to that determined using single crystal X-ray diffraction. Fourier difference methods were then employed to locate the adsorbed molecules in the data collected from the samples subsequently loaded with $O_2$ or $N_2$. The atoms in the adsorbed molecules were modeled individually. For the $N_2$ adsorbed sample the two N atoms were constrained to maintain the fractional occupancy and isotropic displacement parameter within each diatomic molecule. For analysis of $Fe_2$(dobdc) loaded with 2.0 $O_2$/Fe, only fractional occupancies were constrained to maintain the same values, while all other parameters were allowed to vary. Further, for data collection of the irreversibly oxidized sample, $Fe_2(O_2)$ (dobdc), the modeled O atoms were constrained to maintain the same fractional occupancies and isotropic displacement parameters. Once a stable structural model was obtained the isotropic displacement parameters of the adsorbed $O_2$ molecule were allowed to vary independently of one another and then the displacement parameter for O(1b) were allowed to refine anisotropically.

Figure 22:
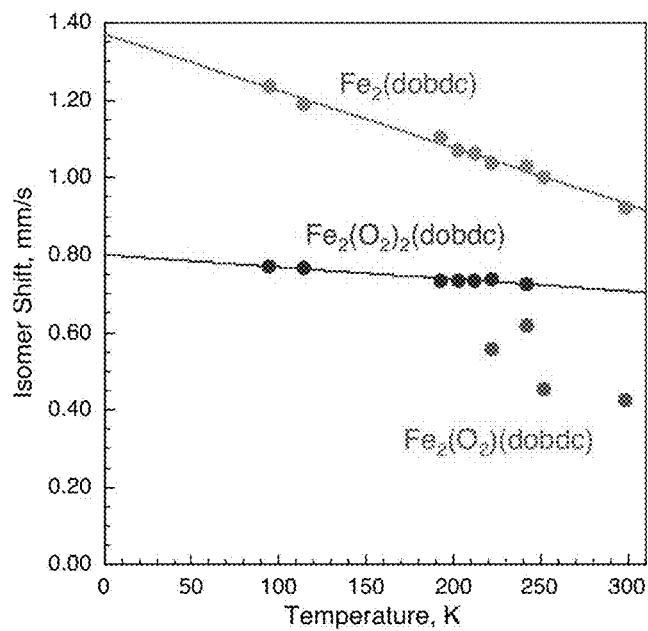
FIG. 22 is a graph showing temperature dependence of the isomer shifts $Fe_2(dobdc)$, $Fe_2(O_2)_2(dobdc)$, and $Fe_2(O_2)(dobdc)$.
Figure 23:
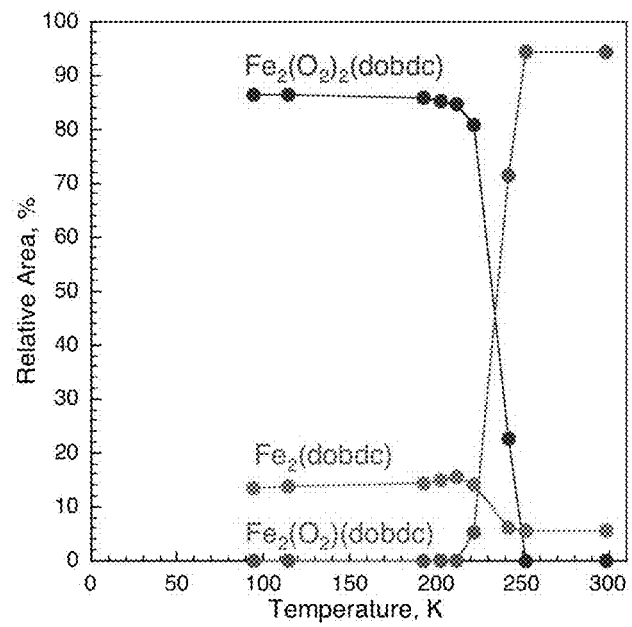
FIG. 23 is a graph showing relative absorption areas of $Fe_2(dobdc)$, $Fe_2(O_2)_2(dobdc)$, and $Fe_2(O_2)(dobdc)$ as a function of temperature.

Mössbauer Spectroscopy. The Mössbauer spectra of $Fe_2$(dobdc), $Fe_2(O_2)_2$(dobdc), and $Fe_2(O_2)$(dobdc) were measured at various temperatures between 94 and 298 K with a constant acceleration spectrometer which utilized a rhodium matrix cobalt-57 source, and was calibrated at 295 K with α-iron foil. The absorber contained 45(1) mg/cm$^2$ of powder mixed with boron nitride. The $Fe_2$(dobdc) absorber was prepared in an $N_2$-filled glovebox, cooled to 77 K with liquid nitrogen, and inserted into a pre-cooled cryostat under dry helium. The sample of $Fe_2(O_2)_2$(dobdc) was prepared in situ by dosing the evacuated cryostat to 300 mbar $O_2$ at 94 K and allowing 3 h for equilibration. The sample of $Fe_2(O_2)$(dobdc) was prepared in situ by warming the oxidized sample above 250 K in the cryostat. The spectra of $Fe_2$(dobdc) were measured at 298, 94, and 45 K in the absence of $O_2$, after which the sample was warmed to 94 K and dosed with $O_2$. Additional spectra were measured between 94 and 298 K and then subsequently measured again at 94 and 298 K. All spectra were fit with symmetric Lorenzian quadrupole doublets; the resulting spectral parameters, listed in the order of measurement, are given in FIG. 47. FIG. 47 shows Mössbauer Spectral Parameters for Fe2(dobdc) Obtained before and after oxygenation. The temperature dependence of the observed isomer shifts and relative absorption areas are plotted in FIGS. 22 and 23, respectively; further spectral details are provided in the Supporting Information. FIG. 22 is a temperature dependence of the isomer shifts $Fe_2$(dobdc), $Fe_2(O_2)_2$(dobdc), and $Fe_2(O_2)$(dobdc); and FIG. 23 is a relative absorption areas of $Fe_2$(dobdc), $Fe_2(O_2)_2$(dobdc), and $Fe_2(O_2)$(dobdc) as a function of temperature; The relative statistical errors associated with the isomer shifts, quadrupole splittings, line widths, percent areas, and absolute areas between 94 and 298 K are also given in FIG. 47.

Other Physical Measurements. Thermogravimetric analysis was carried out at a ramp rate of 1° C./min in a nitrogen flow with a TA instruments TGA 5000. Powder X-ray diffraction patterns were collected on air-free samples sealed in quartz capillaries on a Bruker Advance D8 powder X-ray diffractometer equipped with a capillary stage.

Results and Discussion

Figure 11:
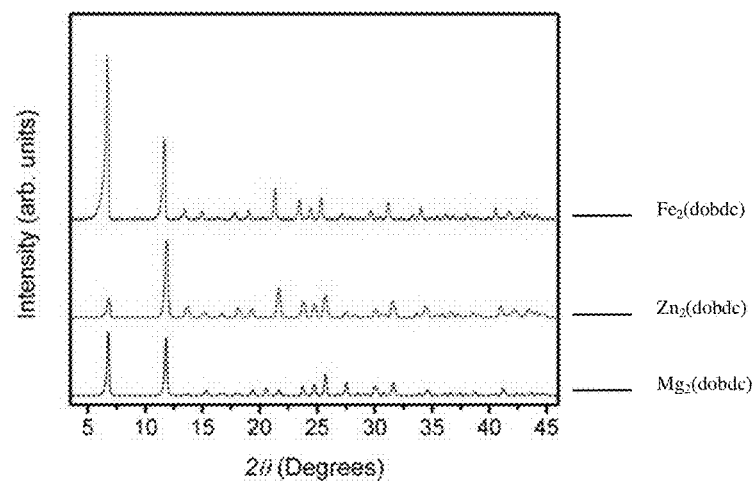
FIG. 11 is a graph comparing the powder X-ray diffraction patterns of as-synthesized $Fe_2(dobdc)$, $Zn_2(dobdc)$, and $Mg_2(dobdc)$.

Synthesis of $Fe_2$(dobdc). The reaction of anhydrous $FeCl_2$ with $H_4$dobdc in a mixture of DMF and methanol affords a solvated form of $Fe_2$(dobdc) as a red-orange microcrystalline powder. FIG. 11 is a comparison between the powder X-ray diffraction patterns of as-synthesized $Fe_2$(dobdc), $Zn_2$(dobdc), and $Mg_2$(dobdc). Powder x-ray diffraction data (see FIG. 11) show the compound to adopt the MOF-74 or CPO-27 structure type displayed in FIG. 1, as previously reported for $M_2$(dobdc) (M=Mg, Mn, Co, Ni, Zn).[10] The compound rapidly changes color to dark brown upon exposure to air, presumably due to at least partial oxidation of the $Fe^{II}$ centers by $O_2$. Based upon color, it is likely that the brown phase previously reported as $Fe_2$(dobdc) is actually some oxidized form of the compound.[10h] Note that, perhaps owing to their air-sensitive nature, only a very few metal-organic frameworks based upon iron(II) have yet been isolated.[15]

Figure 12:
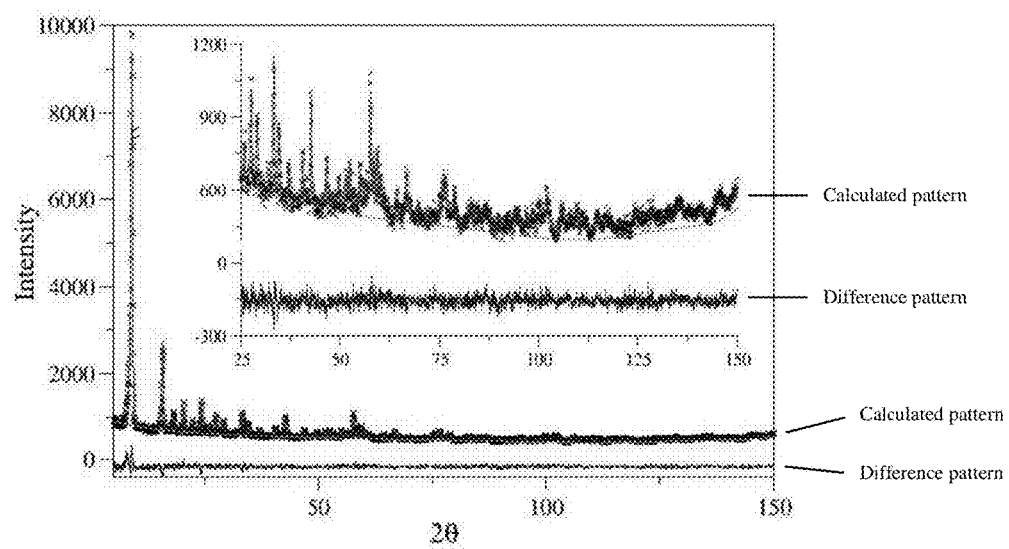
FIG. 12 is a Rietveld refinement of the experimental neutron diffraction pattern of desolvated $Fe_2(dobdc)$.

The new framework was completely desolvated by soaking it in methanol to exchange coordinated DMF, followed by heating under dynamic vacuum at 433 K for 48 h. The resulting solid was light green in color. FIG. 12 is a Rietveld refinement of the experimental neutron diffraction pattern of desolvated $Fe_2$(dobdc). The calculated pattern is in good agreement with the experimental data (crosses) as evidenced by the difference pattern. Rietveld analysis of the powder neutron diffraction data collected for $Fe_2$(dobdc) indicate retention of the framework structure with no residual bound solvent (see FIG. 12). Thus, desolvation converts the $Fe^{II}$ centers of the framework from an octahedral coordination geometry with one bound solvent molecule to a square pyramidal geometry with an open coordination site.

Figure 13:
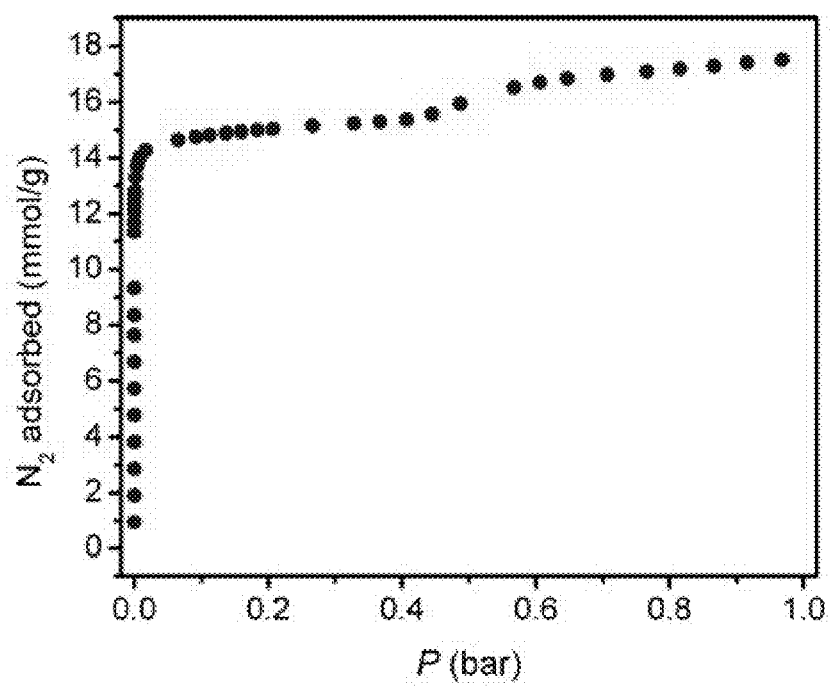
FIG. 13 is a graph showing $N_2$ adsorption in $Fe_2(dobdc)$ at 77 K.
Figure 14:
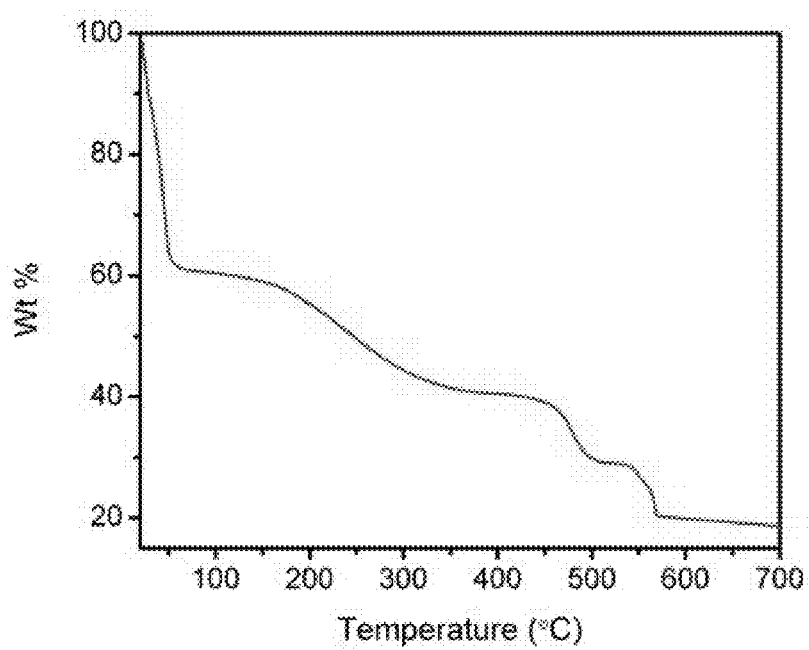
FIG. 14 is a TGA of $Fe_2(dobdc)$ under $N_2$.

FIG. 13 is $N_2$ adsorption in $Fe_2$(dobdc) at 77 K. Low-pressure $N_2$ adsorption data obtained for $Fe_2$(dobdc) at 77 K reveal a type I adsorption isotherm characteristic of a microporous solid. The data indicate a BET surface area of 1360 m$^2$/g (1535 m$^2$/g Langmuir) (see FIG. 13). This value is significantly higher than the 920 m$^2$/g Langmuir surface area reported for the material prepared in the presence of air and is in close agreement with the BET surface areas of 1218 m$^2$/g and 1341 m$^2$/g reported for $Ni_2$(dobdc) and $Co_2$(dobdc), respectively, indicating full evacuation of solvent molecules from the pores of the material.[16] FIG. 14 is a TGA of $Fe_2$(dobdc) under $N_2$.

Figure 2:
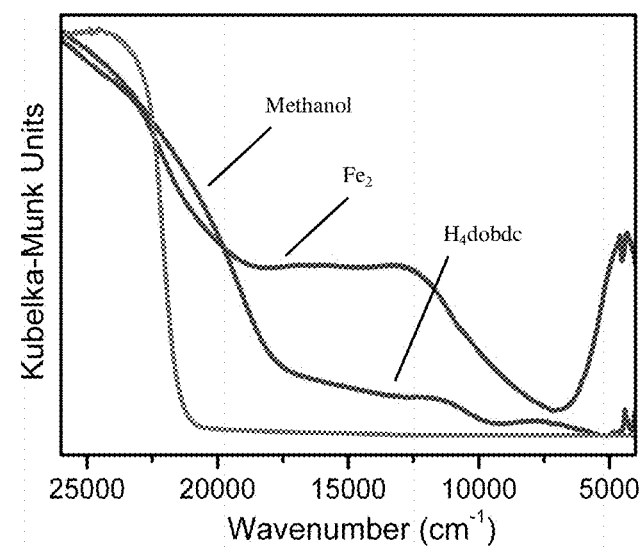
FIG. 2 is a diffuse reflectance UV-visible-NIR spectra of methanol solvated, desolvated $Fe_2(dobdc)$, and $H_4dobdc$.

UV-vis-NIR Spectroscopy. FIG. 2 is a diffuse reflectance UV-visible-NIR spectra of methanol solvated, desolvated $Fe_2$(dobdc), and $H_4$dobdc. FIG. 2 shows the electronic absorption spectra for $Fe_2$(dobdc)·4MeOH, $Fe_2$(dobdc), and $H_4$dobdc. The spectrum for the yellow-ochre compound $Fe_2$(dobdc)·4MeOH exhibits a low energy doublet with peaks at 11600 cm$^{-1}$ and 7600 cm$^{-1}$. High-spin Fe" centers in an octahedral symmetry are expected to show a spin-allowed transition, $^5E_g \leftarrow {^5T_{2g}}$, in the near infrared region,[17] and in many compounds this band is split into a doublet due to a lower symmetry ligand field, which lifts the two-fold orbital degeneracy of the $^5E_g$ term. At higher energy, a broad component centered at 16000 cm$^{-1}$ and a strong band with a maximum around 21000 cm$^{-1}$ appear in the spectrum. The structure and position of these absorptions suggest they arise from mixing of d-d and charge transfer (LMCT and MLCT) transitions.[18] Heating the solvated material at 433 K in vacuo results in removal of coordinated methanol with the formation of five-coordinative Fe" centers. The corresponding change in symmetry at the metal site to approximately $C_{4v}$ strongly affects the electronic transitions, which is evident from the spectrum of the desolvated material. In particular, the band at 21000 cm$^{-1}$ slightly shifts to lower energy, mixing with the component at 16000 cm$^-$ and with the d-d transition, resulting in a strong absorption extending through 13000 cm$^{-1}$. The very strong absorption maximum at 4400 cm$^{-1}$ is associated with a d-d transition, with enhanced intensity owing to loss of an approximate inversion center in the ligand field upon conversion from pseudooctahedral to square pyramidal coordination.

Figure 3:
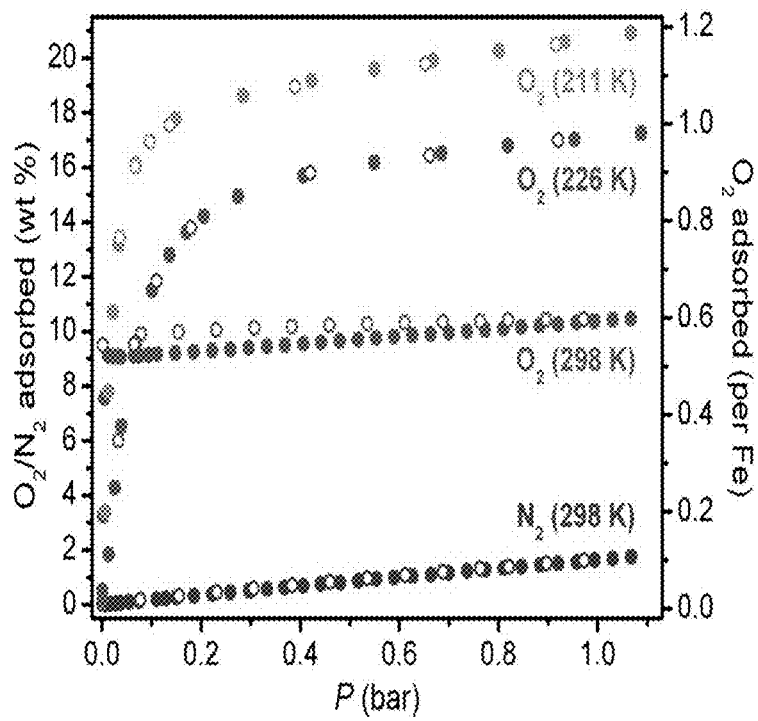
FIG. 3 is a graph showing excess $O_2$ and $N_2$ adsorption isotherms collected for $Fe_2(dobdc)$ at various temperatures.

$O_2$ and $N_2$ Adsorption. Gas adsorption isotherms indicate that $Fe_2$(dobdc) preferentially binds $O_2$ over $N_2$ at all temperatures measured (201, 211, 215, 226, and 298 K). FIG. 3 is a graph showing excess $O_2$ adsorption isotherms collected for $Fe_2$(dobdc) at 211, 226, and 298 K, and $N_2$ adsorption at 298 K. Filled and open circles represent adsorption and desorption, respectively. As shown in FIG. 3, the $O_2$ adsorption isotherm measured at 298 K is extremely steep, climbing to near 9.3 wt % at a pressure of just 0.01 bar. As the pressure is increased to 1.0 bar, uptake increases slightly to 10.4 wt %. The steep initial rise in the isotherm is consistent with strong binding of $O_2$ to some of the $Fe^{II}$ centers, while the subsequent gradual increase in adsorption is likely due to $O_2$ physisorbed to the framework surface. Importantly, the amount of strongly bound $O_2$ corresponds to 0.5 molecules per iron center. Adsorption of $N_2$ under these conditions is noticeably lower, gradually rising to just 1.3 wt % at 1.0 bar. The selectivity factor of this material, calculated as the mass of $O_2$ adsorbed at 0.21 bar divided by the mass of $N_2$ adsorbed at 0.79 bar, is 7.5. Although this selectivity factor is among the highest reported for metal-organic frameworks,[19] room temperature $O_2$ adsorption was found to be irreversible. Attempts to identify conditions to release coordinated $O_2$ by heating at temperatures of up to 473 K under dynamic vacuum ultimately lead to decomposition of the framework.

Figure 4:
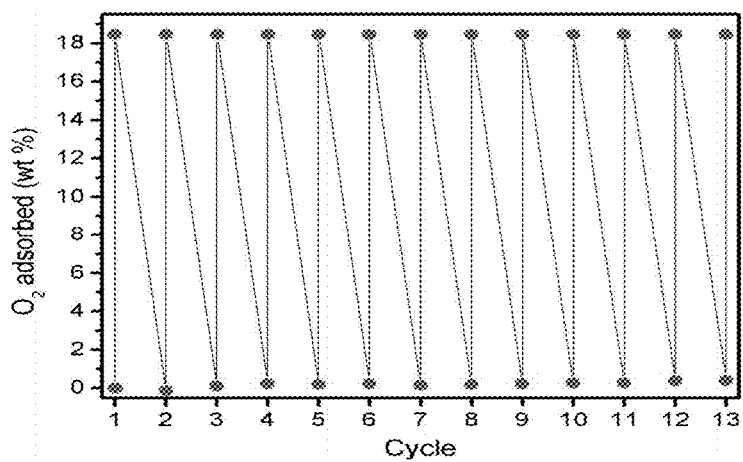
FIG. 4 is graph showing the uptake and release of $O_2$ in $Fe_2(dobdc)$ over 13 cycles at 211 K.

Upon dosing $Fe_2$(dobdc) with $O_2$ at lower temperatures, it was noted that the black color characteristic of the oxidized framework could be returned to light green by applying vacuum to the sample, suggesting reversible $O_2$ adsorption. Additional $O_2$ adsorption experiments confirmed this result. As shown in FIG. 3, at 226 K the framework adsorbs 14.1 wt % $O_2$ at 0.21 bar, or 0.82 $O_2$ molecules per iron site. Although adsorption at this temperature is largely reversible, $O_2$ uptake decreases to 11.9 wt % after four adsorption/desorption cycles. Lowering the adsorption temperature to 211 K results in an increased $O_2$ uptake of 18.2 wt %, corresponding to 1.0 molecules of $O_2$ per iron center. The amount of $O_2$ adsorbed at this temperature was found to decrease only slightly to 17.5 wt % after eight adsorption/desorption experiments. However, by cycling at a rapid rate, allowing just 2 min for adsorption and 25 min for desorption (instead of the 4-5 h typically required for collecting a full isotherm), resulted in no noticeable loss in adsorption capacity after 13 cycles (see FIG. 4, which is a graph showing the uptake and release of $O_2$ in $Fe_2$(dobdc) over 13 cycles at 211 K. Adsorption occurred within 2 min upon application of 0.21 bar of $O_2$ and desorption was carried out by placing the sample under dynamic vacuum for 25 min).

Figure 15:
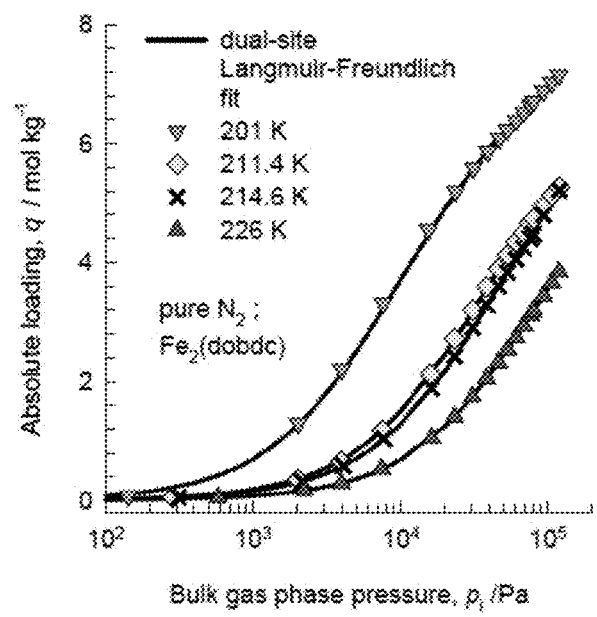
FIG. 15 a graph showing dual-site Langmuir-Freundlich fits for Oxygen and Nitrogen adsorption in $Fe_2(dobdc)$.

To predict how $Fe_2$(dobdc) would perform as an $O_2/N_2$ separation material, ideal adsorbed solution theory (ILAST) was employed at temperatures for which $O_2$ adsorption is reversible. The $O_2$ and $N_2$ isotherms measured at 201, 211, 215, and 226 K were modeled with dual-site Langmuir-Freundlich fits. FIG. 15 is dual-site Langmuir-Freundlich fits for Oxygen (upper) and Nitrogen (lower) adsorption in $Fe_2$(dobdc). The continuous solid lines are the dual-site Langmuir-Freundlich fits using the parameters specified in FIG. 45 ($O_2$) and FIG. 46 ($N_2$). FIG. 45 shows dual-site Langmuir-Freundlich parameters for O2 isotherms in Fe2(dobdc) at different temperatures. FIG. 46 shows dual-site Langmuir-Freundlich parameters for N2 isotherms in Fe2(dobdc) at different temperatures.

Figure 16:
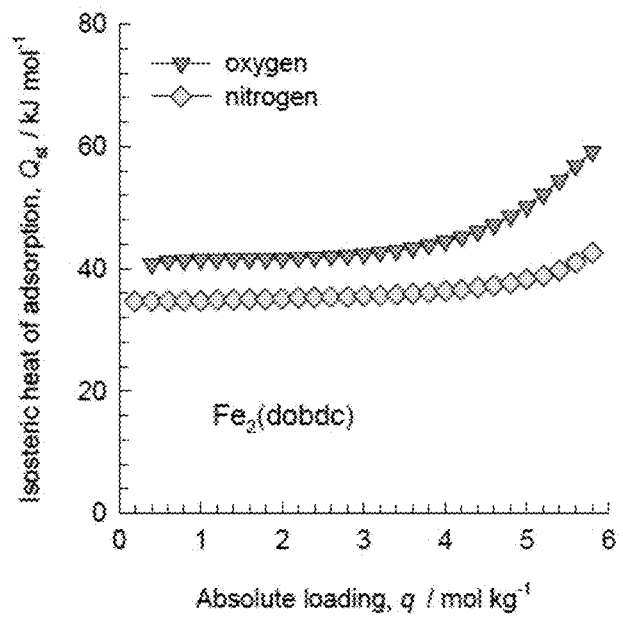
FIG. 16 is a graph showing isosteric heats of adsorption of $O_2$ and $N_2$.
Figure 17:
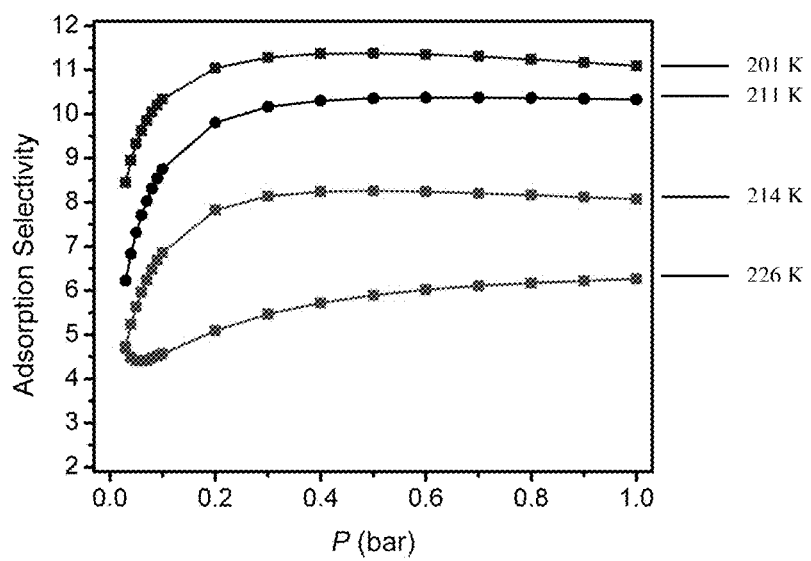
FIG. 17 is a graph of $O_2/N_2$ selectivity as a function of pressure at various temperatures.

FIG. 16 is isosteric heats of adsorption of $O_2$ and $N_2$, determined from the dual-Langmuir-Freundlich fits in FIG. 45, FIG. 46 and application of equation (2). Isosteric heats of adsorption calculated from these fits are plotted in FIG. 16 and indicate higher enthalpies for $O_2$ adsorption than $N_2$ adsorption over the entire pressure range measured. The higher propensity of $O_2$ to accept charge from $Fe^{II}$ results in a larger initial isosteric heat of −41 kJ/mol, as compared to that of $N_2$ (−35 kJ/mol). Accordingly, $Fe_2$(dobdc) displays a high $O_2/N_2$ selectivity at 201, 211, 215, and 226 K. FIG. 17 shows $O_2/N_2$ selectivity as a function of pressure at 201 K, 211 K, 214 K, and 226 K. The selectivity ranges from 4.4 to over 11 and reaches a maximum of 11.4 at 201 K and about 0.4 bar.

Figure 5:
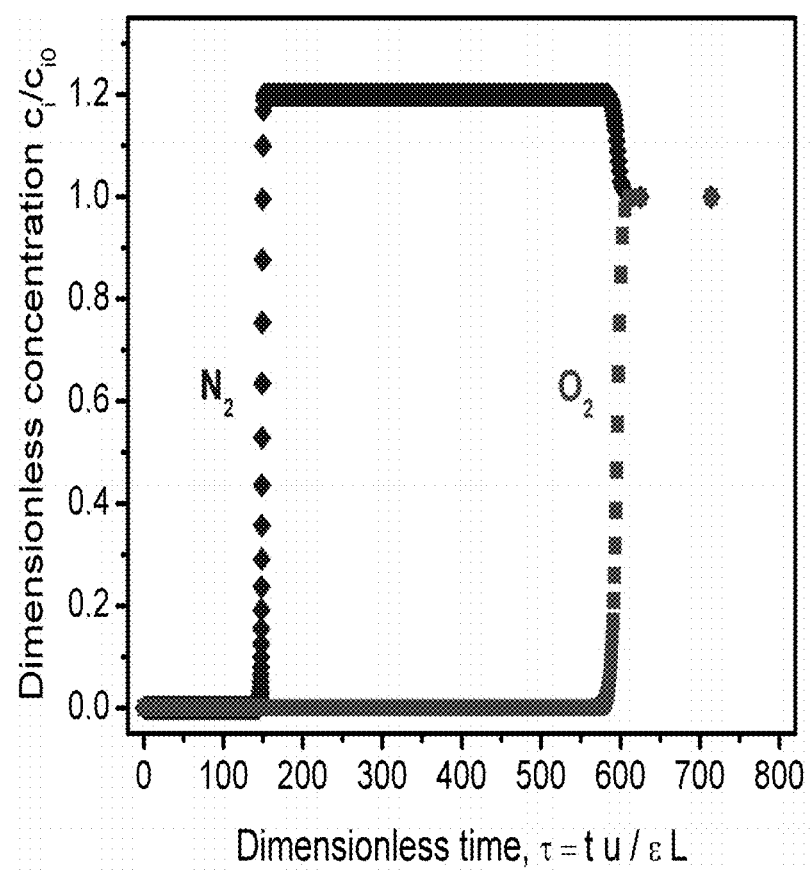
FIG. 5 is a graph that shows calculated $N_2$ and $O_2$ breakthrough curves during adsorption of simulated air by $Fe_2(dobdc)$.
Figure 18:
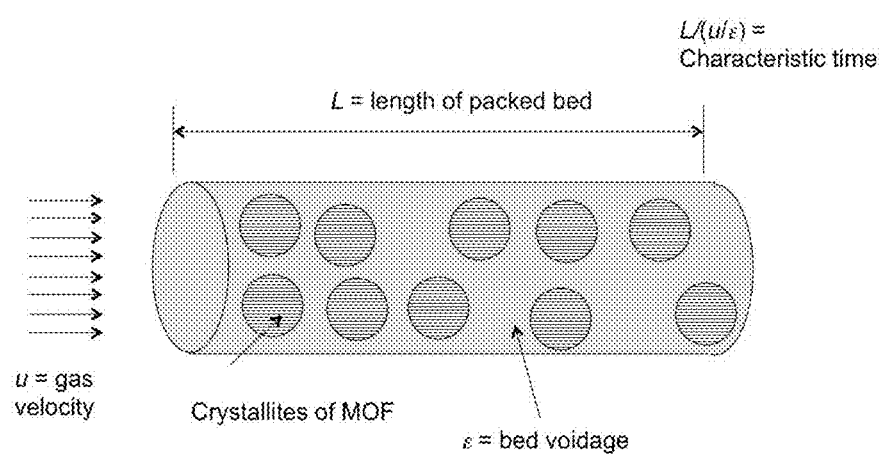
FIG. 18 is a schematic drawing of VSA apparatus.
Figure 19:
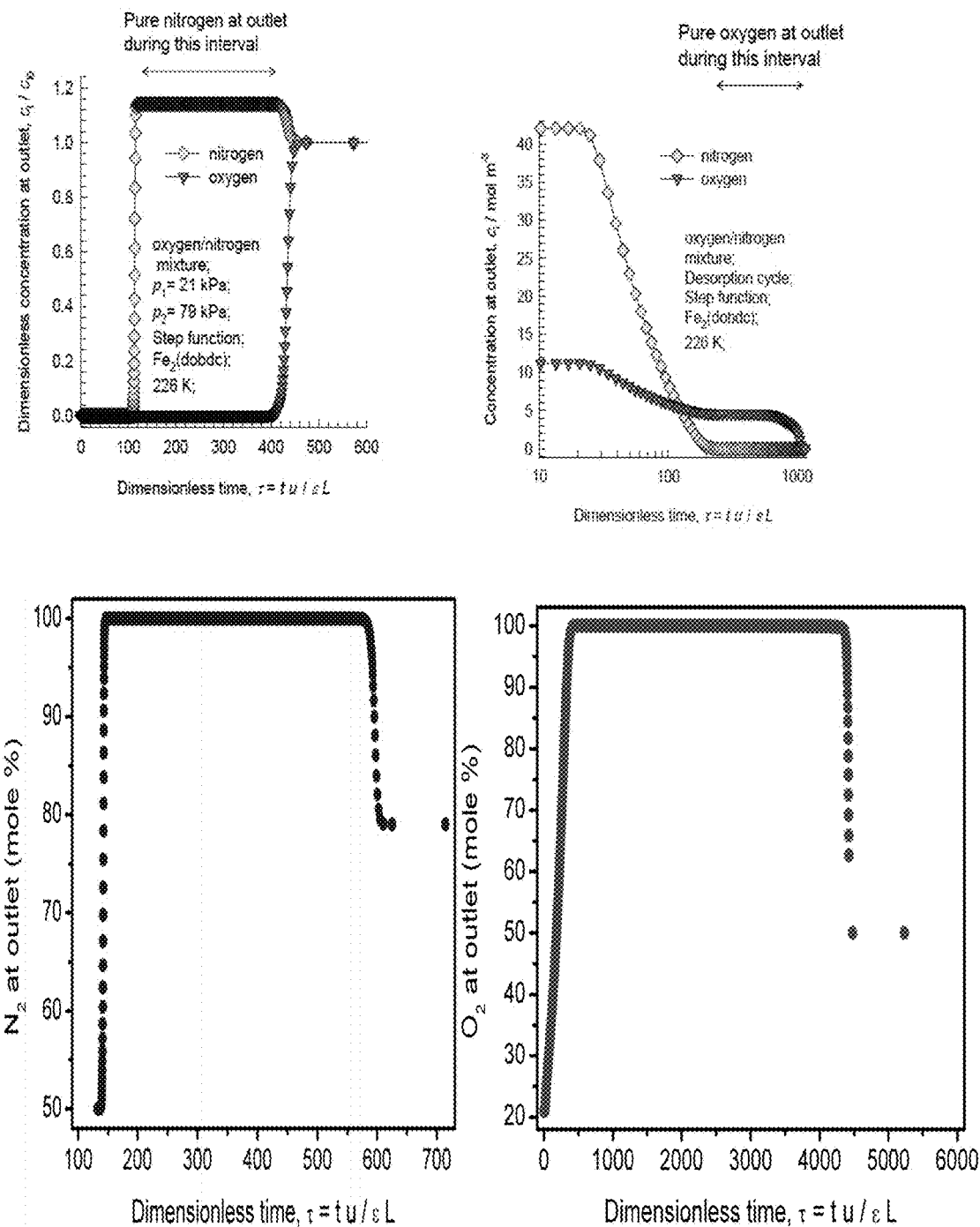
FIG. 19 is a series of graphs showing a calculated $N_2$ adsorption breakthrough curves and calculated O2 desorption breakthrough curves during adsorption/desorption of simulated air by $Fe_2(dobdc)$ at various temperatures.

The high $O_2/N_2$ selectivity, in conjunction with the rapid and reversible cycling times, suggest that $Fe_2$(dobdc) warrants further consideration as an adsorbent for $O_2/N_2$ separations via a modified vacuum-swing adsorption (VSA) process. FIG. 18 is a schematic drawing of VSA apparatus. Here, dry air is flowed over a packed bed of $Fe_2$(dobdc) at temperatures near 210 K, which could potentially offer significant cost and energy savings over current separation technologies that are performed at much lower temperatures. Breakthrough experiments were simulated at 211 and 226 K to evaluate the performance of $Fe_2$(dobdc) for the separation of $O_2$ from $N_2$ at concentrations similar to those present in air (see FIG. 5). FIG. 5 is a graph that shows calculated $N_2$ (diamonds) and $O_2$ (squares) breakthrough curves during adsorption of simulated air ($O_2:N_2=0.21:0.79$) by $Fe_2$(dobdc) at 211 K. The methodology adopted for the breakthrough simulations has been described.[20] The x-axis in FIG. 5 is a dimensionless time, τ, obtained by dividing the actual time, t, by the contact time between the gas and metal-organic framework crystallites, alu. For a given adsorbent, under selected operating conditions, the breakthrough characteristics are uniquely defined by r, allowing the results presented here to be equally applicable to laboratory scale equipment as well as to industrial scale adsorbers. It is apparent from the simulated curves that $N_2$ quickly saturates the sample, as evidenced by the low breakthrough time. The mole % of $N_2$ in the outlet stream as a function of dimensionless time is presented in FIG. 19, which is a calculated $N_2$ breakthrough curve during adsorption of simulated air ($O_2:N_2=0.21:0.79$) by $Fe_2$(dobdc) at 211 K (lower left) and 226 K (upper left). Calculated $O_2$ breakthrough curve during the desorption step of the vacuum-swing adsorption process at 211 K (lower right) and 226 K (upper right). In contrast to currently employed VSA processes, in which $N_2$ is selectively adsorbed on the packed bed while $O_2$ is collected, $Fe_2$(dobdc) would selectively adsorb $O_2$.[21] Accordingly, shortly after $N_2$ breakthrough, the gas stream is pure nitrogen while $O_2$ is retained by the framework. Upon $O_2$ breakthrough, the VSA process is advanced to the second step, in which vacuum is applied to the sample bed. Although the gas at the outlet is initially a mixture of $N_2$ and $O_2$ the concentration of $O_2$ quickly increases to near 100 mole % (see FIG. 19). This results in a large supply of pure $O_2$. After a majority of the $O_2$ is removed from the adsorber, a low-pressure flow of pure $N_2$ would be flowed over the material to fully regenerate the bed for subsequent cycling.

Mössbauer Spectra. The different $O_2$ adsorption behavior at low versus room temperature suggests the existence of two different modes by which $O_2$ binds to the open iron sites in $Fe_2$(dobdc). Mössbauer spectroscopy was employed to probe the electronic structure at the metal center. At all temperatures, the spectra of $Fe_2$(dobdc) in the absence of $O_2$ feature a simple doublet. At 298 K this doublet exhibits an isomer shift of 1.094(3) mm/s and a quadrupole splitting of 2.02(1) mm/s. These values are consistent with high-spin iron(II) in a square pyramidal coordination environment, as established below for the structure of the compound. Upon exposure to $O_2$, a small amount (ca. 5-15%, depending upon temperature) of high-spin iron(II) is still observed, presumably because a small portion of the iron(II) sites remain unoxygenated.

Figure 6:
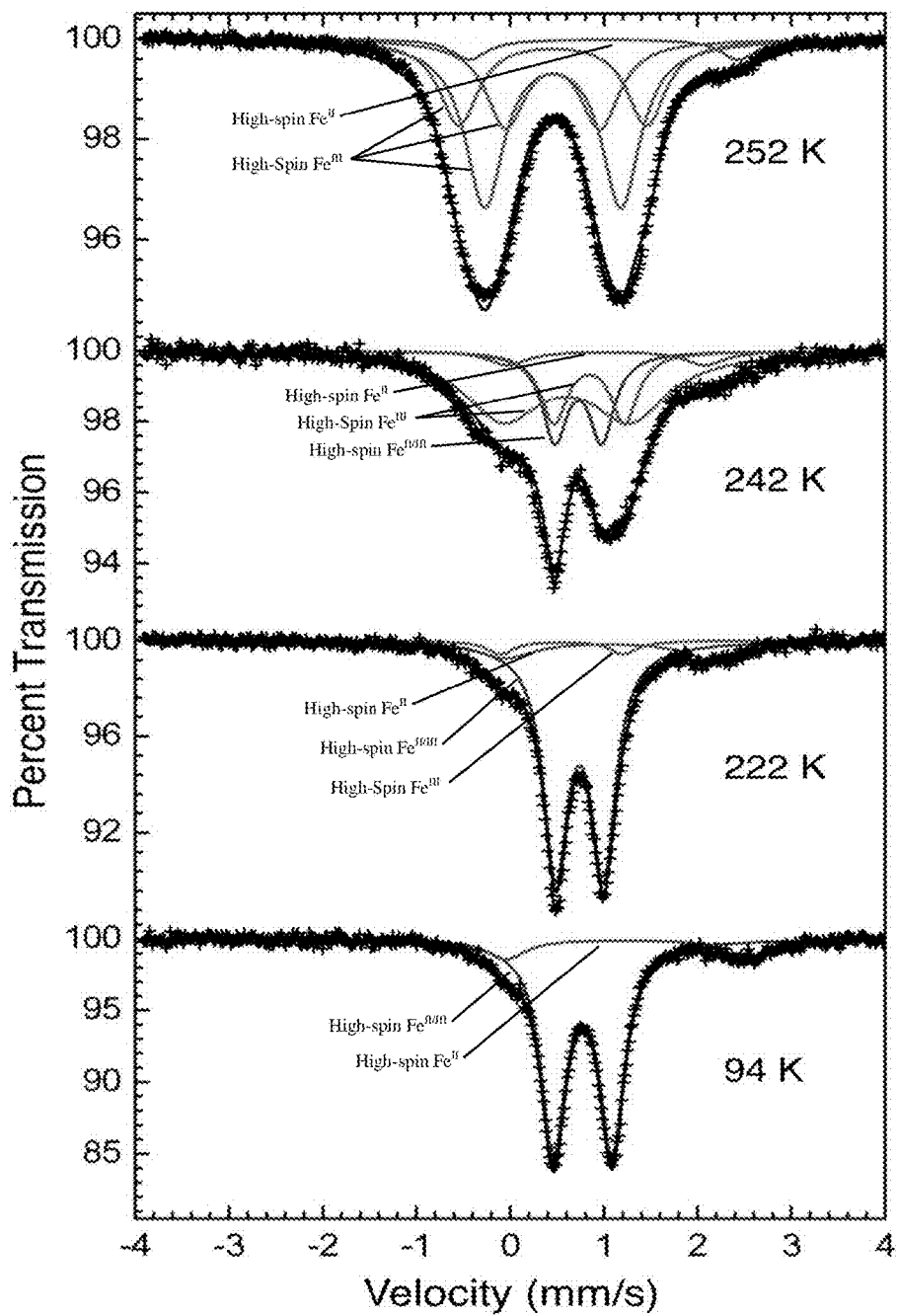
FIG. 6 is a Mössbauer spectra measured between 94 and 252 K for $Fe_2(dobdc)$ in the presence of $O_2$.

FIG. 6 is a Mössbauer spectra measured between 94 and 252 K for $Fe_2$(dobdc) in the presence of $O_2$. As shown in FIG. 6, the spectrum obtained in the presence of $O_2$ at 94 K indicates that almost all of the iron in the sample has a substantially reduced isomer shift that is approximately halfway between those expected for high-spin iron(II) and high-spin iron(III). This suggests a partial transfer of electron density from each of the $Fe^{II}$ centers in the framework to form a weak bond with an $O_2$ species that is somewhere between the neutral molecule and superoxide. Thus, exposure of $Fe_2$(dobdc) to $O_2$ at low temperatures is consistent with the formation of $Fe_2(O_2)_2$(dobdc), featuring one weakly held $O_2$ molecule per iron atom. This is fully consistent with the observation of a reversible adsorption of 18.2 wt % $O_2$ at 211 K. At this point it is not possible to determine from the Mössbauer spectral results whether the electron transfer is static or dynamic, with an electron transfer time that is faster than the ca. $10^{-7}$ s time scale of the iron-57 Mössbauer spectral experiment.

Upon warming to 222 K and above, further changes arise in the Mössbauer spectra, which are clearly indicative of the formation of high-spin iron(III). The temperature at which this change in oxidation state occurs is consistent with the temperature at which we first observe the onset of and irreversible uptake of $O_2$ uptake in gas adsorption experiments (ca. 220 K). The change in oxidation state together with the irreversible uptake of 9 wt % $O_2$ suggest the formation of a compound of formula $Fe_2(O_2)(dobdc)$, in which half of the $Fe^{III}$ centers strongly bind a peroxide anion. Note that, consistent with the presence of at least two different coordination environments, one with $O_2^{2-}$ bound and one without, fitting the spectra requires the use of at least two doublets for the iron(III) components.

Figure 20:
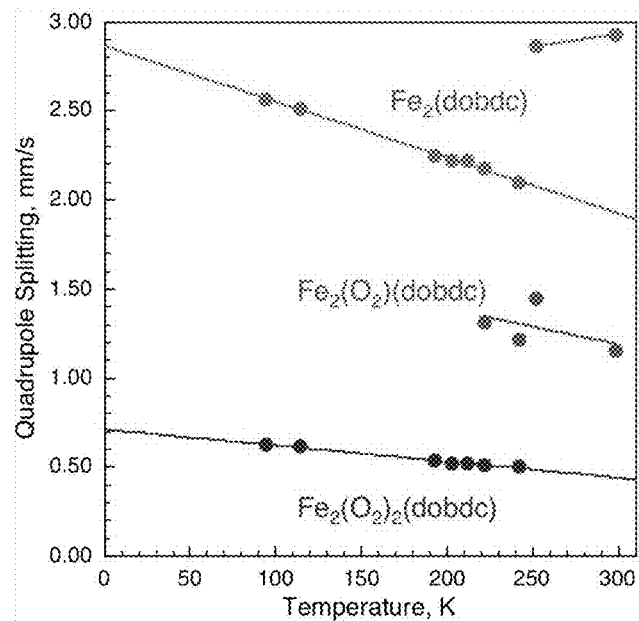
FIG. 20 is graph showing temperature dependence of quadrupole splitting for $Fe_2(dobdc)$, $Fe_2(O_2)_2(dobdc)$, and $Fe_2(O_2)(dobdc)$.
Figure 21:
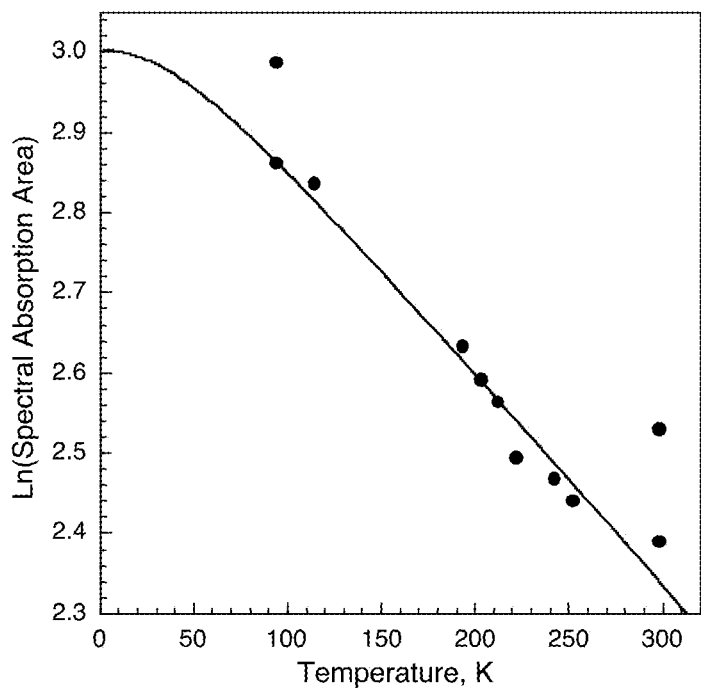
FIG. 21 is a graph showing temperature dependence of the logarithm of the Mössbauer spectral absorption area of $Fe_2(dobdc)$.

The temperature dependence of the quadrupole splitting of main spectral components observed for the framework in the presence of $O_2$, corresponding to the $Fe^{II}$ centers in $Fe_2(dobdc)$, the $Fe^{II/III}$ centers in $Fe_2(O_2)_2(dobdc)$, and the $Fe^{III}$ centers in $Fe_2(O_2)(dobdc)$, is shown in FIG. 20. As expected and in agreement with the Ingalls model,[22] the quadrupole splitting of the square pyramidal high-spin $Fe^{II}$ center in $Fe_2(dobdc)$ decreases the most with increasing temperature, a decrease that results from changes in the electronic population of the $3d_{xy}$, $3_{xz}$, and $M_{yz}$ orbitals, whose degeneracy has been removed by the low-symmetry component of the crystal field. Furthermore, there is a smaller decrease in the splitting upon warming of the other two components. FIG. 21 is a temperature dependence of the logarithm of the Mössbauer spectral absorption area of $Fe_2(dobdc)$. The temperature dependence of the logarithm of the Mössbauer spectral absorption area of $Fe_2(dobdc)$ (see FIG. 21), is well fit with the Debye model for a solid[23] and yields a Debye temperature, $\Theta_D$, of 225(7) K, a value that is reasonable for the compound. Overall, the Mössbauer data point to a situation where, as a sample of $Fe_2(dobdc)$ is warmed under $O_2$, an activation barrier is overcome for the transfer of electrons from two different iron centers to form a bound peroxide anion at every other iron site.

Figure 7:
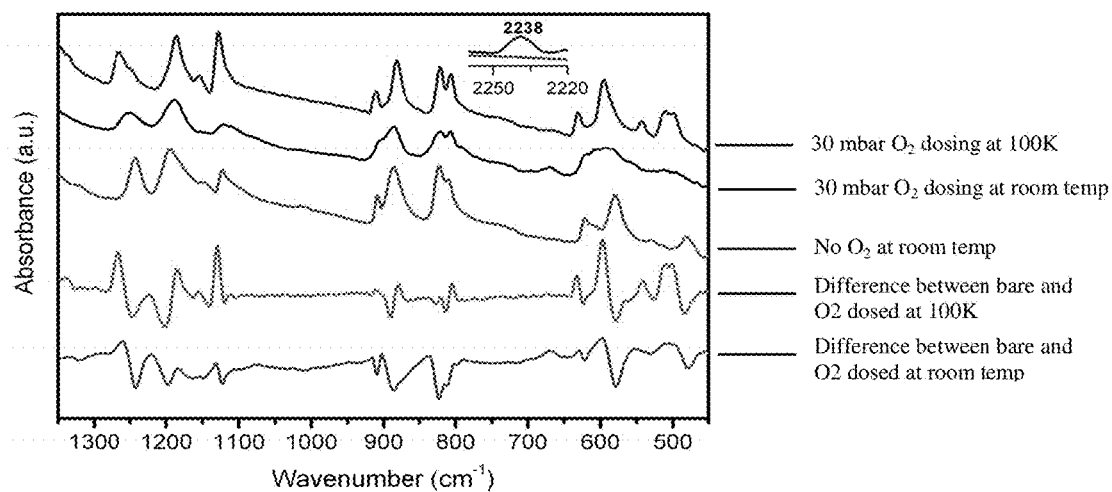
FIG. 7 is an infrared spectra obtained for $Fe_2(dobdc)$ with and without $O_2$ and at various temperatures.

Infrared Spectra. The presence of various $Fe-O_2$ adducts as a function of temperature should also be apparent by infrared spectroscopy. FIG. 7 shows an infrared spectra obtained for $Fe_2(dobdc)$ in the absence of $O_2$ at room temperature, and upon dosing with 30 mbar of $O_2$ at room temperature, and at a low temperature near 100 K. Difference spectra between the bare and $O_2$ dosed materials at low and room temperature are shown. Spectra collected in transmission mode on thin films of $Fe_2(dobdc)$ (see FIG. 7), reveal a number of framework vibrations below 1300 $cm^{-1}$. The reactivity of $Fe_2(dobdc)$ towards $O_2$ was followed at both room temperature and near 100 K. The series of spectra obtained at near 100 K with varying $O_2$ loadings are shown in FIG. 24.

Part (a) of FIG. 24 shows IR spectra of activated $Fe_2$(dobdc); effect of progressive dosage of $O_2$ at low temperature. Maximum coverage 30 mbar. Part (b) of FIG. 24 shows the effect of outgassing at low temperature. It is evident that under these conditions the interaction with oxygen is fully reversible. Bands associated to the superoxo species are clearly visible at 1129, 541 and 511 $cm^{-1}$, while bands originally at 1250, 1198 and at 580 $cm^{-1}$, shift to 1266, 1186 and 595 $cm^{-1}$ respectively. Animation of vibrational modes of $Ni_2(dobdc)$ homologue on optimized structure computed with CRYSTAL code, reveal that all of them are related with the C—O bonds of the linker, being the bands at 1250 at 580 $cm^{-1}$ strongly correlated. [1]

Oxygenation of $Fe_2(dobdc)$ at low temperature gives rise to the spectrum indicated in FIG. 7, and the most relevant changes are evident in the difference spectrum shown in magenta. New bands are seen at 1129, 541, and 511 $cm^{-1}$, while significant shifts are seen in the frameworks bands originally at 1250, 1198, and 580 $cm^{-1}$ (causing negative components in the difference spectrum). The component at 1129 $cm^{-1}$ is assigned to $\nu$(O—O) of a partially-reduced (near superoxo) $O_2$ species coordinated to $Fe^{II/III}$ sites. The first overtone for this stretching mode is also clearly visible at 2238 $cm^{-1}$. The band at 541 $cm^{-1}$ is associated with the Fe—$O_2$ vibration of the of this species, whereas the band at 511 $cm^{-1}$ is attributed to an Fe—$O_{linker}$ mode of the framework, reflecting the $O_2$ adsorption induced modification in Fe.$O_{linker}$ bonds.[24] The interaction with $O_2$ at low temperature is completely reversible by applying vacuum to the sample cell.

Oxygenation of $Fe_2(dobdc)$ at room temperature gives rise to the spectrum indicated in FIG. 7, which can be explained in terms of the formation of a peroxo species coordinated to $Fe^{III}$ centers.[25] The main features in this case are a peak at 790 $cm^{-1}$, due to a $\nu$(O—O) vibrational mode, and a pair of peaks at 697 and 670 $cm^{-1}$, arising from the peroxo ring modes of the Fe-($\eta^2$-$O_2$) unit. The peaks at 550 $cm^{-1}$ and 507 $cm^{-1}$ are further assigned to the $\nu_{asym}$ and $\nu_{sym}$ modes of the iron-oxygen bond of the peroxo species.

Figure 25:
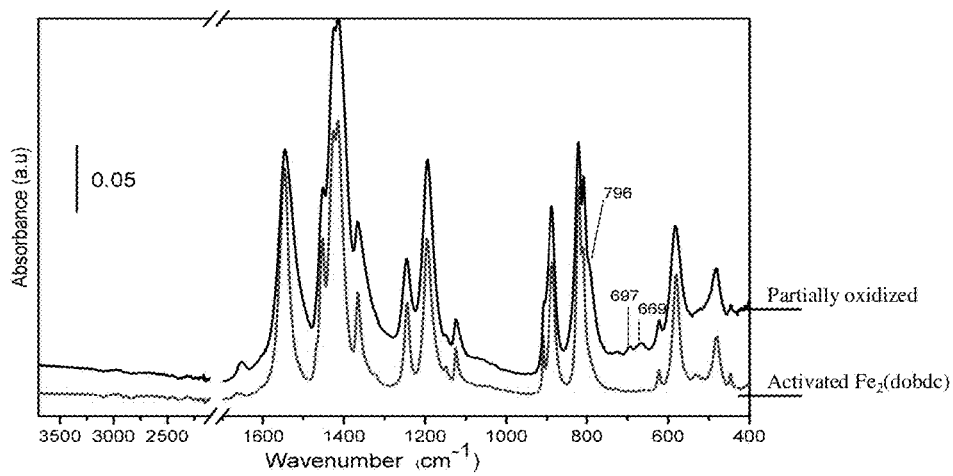
FIG. 25 is an ATR spectra of activated $Fe_2(dobdc)$ and a partially oxidized sample.

Similar features are more clearly visible in the ATR spectrum of an oxidized sample (see FIG. 25). FIG. 25 is an ATR spectra of activated $Fe_2(dobdc)$ and of a partially oxidized sample. The spectra were collected inside a $N_2$ filled glove box. Bands due to peroxo species are clearly visible at 796, 697 and 669 $cm^{-1}$, confirming the data obtained in transmission mode on the sample carefully reacted at room temperature (see FIG. 7).

Figure 26:
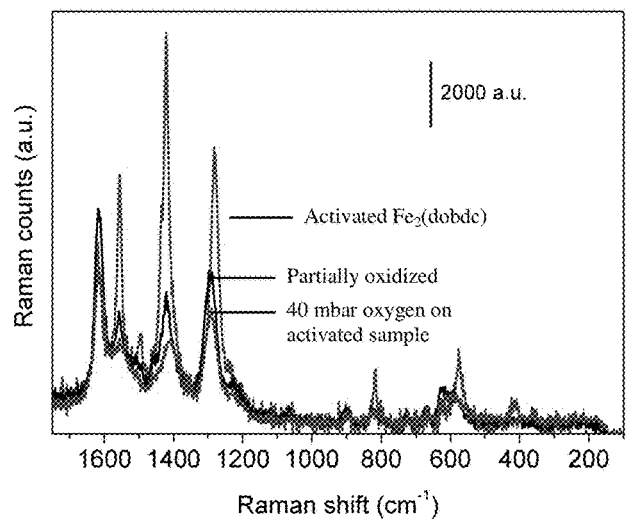
FIG. 26 is series of Raman spectra of activated $Fe_2(dobdc)$, a partially oxidized sample, and an activated sample subject to 40 mbar of oxygen.

Small changes are also visible in the Raman spectrum of the sample upon $O_2$ interaction (see FIG. 26). FIG. 26 is a Raman spectra collected with 512 nm laser at 5% of power on sample in a cell cooled by liquid nitrogen. Spectra of activated $Fe_2(dobdc)$; partially oxidized sample; effect of 40 mbar of oxygen on activated sample. Raman spectra have been collected on the sample cooled with a liquid nitrogen flux in order to reduce the laser damaging effects. In this case a band at 630 $cm^{-1}$ is the most evident feature of the formation of a peroxo species. Smaller bands at 674 and 729 are also visible [2,3].

Overall, the vibrational spectra are fully consistent with the model already developed from interpretation of the $O_2$ adsorption data and Mössbauer spectra.

Figure 8:
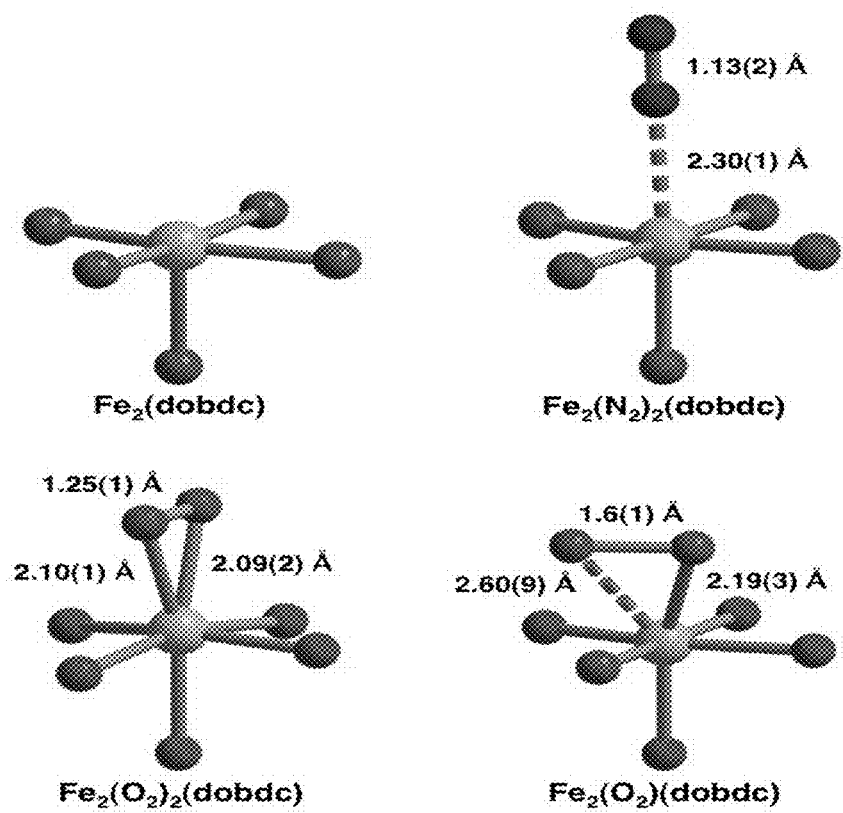
FIG. 8 is a series of graphical representations of a first coordination spheres for the iron centers within $Fe_2(dobdc)$ and its $O_2$ and $N_2$ dosed variants, dosed at various temperatures.

Structures via Neutron Powder Diffraction. Powder neutron diffraction data provide direct structural details of the means by which $O_2$ and $N_2$ interact with $Fe_2(dobdc)$ (see FIG. 8). FIG. 8 shows a first coordination spheres for the iron centers within $Fe_2(dobdc)$ and its $O_2$ and $N_2$ dosed variants, as determined from Rietveld analysis of neutron powder diffraction data. The structures depicted are for samples under vacuum (upper left), dosed with $N_2$ at 100 K (upper right), dosed with $O_2$ at 100 K (lower left), and dosed with $O_2$ at 298 K (lower right). All diffraction data were collected below 10 K. Values in parentheses give the estimated standard deviation in the final digit of the number. Initial data collected on an evacuated sample of $Fe_2(dobdc)$ confirm the presence of accessible $Fe^{II}$ sites with a square pyramidal coordination environment. Here, each iron center is coordinated by O donor atoms from two aryloxide units (located at the front right and back left basal positions) and three carboxylate groups (at the remaining positions) from surrounding dobdc$^{4-}$ ligands. Note that the arrangement of framework O donor atoms is the same in each depiction shown in FIG. 8.

Figure 27:
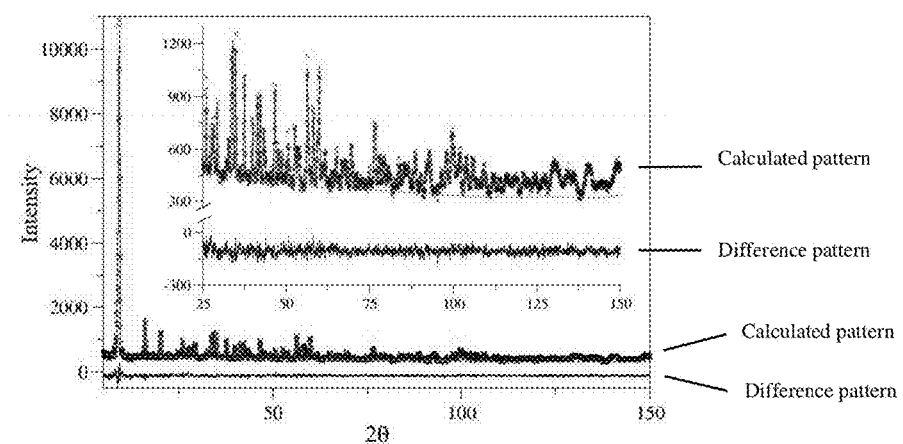
FIG. 27 is Rietveld refinement of the experimental neutron diffraction pattern of $Fe_2(dobdc)$ exposed to $O_2$ at 100K.

FIG. 27 is Rietveld refinement of the experimental neutron diffraction pattern of Fe$_2$(dobdc) exposed to O$_2$ at 100K. The calculated pattern is in good agreement with the experimental data (crosses) as evidenced by the difference pattern. A Rietveld refinement was performed against data collected for a sample of Fe$_2$(dobdc) that was cooled to 100 K, dosed with two equiv of O$_2$ per iron, and then cooled to 4 K (see FIG. 27). Three different O$_2$ adsorption sites are evident in the resulting model. The highest occupancy site, with a refined occupancy of 0.917(8) O$_2$ molecules per iron, is located at the open iron coordination position. Significantly, the O$_2$ molecule binds in a symmetric side-on coordination mode, with Fe—O distances of 2.09(2) and 2.10(1) Å. The O—O separation of 1.25(1) Å lies between the internuclear distances observed for free O$_2$ (1.2071(1) Å)[26] and typical of an O$_2^-$ superoxide unit (1.28 Å).[4] This again is consistent with only partial reduction of O$_2$ under these conditions. Although symmetric side-on coordination of superoxide and peroxide to other transition metals has been reported[27] this represents, to the best of our knowledge, the first crystallographic evidence of non-bridging side-on binding of any dioxygen species to iron in a non-enzyme system.[28] The second and third O$_2$ adsorption sites, with occupancies of 0.857(9) and 0.194(8), respectively, occur in the pores of the framework at distances of greater than 3 Å from the iron center and organic linker (see FIG. 28), indicating weak dispersive type interactions between the adsorbate and the framework walls.

Figure 28:
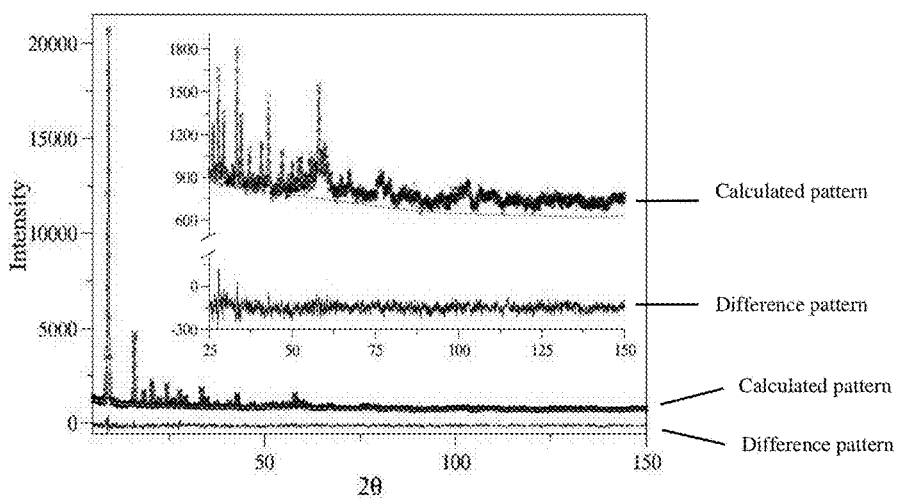
FIG. 28 is Rietveld refinement of the experimental neutron diffraction pattern of $Fe_2(dobdc)$ exposed to $O_2$ at 298K.

FIG. 28 is Rietveld refinement of the experimental neutron diffraction pattern of Fe$_2$(dobdc) exposed to O$_2$ at 298K. The calculated pattern is in good agreement with the experimental data (crosses) as evidenced by the difference pattern.

Figure 29:
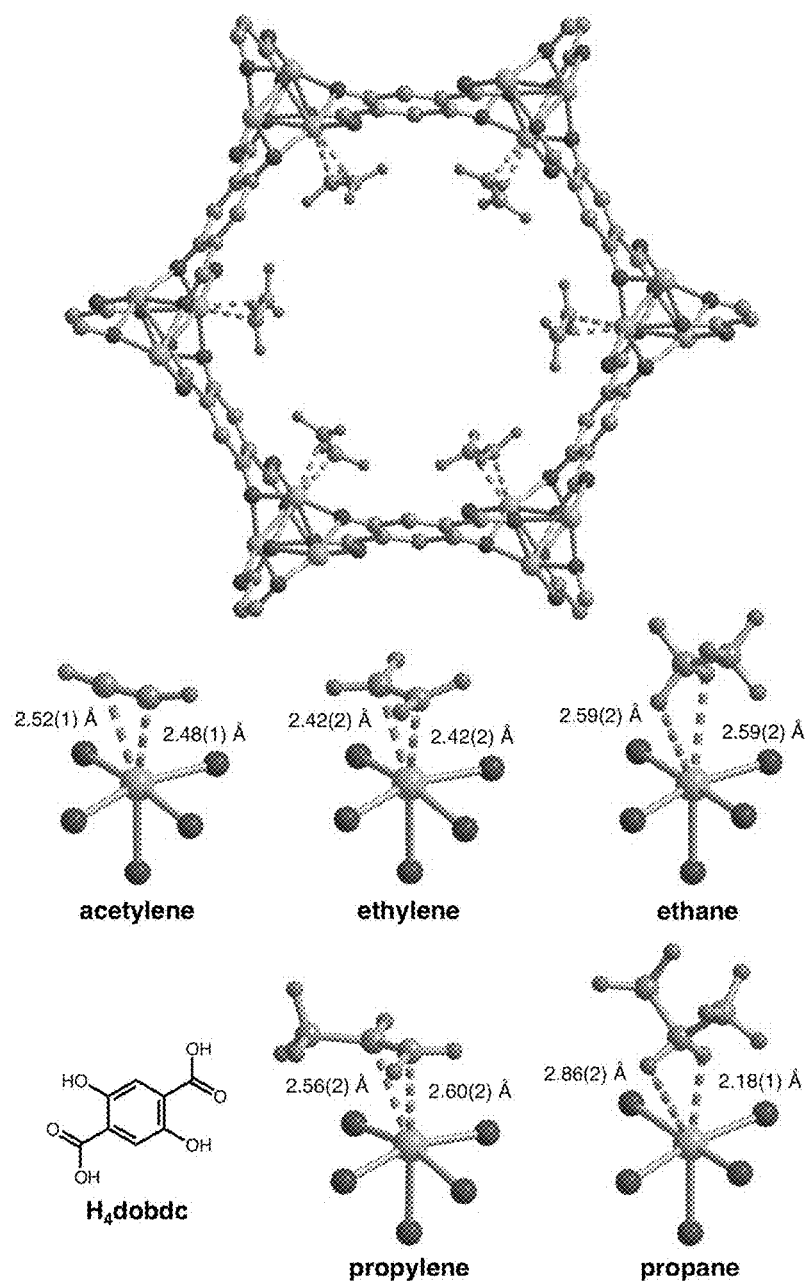
FIG. 29 shows, at the top, a graphical representation of a structure of $Fe_2(O_2)_2(dobdc)$-$2O_2$ as viewed down the (001) direction. At the bottom are an $H_4(dobdc)$ ligand and the first coordination spheres for the iron centers in the solid state structures obtained upon dosing $Fe_2(dobdc)$ with acetylene, ethylene, ethane, propylene, and propane.

FIG. 29 shows a structure of Fe$_2$(O$_2$)$_2$(dobdc)-2O$_2$ as viewed down the (001) direction. (H atoms have been omitted for clarity.) There is an ethylene molecule bound to the open coordination site at each iron(II) center. At the bottom are an H$_4$(dobdc) ligand and the first coordination spheres for the iron centers in the solid state structures obtained upon dosing Fe$_2$(dobdc) with acetylene, ethylene, ethane, propylene, and propane. Note that for propane in Fe$_2$(dobdc) the adsorbed hydrocarbon molecule has orientational disorder with respect to the open metal center. Of several refined models, the single-molecule with large displacement parameters is the most reasonable.

Rietveld refinement performed against data collected on a sample of Fe$_2$(dobdc) that had been dosed with an excess of O$_2$ at room temperature, evacuated, and subsequently cooled to 4 K was also performed (see FIG. 29). The data were best fit by a model in which O$_2$ is coordinated to iron in an asymmetric side-on mode and at a refined occupancy of 0.46(2). The model indicates substantial elongation of the O—O distance to 1.6(1) Å, consistent with a two-electron reduction of O$_2$ to peroxide. With an Fe—O$_2$ centroid distance of 2.26(1) Å, the peroxide unit also appears to have slipped substantially towards one of the bridging ligands. This type of coordination of peroxide has been observed previously in naphthalene dioxygenase[28a] and has also been proposed based upon spectroscopic evidence for a number of non-heme iron complexes.[29]

Neutron powder diffraction data were further collected on a sample of Fe$_2$(dobdc) dosed with 0.5, 1.0, and 2.0 equiv of N$_2$ dosed at 80 K. Upon dosing with approximately 0.5 equiv of N$_2$, a binding site at the metal center is apparent with an occupancy of 0.641(5). Nitrogen coordinates end on with an Fe—N—N angle of 179(1)° and an Fe—N distance of 2.30(1) Å. The N—N distance of 1.133(15) Å is slightly longer than the N—N distance of free nitrogen (1.0977(1) Å).[30] Additional N$_2$ uptake reveals a second site that runs more parallel to the pore walls, with N . . . O contacts between 3.4 and 3.6 Å. The close N$_2$-framework interactions are the origins of the relatively high enthalpy for adsorption. The metal-specific interactions, however, are clearly much weaker than for O$_2$, which results in interaction of both atoms with the metal, electron transfer, and a significant compression of the unit cell upon adsorption (see FIG. 48). FIG. 48 shows a table of unit cell lengths and volumes.

The differences in how O$_2$ binds to iron within Fe$_2$(dobdc) at low versus high temperatures suggests that the framework undergoes electron transfer processes similar to those reported for nonheme iron-containing enzymes.[31] In these systems, O$_2$ typically progresses through a number of electron transfer steps starting with superoxo and peroxo. In the case of Fe$_2$(dobdc) at low temperature, each iron shares one of its electrons with a single O$_2$ molecule, resulting in oxidation of all of the metal centers to an intermediate iron(II/III) oxidation state. This charge transfer is reversible at low temperatures and accounts for the high gas uptake demonstrated in the gas adsorption experiments. However, at elevated temperatures two electrons are transferred to the adsorbing O$_2$ molecule, the first presumably being shared in a manner analogous to what occurs at low temperature, and the second subsequently arriving from an adjacent iron center by promotion over an activation barrier via the available thermal energy. In this scenario, all of the metal centers within the framework are converted to iron(III), half of which are coordinated irreversibly to a peroxide anion, while the other half remain five-coordinate.

The foregoing results demonstrate the ability of Fe$_2$(dobdc) to selectively bind O$_2$ over N$_2$ via electron transfer interactions. Breakthrough curves calculated using single-component gas adsorption isotherms and ideal adsorbed solution theory indicate that the material should be capable of the high-capacity separation of O$_2$ from air at temperatures as high as 226 K. This is substantially higher than the cryogenic temperatures currently used to separate O$_2$ from air on a large scale. At still greater temperatures, a thermal activation barrier to the formation of iron(III)-peroxide species is overcome and desorption of O$_2$ is no longer possible. Efforts are underway to synthesize related metal-organic frameworks with an increased activation barrier for the formation of peroxide, thereby generating a high-capacity O$_2$ separation material that can operate closer to ambient temperatures.

In addition, the efficacy of the new redox-active framework in performing a variety of other gas separations where charge transfer might also lead to selectivity. Additional example separations include, but are not limited to, paraffin/olefin separations, carbon monoxide removal, acetylene storage, and nitric oxide/nitrous oxide separations.

Figure 9:
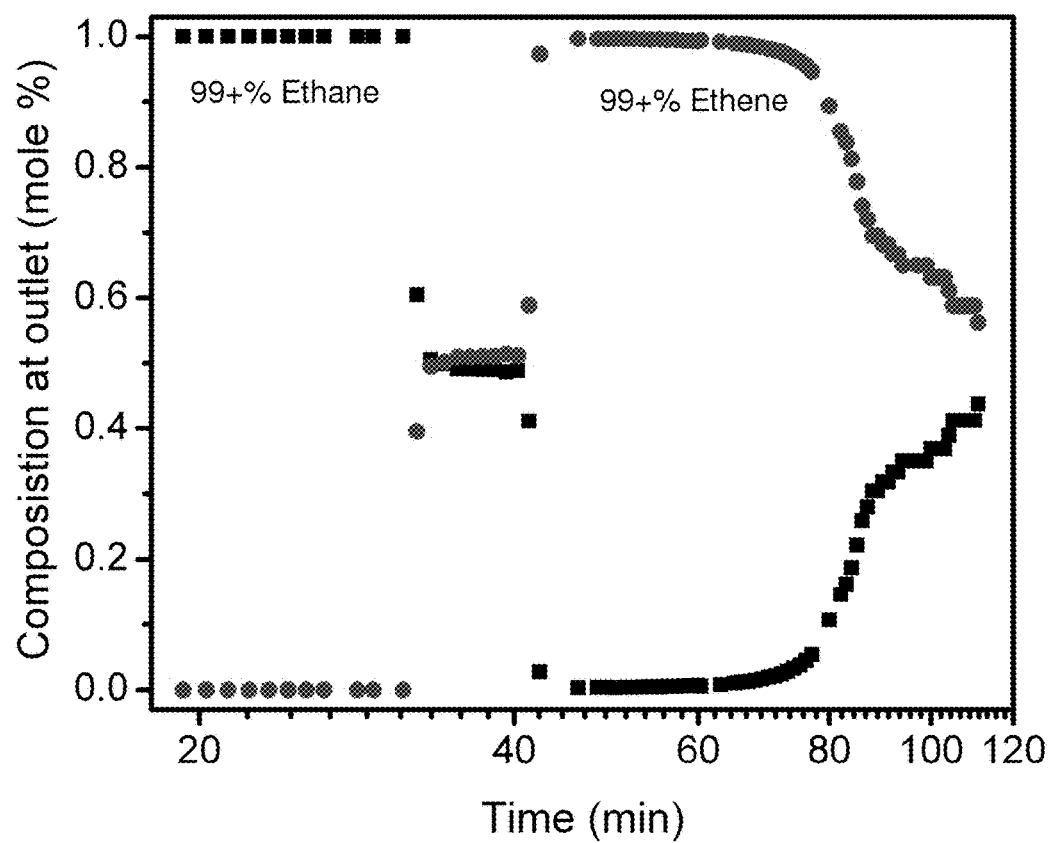
FIG. 9 is a graph showing the separation of a mixture of ethane and ethane.

FIG. 9 is a graph showing the separation of a mixture of ethane and ethane. A 50/50 mixture of ethane and ethene is flowed through Fe$_2$(dobdc) at 318 K. The framework adsorbs ethene first, supplying greater than 99.5% purity ethane. After ethene "breaks through" gas feed is turned off to supply greater than 99% purity ethene.

Figure 10:
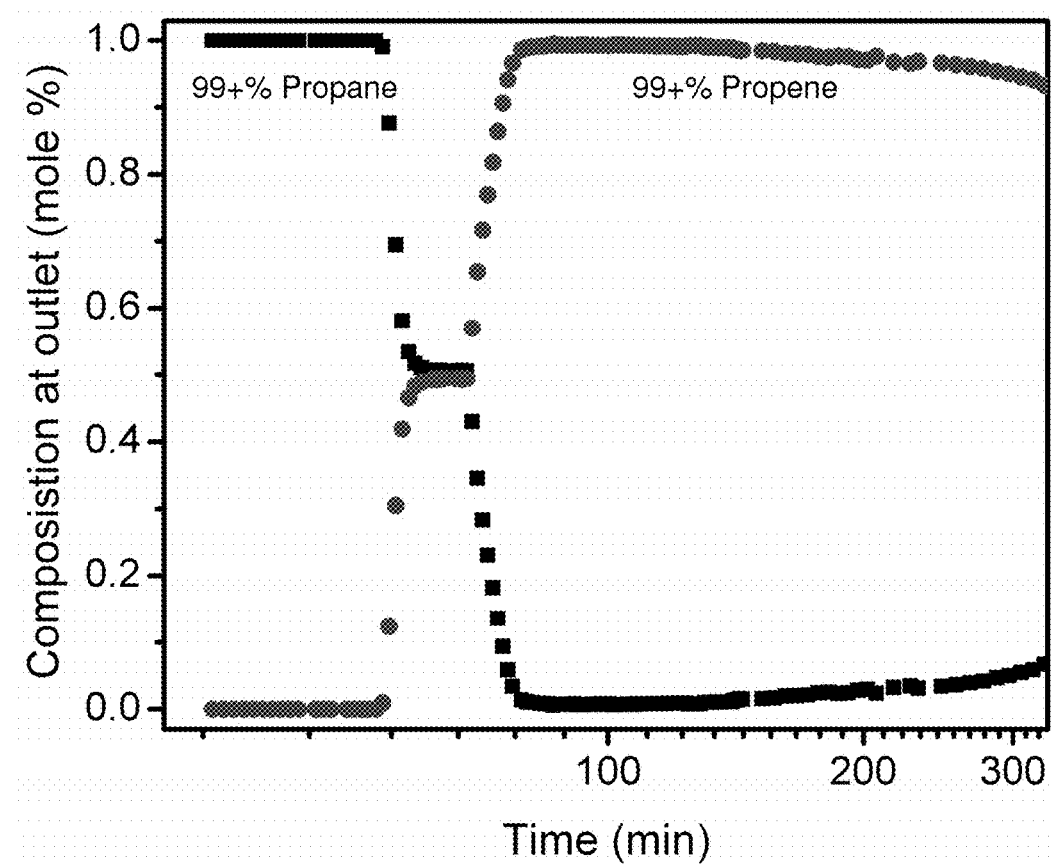
FIG. 10 is a graph showing the separation of a mixture of propane and propene.

FIG. 10 is a graph showing the separation of a mixture of propane and propene. A 50/50 Mixture of propane and propene is flowed through Fe$_2$(dobdc) at 318 K. The framework adsorbs propene first, supplying greater than 99.5% purity propane. After propene "breaks through" gas feed is turned off to supply greater than 99% purity propene.

Figure 30:
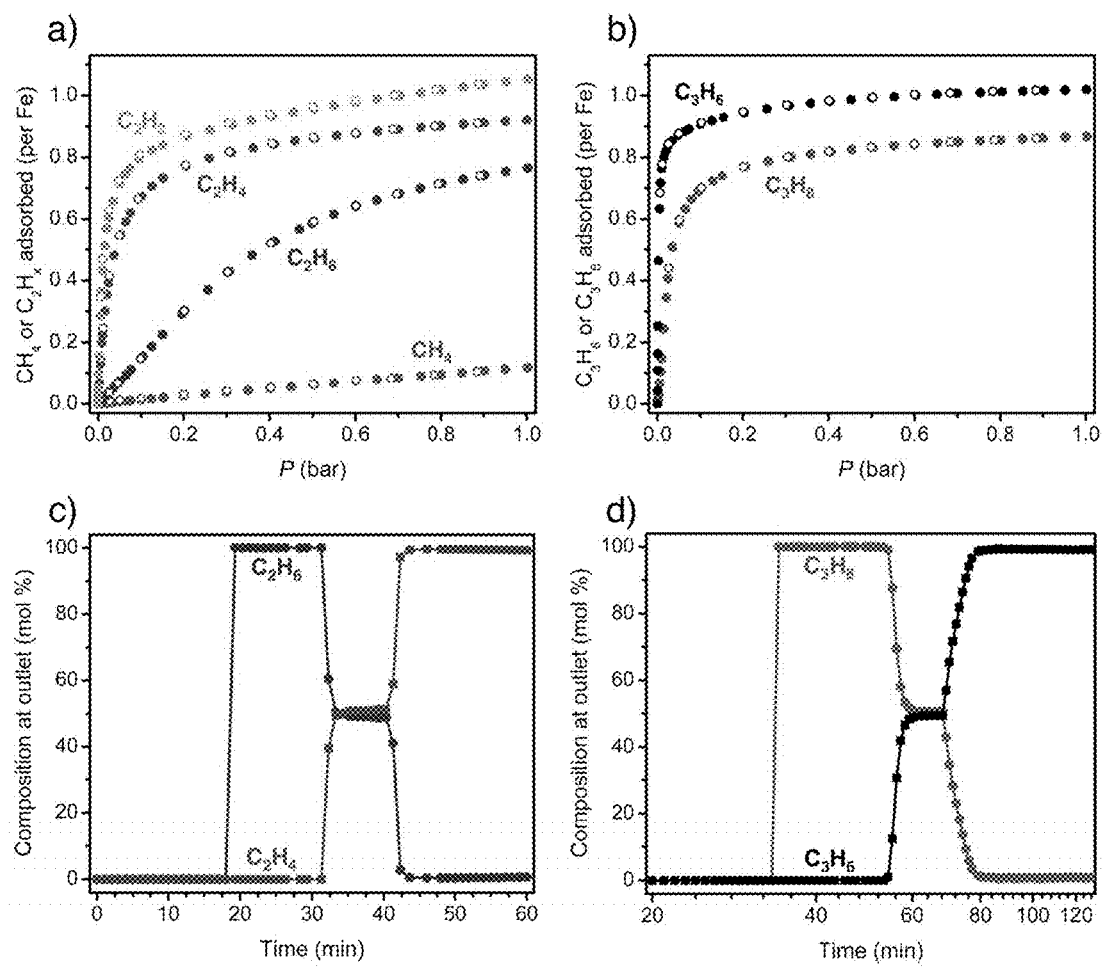
FIG. 30 is a series of graphs, the top row of which are gas adsorption isotherms for methane, ethane, ethylene, and acetylene (a) and for propane and propylene (b) in $Fe_2(dobdc)$ at 318 K, and the bottom row of which are experimental breakthrough curves for the adsorption of equimolar ethane/ethylene (c) and propane/propylene (d) mixtures flowing through $Fe_2(dobdc)$.

To investigate the ability of Fe$_2$(dobdc) to adsorb light hydrocarbons, pure component equilibrium adsorption isotherms for methane, ethane, ethylene, acetylene, propane and propylene were measured at 318, 333, and 353 K. FIG. 30 shows the data obtained at 318 K, with the remaining date presented in FIG. 11. FIGS. 30 (a) and (b) show gas adsorption isotherms for methane, ethane, ethylene, and acetylene (a) and for propane and propylene (b) in Fe$_2$(dobdc) at 318 K. Filled and open circles represent adsorption and desorption data, respectively. The adsorption capacities at 1 bar correspond to 0.77, 5.00, 6.02, 6.89, 5.67, and 6.66 mmol/g, respectively. FIGS. 26 (c) and (d) are experimental breakthrough curves for the adsorption of equimolar ethane/ethylene (c) and propane/propylene (d) mixtures flowing through a 1.5 mL bed of Fe$_2$(dobdc) at 318 K with a total gas flow of 2 mL/minute at atmospheric pressure. After breakthrough of the olefin and return to an equimolar mixture composition, a nitrogen purge was applied, leading to desorption of the olefin. Note that in an actual separation scenario, desorption would instead be carried out by applying a vacuum and/or raising the temperature. As evidenced by the initial steep rise in the isotherms, Fe$_2$(dobdc) displays a strong affinity for the unsaturated hydrocarbons acetylene, ethylene, and propylene. Additionally, the uptake of these gases at 1 bar approaches the stoichiometric quantity expected if one gas molecule is adsorbed per iron (II) center. The propane and ethane adsorption capacities under these conditions, though lower than those of their unsaturated counterparts, are both significantly higher than observed for methane, which has lower polarizability and a smaller kinetic diameter. Importantly, all of the isotherms are completely reversible and exhibit no hysteresis. Further, equilibrium adsorption experiments at 318K (FIG. 12) indicate no loss in olefin uptake capacity after 15 ethylene adsorption/desorption cycles. Additionally, no loss in propylene uptake was observed after 40 adsorption/desorption cycles as verified by thermogravimetric analysis (FIG. 12).

Powder neutron diffraction experiments were carried out to determine the nature of the interactions of these adsorbate molecules within Fe$_2$(dobdc). In a typical experiment, Fe$_2$(dobdc) was dosed with deuterated gas at 100 K and cooled to 4 K for data collection. Rietveld refinements were performed agains these data to provide the structural models presented in FIG. 28. Analogous to the results obtained investigating the coordination of dioxygen to the iron centers of this material, only one adsorption site is apparent. This site corresponds to the open coordination site of the exposed Fe$^{2+}$ cations, upon dosing sub-stoichiometric equivalents of gas per framework iron. The unsaturated hydrocarbons, acetylene, ethylene, and propylene, display the anticipated side-on binding modes, with Fe—C distances lying in the range 2.42(2) to 2.60(2) Å. These distances are substantially longer than the separations of 2.020(5) to 2.60(2) Å observed for the diamagnetic complex [Fe(C$_2$H$_4$)$_4$]$^2$, one of the very few iron(II)-olefin species to be structurally characterized previously. The difference suggests that the metal centers within Fe$_2$(dobdc) maintain a high-spin electron configuration when binding these gases, consistent with weaker interactions that can be reversed with little energy penalty. The interactions of both ethane and propane with the metal cations in Fe$_2$(dobdc) are weaker, as evidenced by the elongated Fe—C distance of approximately 3 Å. This is in good agreement with the Mg—C distance reported for methane adsorption in Mg$_2$(dobdc), a system in which the metal-adsorbate interactions are also a result of ion-induced dipole interactions between coordinatively-unsaturated metal cations and hydrocarbon deuterium atoms.

The strength of the hydrocarbon binding with Fe$_2$(dobdc) was determined quantitatively through analysis of the gas adsorption data. The data for acetylene, ethylene, ethane, propane, and propylene, expressed in terms of absolute loadings, were fitted with the dual-Langmuir-Freundlich isotherm model, whereas methane adsorption data were fitted with a single-site Langmuir model. Isosteric heats of adsorption were calculated form the fits to compare the binding enthalpies of these gases under various loadings (see FIG. 13). Heats of adsorption for acetylene (−47 kJ/mol), ethylene (−45 kJ/mol), and propylene (−44 kJ/mol) show a significant reduction as the loading approaches the value corresponding to one gas molecule per iron(II) center, again consistent with the exposed metal cations presenting the strongest adsorption sites in the material. Propane (−33 kJ/mol), ethane (−25 kJ/mol), and methane (−20 kJ/mol) adsorption enthalpies are all considerably lower in magnitude, with the trend reflecting the decreasing polarizabilities of these molecules from propane to ethane to methane.

Figure 31:
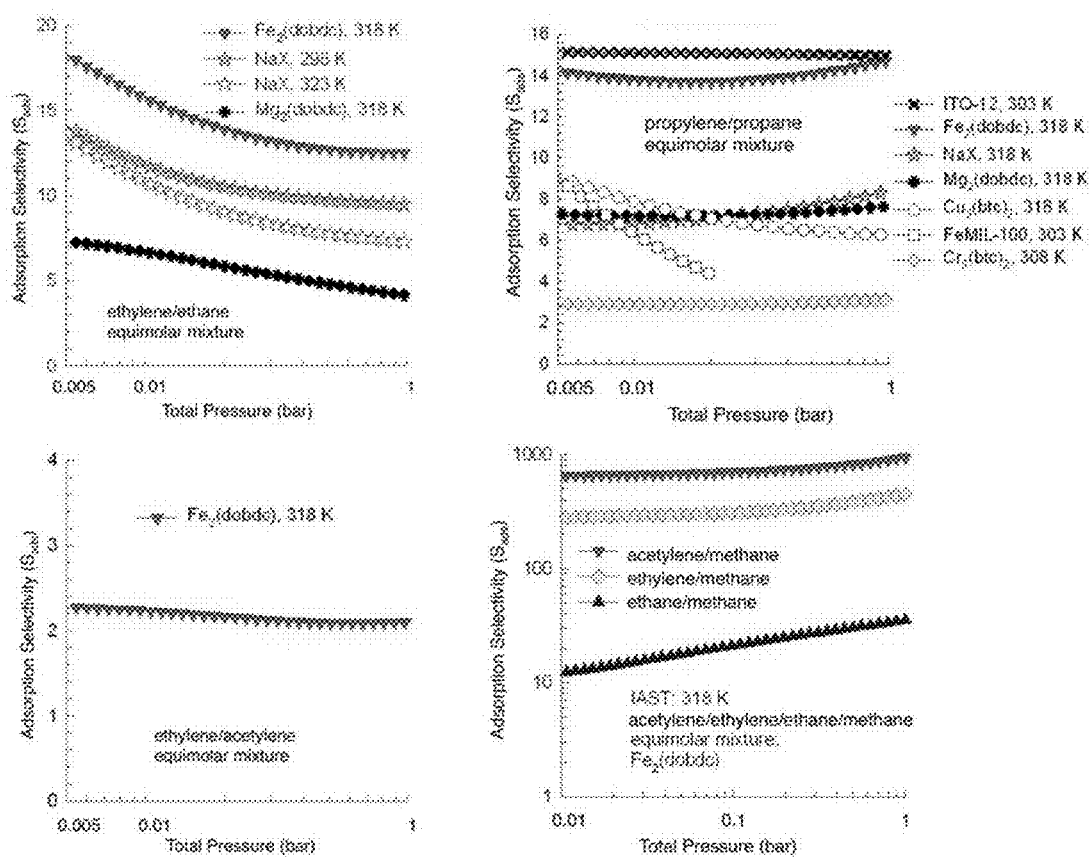
FIG. 31 is a series of graphs showing calculations of the adsorption selectivity for ethane/ethylene (upper left), propane/propylene (upper right), acetylene/ethylene (lower left) and acetylene/methane, ethylene/methane, ethane/methane (lower right) in $Fe_2(dobdc)$ at 318 K.

Adsorption selectivities were calculated using ideal adsorbed solution theory (IAST) using the fitted isotherms of the experimental isotherm data for relevant gas mixtures in Fe$_2$(dobdc) and a number of other porous material for which analogous gas uptake properties have been reported (see FIG. 31). FIG. 31 shows calculations of the adsorption selectivity, $S_{ads}$, using Ideal Adsorbed Solution Theory for ethane/ethylene (upper left), propane/propylene (upper right), acetylene/ethylene (lower left) and acetylene/methane, ethylene/methane, ethane/methane (lower right) in Fe$_2$(dobdc) at 318 K. For the equimolar mixture of ethylene and ethane at 318 K, the adsorption selectivities obtained for Fe$_2$(dobdc) are significantly greater than those calculated for either zeolite NaX or the isostructural metal-organic framework Mg$_2$(dobdc), which display seletvities of 9-14 and 4-7, respectively. The latter result is consistent with the softer character of Fe$^{2+}$ relative to Mg$^{2+}$, leading to a stronger interaction with the π electron cloud of the olefin. Similarly, in comparing the performance of Fe$_2$(dobdc) with other porous materials for the separation of a propane/propylene mixture (selectivity=13-15), it is rivaled in selectivity only by zeolite ITQ-12 which displays adsorption selectivity of 15 while the other materials display selectivities from 3-9. Note, however, that the selectivities of ITQ-12 for this mixture were calculated from data collected at 303 K, and it is expected that selectivity of this material will be lower at higher temperatures. Adsorption selectivities were also calculated using LAST for Fe$_2$(dobdc) in an equimolar four-component mixture of methane, ethane, ethylene, and acetylene at 318 K, as relating to the purification of natural gas. For an adsorption-based process operating at 1 bar, the calculated acetylene/methane, ethylene/methane, and ethane/methane selectivities are 700, 300, and 20, respectively. These values are much higher than those recently reported (13.8, 11.1, and 16.6, respectively) for a zinc-based metal-organic framework, also based on an analogous calculation procedure.

Figure 32:
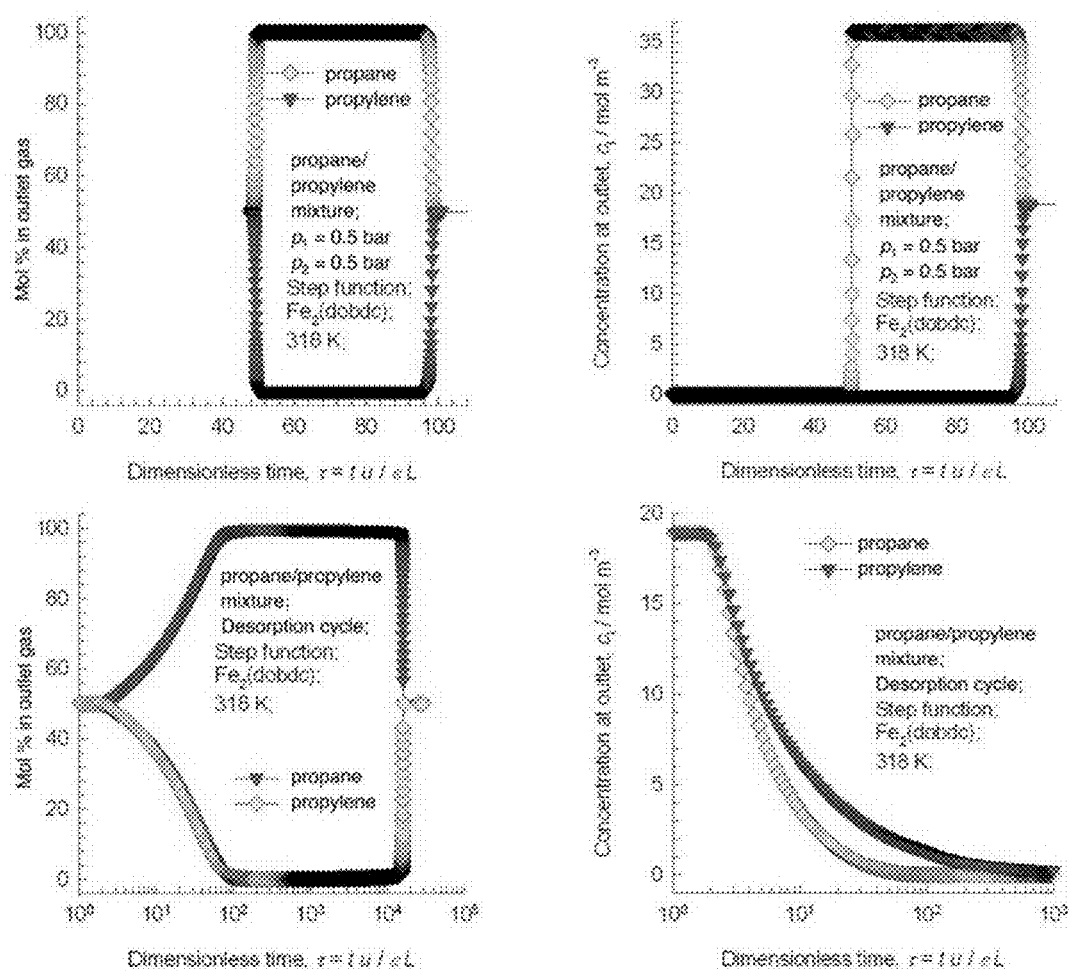
FIG. 32 is a series of curves showing mol % (left) and concentration (right) of propane and propylene during adsorption (upper) and desorption (lower) of a simulated breakthrough experiment.
Figure 33:
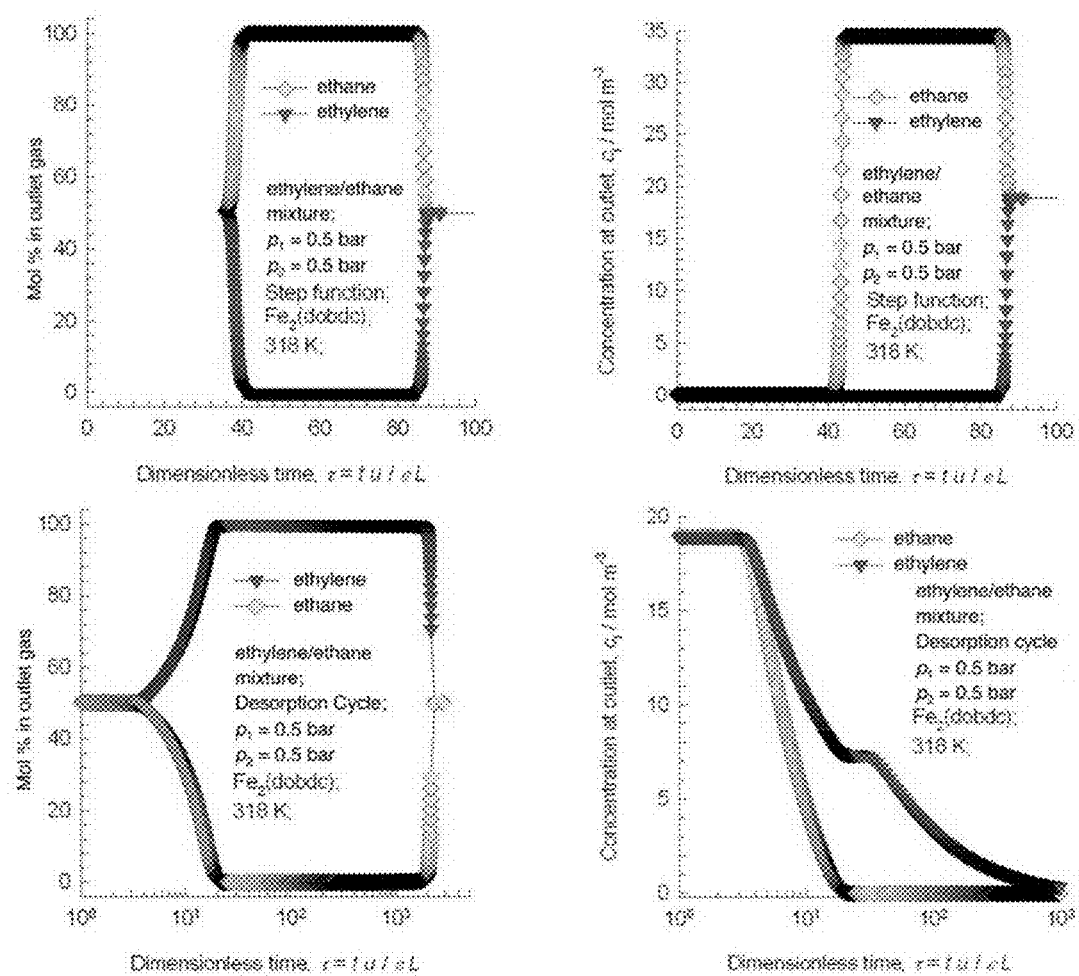
FIG. 33 is a series of curves showing mol % (left) and concentration (right) of ethane and ethylene during adsorption (upper) and desorption (lower) of a simulated breakthrough experiment.

To evaluate performance of Fe$_2$(dobdc) in an actual adsorption-based separation process, breakthrough experiments were performed in which an equimolar ethylene/ethane or propylene/propane mixture was flowed over a packed bed of the solid with a total flow of 2 mL per minute at 318 K (see FIG. 32 and FIG. 33). FIG. 32 is curves showing mol % (left) and concentration (right) of propane and propylene during adsorption (upper) and desorption (lower) of a simulated breakthrough experiment. FIG. 29 is curves showing mol % (left) and concentration (right) of ethane and ethylene during adsorption (upper) and desorption (lower) of a simulated breakthrough experiment. In a typical experiment, the gas mixture was flowed through 300 to 400 mg of metal-organic framework crystallites packed into 1.5 mL glass column, and the outlet gas stream was monitored by a gas chromatograph equipped with a flame ionization detector. As expected from the calculated selectivities, in each case, the alkane was first to elute through the bed, while the solid adsorbent retained the olefin. For the $C_3$ hydrocarbons, the outlet gas contained undetectable levels of propylene, resulting in a propane feed that appeared to be 100% pure, within the detection limit of the instrument (~100 ppm). Upon saturation of the metal centers within the adsorbent, propylene "broke through" and the outlet gas stream then quickly reached equimolar concentrations. By stopping the gas feed and flowing a purge of nitrogen through the bed, the small amount of weakly bound propane remaining in the pores of the framework could be quickly removed, while the iron-bound propylene then desorbed more slowly. Greater than 99% pure propylene was realized during the desorption step of the breakthrough experiment. In a similar manner, breakthrough experiments showed that $Fe_2(dobdc)$ can separate an equimolar mixture of ethylene and ethane into the pure component gases of 99% and 99.5% purity.

Although breakthrough experiments are quite valuable for evaluating the gas separation capabilities of a material, in practice they can be difficult and time consuming. In order to compare $Fe_2(dobdc)$ with other reported adsorbents for ethylene/ethane and propylene/propane separations, we sought to demonstrate that the breakthrough characteristics could instead be simulated with reasonable accuracy. Assuming that (i) intra-crystalline diffusion is negligible through an isothermal adsorption bed in thermodynamic equilibrium; (ii) plug flow proceeds through the bed; and (iii) the binary mixture adsorption equilibrium in the packed bed of crystallites can be calculated using LAST, we were able to solve a set of partial differential equiations and calculate breakthrough curves for both ethylene/ethane and propylene/propane mixtures. The resulting transient gas composition profiles (see FIG. 16 and FIG. 17) are in excellent agreement with the experimental results shown in FIG. 32 and FIG. 33.

Figure 34:
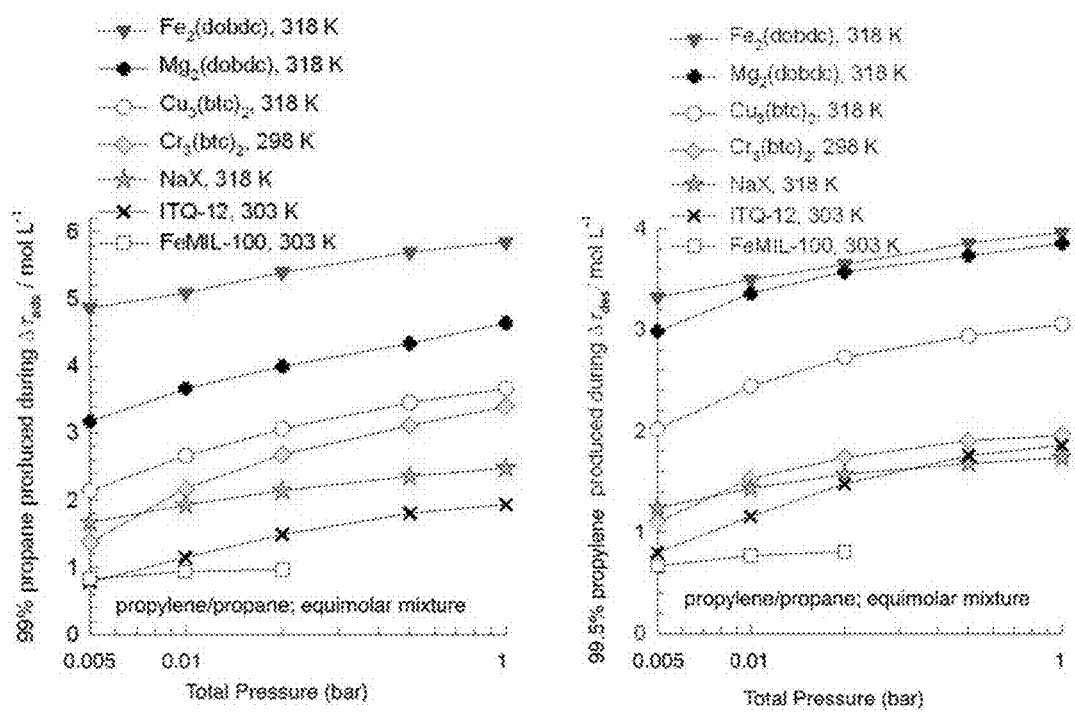
FIG. 34 is a series of graphs showing production capacities of 99% pure propane (left) and 99.5% pure propylene (right) as a function of the total pressure at the inlet to the adsorber for $Fe_2(dobdc)$, $Mg_2(dobdc)$, NaX zeolite, $Cu_3(btc)_2$, $Cr_3(btc)_2$, ITQ-12, and Fe-MIL-100.

Given this validation, analogous simulations were employed to make quantitative comparisons with other materials. From the simulated breakthrough curves, the time interval during which the exit gas compositions have a purity of 99% propane can be determined, together with the amount of 99% pure propane produced in this time interval. The production capacities, expressed as the amount of propane produced per liter of adsorbent are shown in FIG. 34 over a range of pressures for the zeolites ITQ-12 at 303 K and NaX at 318 K, and for the metal-organic frameworks $Cu_3(btc)_2$ ($btc^{3-}$=1,3,5-benzenetricarboxylate) at 318 K, $Cr_3$ $(btc)_2$ at 298 K, and Fe-MIL-100 at 303 K. FIG. 34 (left) is production capacity of 99% pure propane, expressed as mol propane produced per L adsorbent material, as a function of the total pressure at the inlet to the adsorber. The separation characteristics of $Fe_2(dobdc)$ at 318 K are compared to that of $Mg_2(dobdc)$ (318 K), NaX zeolite (318 K), $Cu_3(btc)_2$ (318 K), $Cr_3(btc)_2$ (298 K), ITQ-12 (303 K), and Fe-MIL-100 (303 K). (Right) is the production capacity of 99.5% pure propylene, expressed as mol propane produced per L adsorbent material, as a function of the total pressure at the inlet to the adsorber. These results indicate that the propane production capacity of $Fe_2(dobdc)$ at 318 K, which ranges up to 5.8 mol/L at a total pressure of 1.0 bar, is at least 20% higher than that of any of these other materials. A similar method was used to calculate the amount of polymer-grade (99.5%+) propylene that can be produced by these materials, again leading to a higher capacity for $Fe_2(dobdc)$ than for any other material. The compound $Mg_2(dobdc)$ exhibits a lower productivity than $Fe_2(dobdc)$, a result of the lower adsorption selectivity of this material. Although zeolite ITQ-12 displayed a comparable selectivity to $Fe_2(dobdc)$, its capacity limitation, which stems from its low pore volume of 0.134 $cm^3/g$, results in a propylene productivity that is just 47% of that of the metal-organic framework.

For the separation of ethylene/ethane mixtures, the breakthrough simulations indicate an even greater advantage of $Fe_2(dobdc)$ over other adsorbents, with production capacities that are roughly double those of $Mg_2(dobdc)$ and zeolite NaX (see FIG. 35). FIG. 35 is production capacities of 99% pure ethane (left), and 99.5% pure ethylene (right), expressed as mol produced per L adsorbent material, as a function of the total pressure at the inlet to the adsorber. The separation characteristics of $Fe_2(dobdc)$ at 318 K are compared to that of $Mg_2(dobdc)$ (318 K), and NaX zeolite at temperatures of 298 K, and 323 K.

Figure 36:
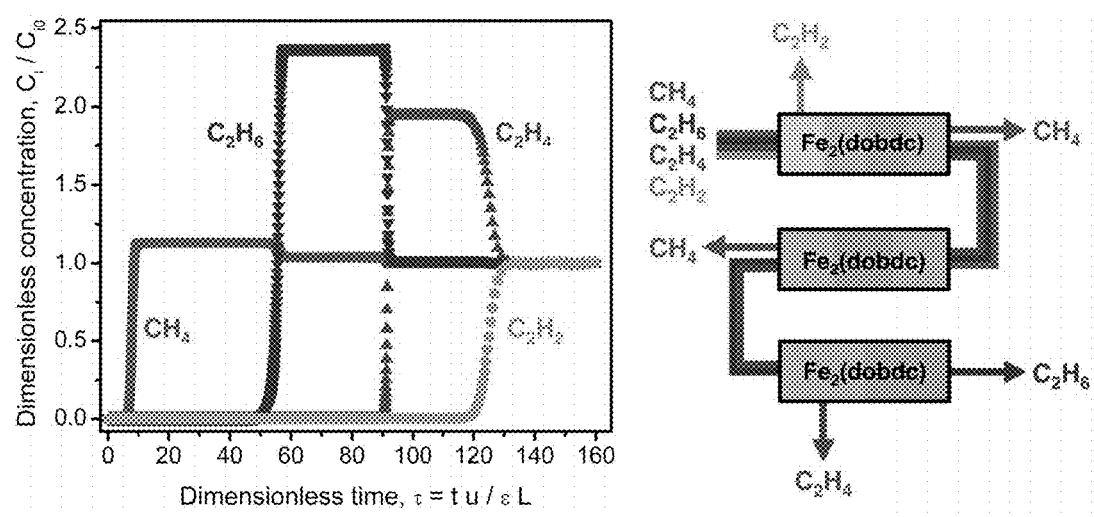
FIG. 36 shows, at left, a graph of calculated methane, ethane, ethylene, and acetylene breakthrough curves for various gases in $Fe_2(dobdc)$, and, at right, a schematic representation of the separation of a mixture of methane, ethane, ethylene, and acetylene using $Fe_2(dobdc)$ in an adsorption process.

In order to establish the feasibility of using $Fe_2(dobdc)$ for the task of selectively separating methane from mixtures including $C_2$ hydrocarbons (ethane, ethylene, and acetylene), breakthrough calculations were carried out for the mixture. The graph on the left of FIG. 36 shows calculated methane, ethane, ethylene, and acetylene breakthrough curves for an equimolar mixture of the gases at 1 bar flowing through a fixed bed of $Fe_2(dobdc)$ at 318 K. FIG. 36 presents simulated data on the gas phase molar concentrations exiting an adsorber packed with $Fe_2(dobdc)$ and subjected to a feed gas consisting of an equimolar mixture of methane, ethane, ethylene, and acetylene at a total pressure of 1 bar and a temperature of 318 K. Note that the breakthrough times reflect the relative adsorption selectivities (acetylene>ethylene>ethane>methane) for the material, and that the curves indicate a clean, sharp breakthrough transition for each successive gas.

Based on these results, the diagram at the right in FIG. 36 demonstrates how it might be possible to procure pure methane, ethane, ethylene, and acetylene using three packed beds of $Fe_2(dobdc)$. The diagram on the right in FIG. 36 shows a schematic representation of the separation of a mixture of methane, ethane, ethylene, and acetylene using just three packed beds of $Fe_2(dobdc)$ in a vacuum swing adsorption or temperature swing adsorption process. In this process, a gas mixture is fed into the first bed and methane, the fraction with the lowest adsorptivity, breaks through first. Pure methane can be collected until the second gas, ethane, breaks through. When the third component of the gas stream, ethylene is present in the eluent, the gas flow is diverted to a second bed, from which additional pure methane is collected during the adsorption step, and from which a mixture of ethane and ethylene is subsequently desorbed. This ethane/ethylene mixture is then separated into its pure components using a third adsorbent bed. By halting the feed into the first bed just prior to breakthrough of acetylene, pure acetylene can be obtained via desorption.

Figure 37:
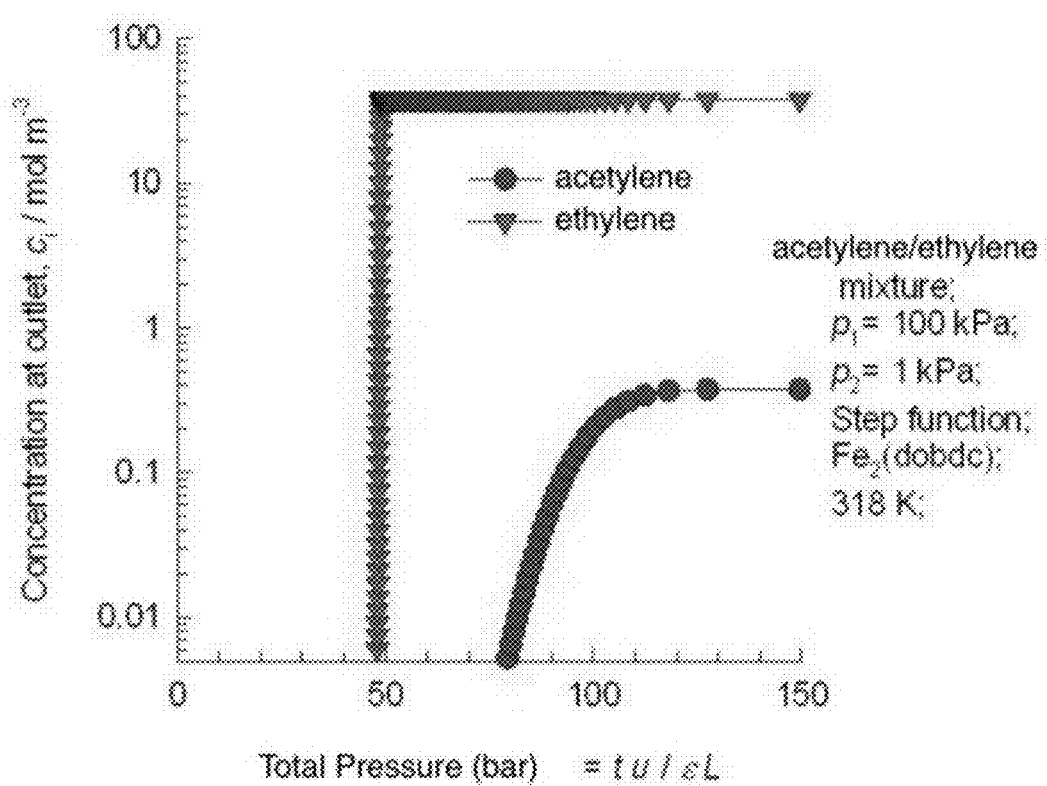
FIG. 37 shows transient breakthrough of acetylene/ethylene mixture in an adsorber bed packed with $Fe_2(dobdc)$.

The use of $Fe_2(dobdc)$ for removal of acetylene from mixtures with ethylene was investigated. FIG. 37 is transient breakthrough of acetylene/ethylene mixture in an adsorber bed packed with $Fe_2(dobdc)$. The inlet gas is maintained at partial presses $p_1$=100 kPa, $p_2$=1 kPa, at a temperature of 318 K. Simulated breakthrough characteristics for a feed mixture containing 1 bar of ethylene and 0.01 bar of acetylene at 318 K indicate that final acetylene concentrations on the order of 10 ppm could be realized (see FIG. 37).

Figure 41:
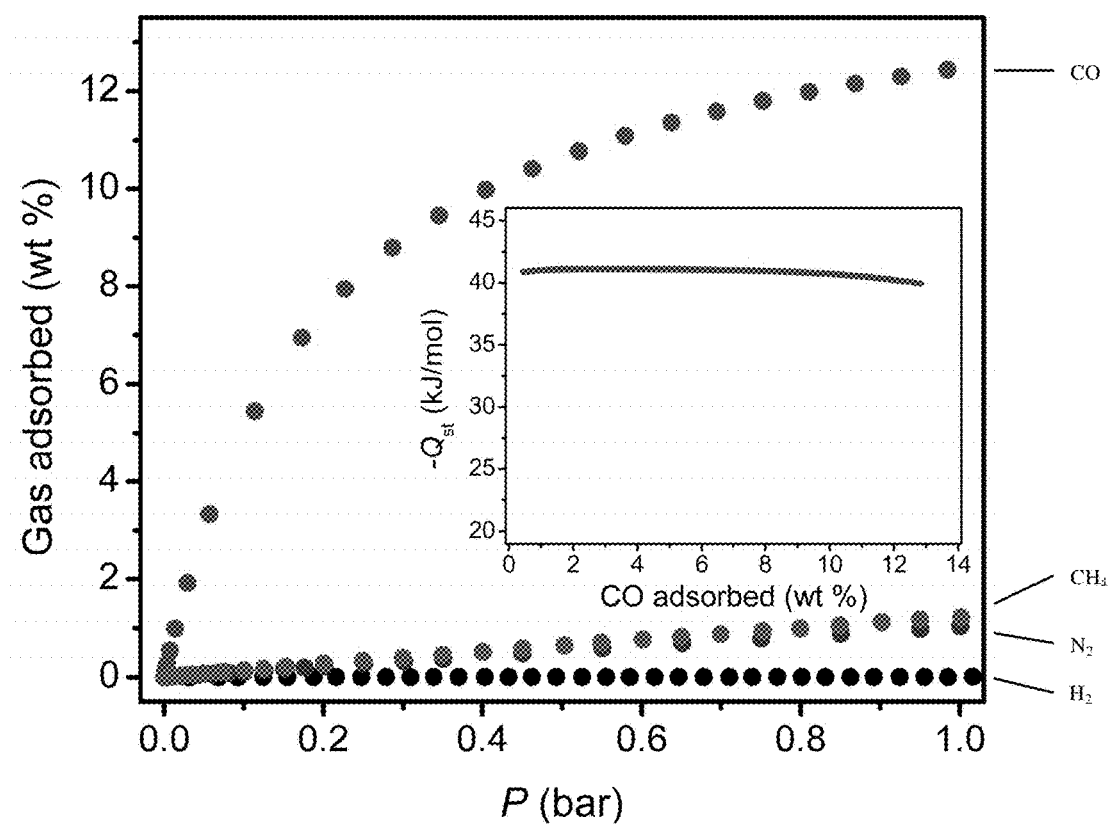
FIG. 41 shows the excess adsorption isotherms of CO, $CH_4$, $N_2$, and $H_2$ collected for $Fe_2(dobdc)$ at 318 K, and shows (inset) the isosteric heat of CO adsorption in $Fe_2$(dobdc) as a function of loading.

$Fe_2$(dobdc) can also be used for carbon monoxide separation. Fe2(dobdc) for the selective adsorption of carbon monoxide from $H_2$, $N_2$, and $CH_4$ was investigated. FIG. 41 shows the Excess adsorption isotherms of CO, $CH_4$, $N_2$, and $H_2$ collected for $Fe_2$(dobdc) at 318 K. Isosteric heat of CO adsorption in $Fe_2$(dobdc) as a function of loading. (inset). Single-component equilibrium adsorption isotherms collected on a sample of $Fe_2$(dobdc) at 318 K (FIG. 41) indicate significantly higher uptake of CO than $N_2$, $H_2$, or $CH_4$ over the entire pressure range measured. The CO isotherm displays a steep rise at low pressure and saturates over 12 wt % at 1 bar, while the other gases measured remain below 1.3 wt % at this pressure. Accordingly, the isosteric heat of CO adsorption (41 kJ/mol) as calculated from fits to isotherms collected at multiple temperatures is significantly higher than $N_2$, $H_2$, and $CH_4$ (35, 10.1, 20 kJ/mol, respectively). The high adsorption enthalpy of carbon monoxide to the $Fe^{2+}$ centers in $Fe_2$(dobdc) as compared to $N_2$, $CH_4$, and $H_2$ indicate that this material may be used for the adsorptive separation of these gases.

Figure 38:
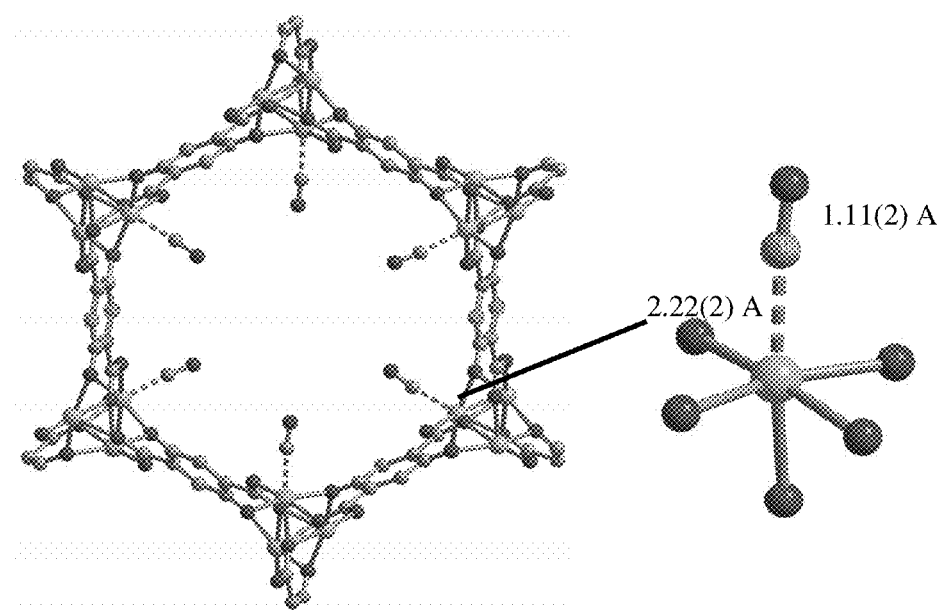
FIG. 38 is a graphical representation of a portion of the structure of $Fe_2(dobdc)$ showing carbon monoxide (CO) coordinated to the open $Fe^{2+}$ site.
Figure 39:
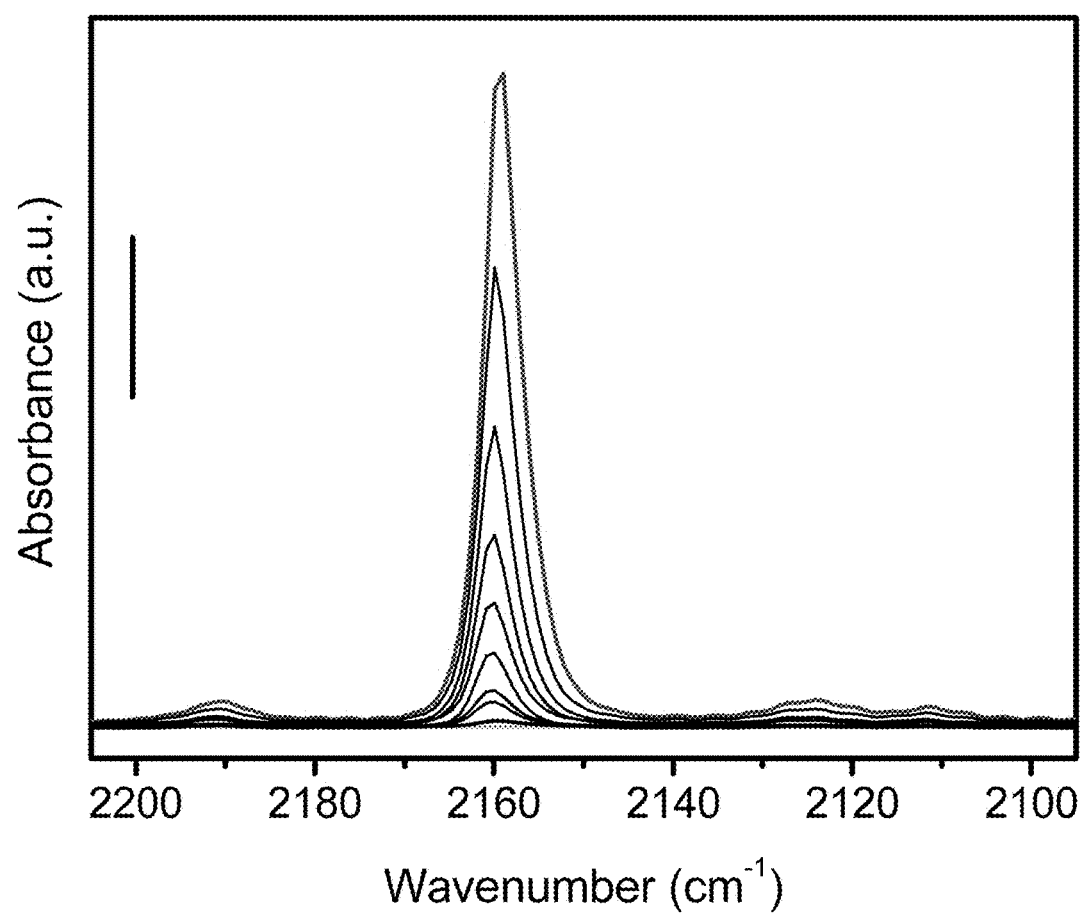
FIG. 39 is an infrared spectrum of $Fe_2(dobdc)$ under successively increasing doses of CO.
Figure 40:
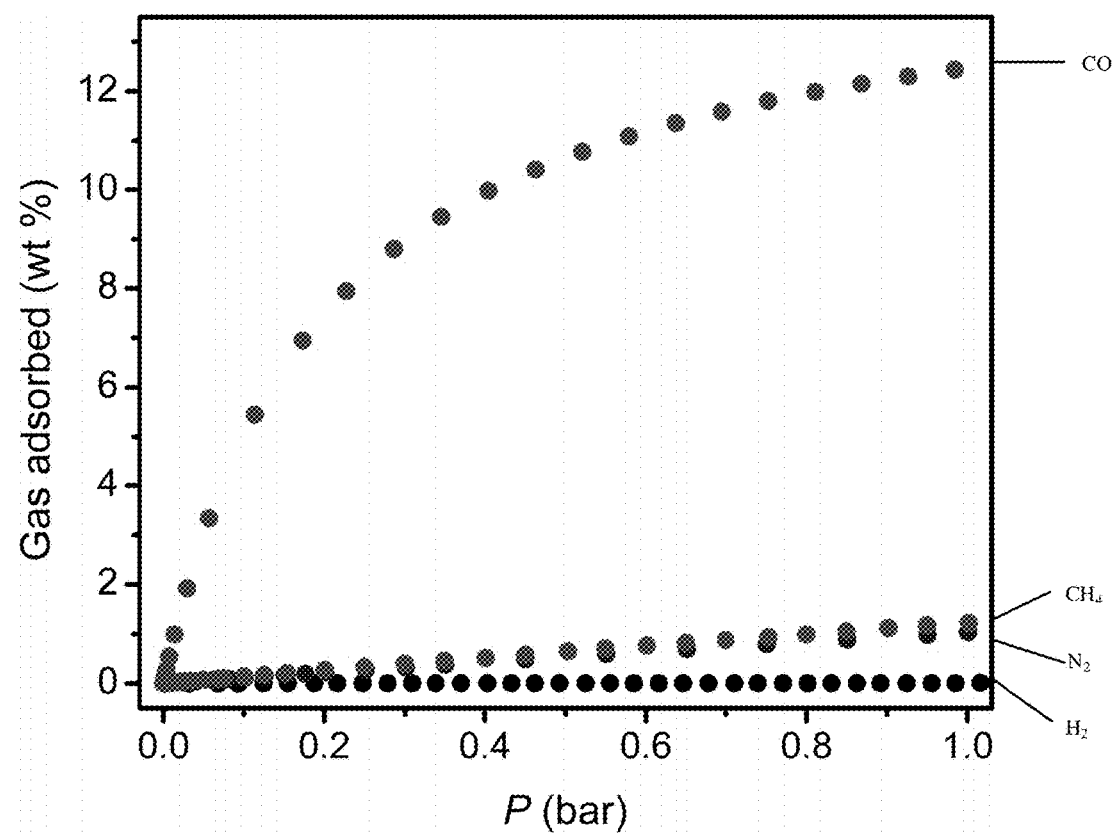
FIG. 40 is graph of low-pressure adsorption of CO, $CH_4$, $N_2$, and $H_2$ in $Fe_2(dobdc)$ at 298 K.

FIG. 38 is a portion of the structure of $Fe_2$(dobdc) showing carbon monoxide (CO) coordinated to the open $Fe^{2+}$ site. FIG. 39 is an infrared spectrum of $Fe_2$(dobdc) under successively increasing doses of CO. FIG. 40 is low-pressure adsorption of CO, $CH_4$, $N_2$, and $H_2$ in $Fe_2$(dobdc) at 298 K.

Figure 42:
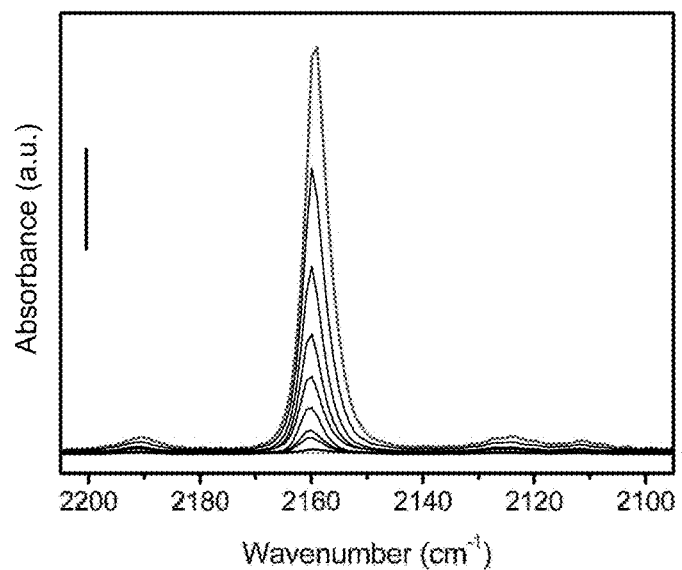
FIG. 42 show the infrared spectrum of CO adsorbed on $Fe_2(dobdc)$ at room temperature.

Infrared spectroscopy was used to investigate the nature of the interaction between the iron cations in $Fe_2$(dobdc) and adsorbed carbon monoxide. FIG. 42 show the Infrared spectrum of CO adsorbed on $Fe_2$(dobdc) at room temperature. Although infrared spectra for metal-organic frameworks of this structure type have a large number of vibrations at lower frequency, the pertinent region for metal carbonyl stretches is unobscured. Indeed, upon dosing an activated framework sample with CO at room temperature a clear band is evident at 2160 $cm^{-1}$. With higher CO loading this band intensifies and shifts slightly to 2159 $cm^{-1}$. At high coverage a number of additional bands appear at 2110, 2125, and 2190 $cm^{-1}$. The CO band at 2159 $cm^{-1}$ is assigned to the iron-bound carbonyl species, near the shift that has been previously reported for CO bound to the metal cation centers in $Mg_2$(dobdc) and $Ni_2$(dobdc). While the IR bands seen for these three materials are all blue-shifted relative to the IR stretch of gas phase CO (2143 $cm^{-1}$), the shift seen for $Fe_2$(dobdc) is red-shifted considerably compared to the Mg and Ni materials. This is likely attributed to the back-bonding from the $Fe^{2+}$ to the $2\pi^*$ antibonding orbital of CO weakening the C—O bond as compared to CO bound to $Mg_2$(dobdc) and $Ni_2$(dobdc).

Figure 43:
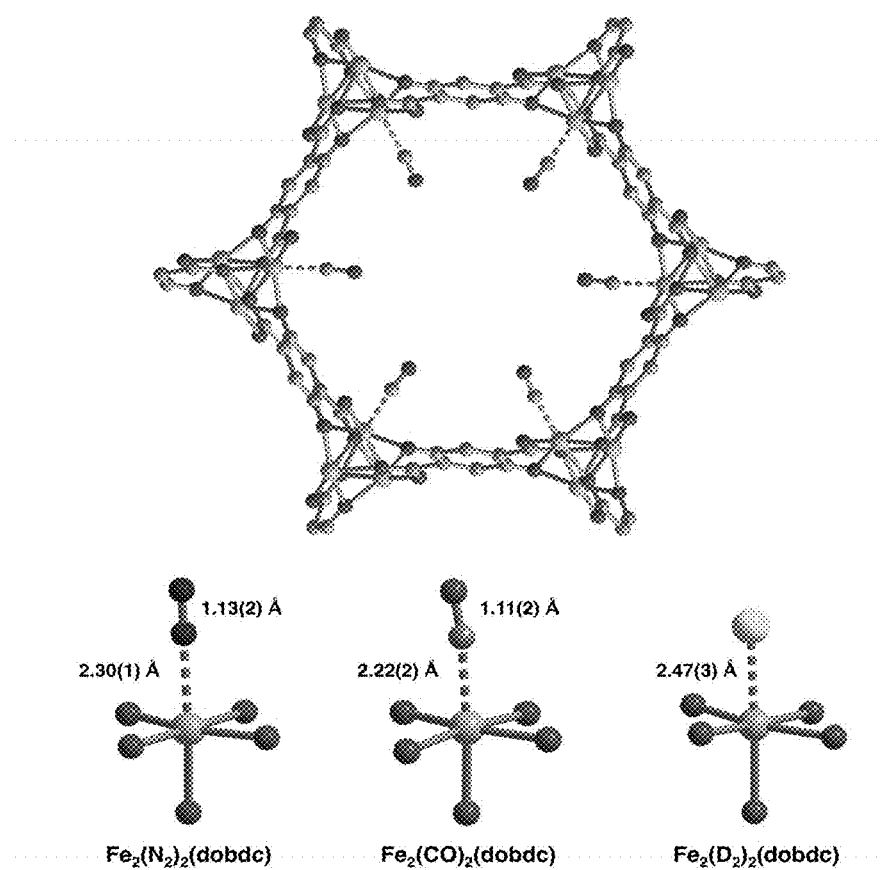
FIG. 43 is a graphical representation of crystal structures of $Fe_2(dobdc)$ with adsorbed $N_2$, CO, or $D_2$.

Powder neutron diffraction experiments were also carried out to crystallographically characterize (Fe—CO)$_2$(dobdc). Desolvated $Fe_2$(dobdc) was dosed with 0.75, and subsequently 1.5, equivalents of CO (per $Fe^{2+}$) at 300 K and cooled to 4 K for data collection. FIG. 43 show Crystal structures of $Fe_2$(dobdc) with adsorbed $N_2$, CO, or $D_2$. Carbon, iron, oxygen, nitrogen, and deuterium atoms are shown. At sub-stoichiometric CO loadings only one adsorption site is apparent, with an occupancy of 0.84(1). Consistent with infrared spectroscopy and gas adsorption experiments the strongest binding site is the unsaturated iron cation center. Carbon monoxide binds to the iron center end on at a Fe—C distance of 2.22(2) Å. The C—O distance for this complex of 1.11(2) is slightly shorter than that of free CO (1.127) consistent with the corresponding blue shift seen via IR. CO forms a nearly linear adduct with a Fe—C—O angle of 172.6(1)°. At the higher CO loading of 1.5 per $Fe^{2+}$ the first binding site saturates at an occupancy of 0.96(2) and a second site is apparent in which CO is parallel to the pore wall at a distance of 3.3-3.6 Å and an occupancy of 0.44(2).

Finally, given its clear ability to activate $O_2$, $Fe_2$(dobdc) can be employed as a catalyst for the oxidation of hydrocarbons. For example, $Fe_2$(dobdc) reacts rapidly in air to produce either $Fe_2(O_2)_2$(dobdc) (low temperature) or $Fe_2(O_2)$(dobdc) (room temperature) both of which contain reactive oxygen, either as superoxide in the former or peroxide in the latter. The large pore volume, high surface areas, accessible metal centers, and thermally stable nature of both of these resulting materials make them very promising oxidation catalysts. Although work with a number of systems, including the oxidation of methane to methanol and the oxidation of ethane/ethane and propane/propene. A representative reaction is shown in FIG. 49.

$Fe_2$(dobdc) catalyzes the oxidation of propylene to acetone with air as the oxidant. Although the yield of the reaction under current conditions is low the selectivity is approximately 100%. Examples of other reactions that may be chaptalized are shown below in FIG. 50.

Liquid-phase Hydrocarbon Oxidation Using $Fe_2$ (dobdc). In molecular Fe-oxo chemistry, N-oxides, peroxides, and hypervalent iodine-based O-atom transfer reagents are often used as sacrificial oxidants to generate the reactive Fe species from initial $Fe^{II}$ complexes. $Fe_2$(dobdc) was examined for liquid-phase C—H activation studies involving O-atom transfer reagents. While only limited reactivity was observed using pyridine-N-oxide and iodosylbenzene, upon addition of a solution of 2-(tert-butylsulfonyl)iodosylbenzene (tBuSO$_2$PhIO) (5 equiv.) and excess 1,4-cyclohexadiene (1,4-CHD) (24 equiv.) in $CD_3CN$ to the acetonitrile-solvated framework production of benzene (70% conversion based on iodosylarene) was observed (FIG. 1). A control experiment in which no metal-organic framework was added led to less than 3% benzene conversion. In addition, preliminary reactivity studies show that the framework is also capable of facilitating the room temperature conversion of toluene to benzyl alcohol/benzaldehyde and cyclohexane to cyclohexanol/cyclohexanone, albeit in low yields (<10% and <3%, respectively) with modest alcohol:ketone selectivities (3.5:1 and 4:1, respectively). Despite low yields and selectivities, these preliminary experiments provide indirect evidence that the oxidized iron framework is a strong oxidant, capable of functionalizing even the C—H bonds of cyclohexane (BDE=99.3 kcal/mol).

Gas-phase Oxidation of $Fe_2$(dobdc). Using a fully desolvated framework and a gaseous oxidizing agent without C—H bonds would circumvent any possible side-reactions such as H-atom abstraction. For this reason, we examined the gas phase oxidation of $Fe_2$(dobdc) with oxidants such as $N_2O$ or $O_2$. The reactivity of $Fe_2$(dobdc) sample oxidized with a gas phase oxidant was probed using 1,4-CHD. After addition of neat, excess 1,4-CHD, the framework gradually changed color from dark red brown to light yellow (similar in color to the methanol-solvated framework). Benzene was formed in 40% yield, demonstrating that the framework is capable of C—H activation.

Figure 44:
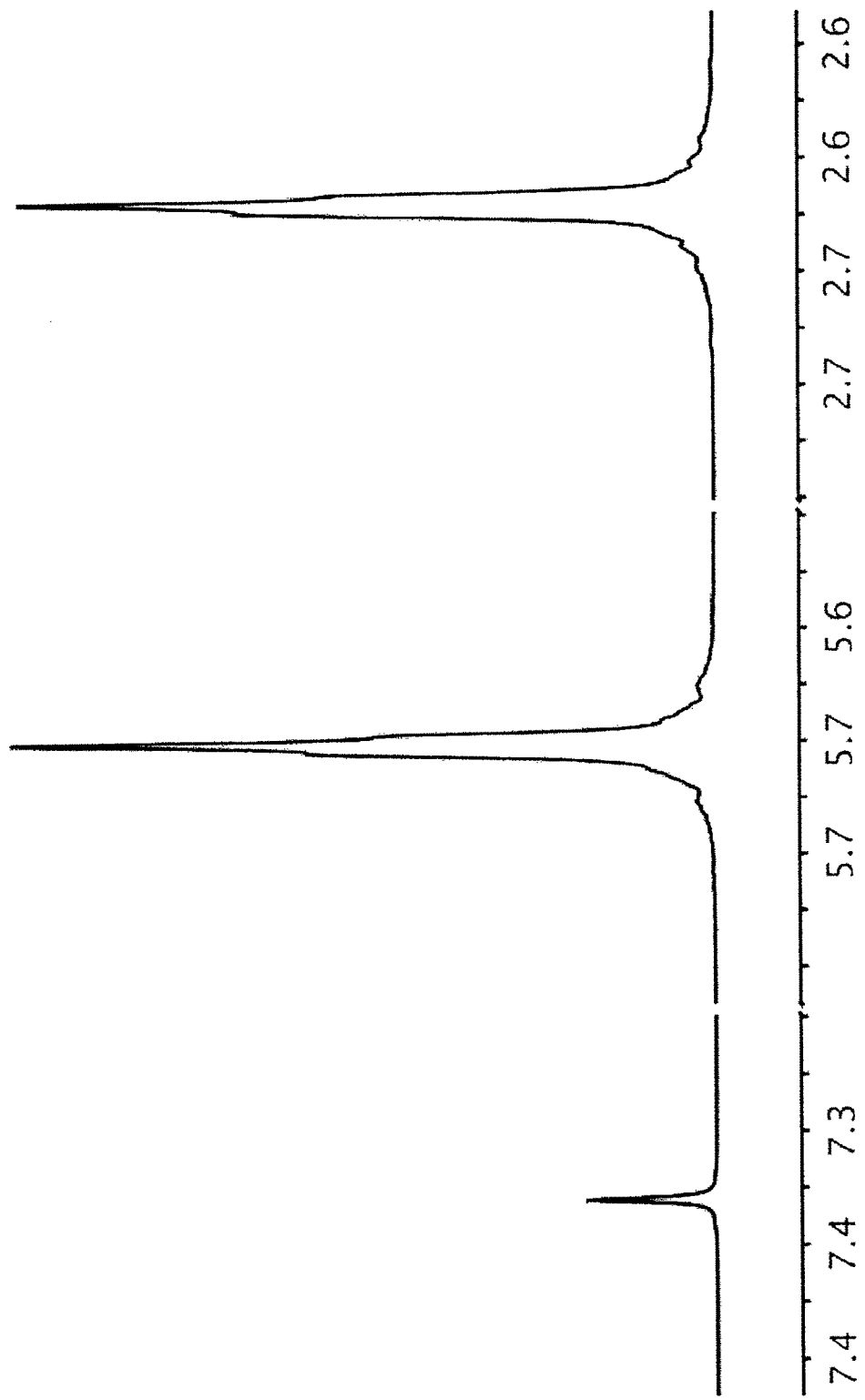
FIG. 44 is an $^1H$ NMR of products of the reaction of $Fe_2(dobdc)$ with excess 1,4-cyclohexadiene in $CD_3CN$.

Catalytic Oxidation of 1,4-Cyclohexadiene by $Fe_2$ (dobdc). $Fe_2$(dobdc) was added to a stirring solution of excess 1,4-cyclohexadiene and 2-(tert-butylsulfonyl)iodosylbenzene in $CD_3CN$. 1,2,4,5-tetramethylbenzene was added as an internal standard. The reaction mixture was stirred overnight at room temperature, filtered, and washed with 1 mL of $CD_3CN$. Reduction of the iodosylarene to 2-(tert-butylsulfonyl)iodobenzene (quantitative) and formation of benzene (70% yield, assuming 1 equiv of iodosylarene consumed leads to 1 equiv of benzene produced) was detected by $^1$H NMR. A $^1$H NMR of 1,4-cyclohexadiene was taken to quantify the amount of benzene in the starting material (1.3%). An identical control reaction run without Fe2(dobdc) was also performed, leading to ~3% conversion by $^1$H NMR. FIG. 44 shows the $^1$H NMR of products of the reaction of Fe$_2$(dobdc) with excess 1,4-cyclohexadiene in CD$_3$CN.

This application discloses several numerical ranges in the text and figures. The numerical ranges disclosed inherently support any range or value within the disclosed numerical ranges even though a precise range limitation is not stated verbatim in the specification because this invention can be practiced throughout the disclosed numerical ranges.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. Finally, the entire disclosure of the patents and publications referred in this application are hereby incorporated herein by reference.

REFERENCES

1. Ermsley, J. *Oxygen, Nature's Building Blocks: An A-Z Guide to the Elements*, Oxford University Press: Oxford, England, 2001
2. (a) Schütz, M.; Daun, M.; Weinspach, P.-M.; Drumbeck, M.; Hein, K. R. G. *Energy Convers. Manage.* 1992, 33, 357. (b) Descamps, C.; Bouallou, C.; Kannich, M. *Energy*, 2008, 33, 874.
3. (a) Hadjipaschalis, I.; Kourtis, G.; Poullikkas, A. *Renew. Sust. Energ. Rev.* 2009, 13, 2637. (b) Kather, A.; Scheffknecht, G. *Naturwissenschaften*, 2009, 96, 993.
4. Greenwood, N. N.; Earnshaw, A. *Chemistry of the Elements*, 2nd ed.; Butterworth Heinemann: Burlington, Mass., 2002; p 604,616.
5. Nandi, S. P.; Walker, P. L., Jr. *Sep. Sci. Technol.* 1976, 11, 441.
6. (a) Eddaoudi, M.; Kim, J.; Rosi, N.; Vodak, D.; Wachter, J.; O'Keeffe, M.; Yaghi, O. M. *Science* 2002, 295, 469. (b) Kitagawa, S.; Kitaura, R.; Noro, S.-I. *Angew. Chem., Int. Ed.* 2004, 43, 2334. (c) Matsuda, R.; Kitaura, R.; Kitagawa, S.; Kubota, Y.; Belosludov, R. V.; Kobayashi, T. C.; Sakamoto, H.; Chiba, T.; Takata, M.; Kawazoe, Y.; Mita, Y. *Nature* 2005, 436, 238. (d) Millward, A. R.; Yaghi, O. M. *J. Am. Chem. Soc.* 2005, 127, 17998. (e) Furukawa, H.; Miller, M. A.; Yaghi, O. M. *J. Mater. Chem.* 2007, 17, 3197. (f) Férey, G.; *Chem. Soc. Rev.*, 2008, 37, 191. (g) Ma, S.; Sun, D.; Simmons, J. M.; Collier, C. D.; Yuan, D.; Zhou, H.-C. *J. Am. Chem. Soc.*, 2008, 130, 1012. (h) Morris, R. E.; Wheatley, P. S. *Angew. Chem., Int. Ed.* 2008, 47, 4966. (i) Llewellyn, P. L.; Bourrelly, S.; Serre, C.; Vimont, A.; Daturi, M.; Hamon, L.; De Weireld, G.; Chang, J.-S.; Hong, D.-Y.; Hwang, Y. K.; Jhung, S. H.; Férey, G. *Langmuir* 2008, 24, 7245. (j) Murray, L. J.; Dincă, M.; Long, J. R. *Chem. Soc. Rev.* 2009, 38, 1294. (k) Chen, B.; Xiang, S.; Qian, G. *Acc. Chem. Res.* 2010, 1115.
7. (a) Hayashi, H.; Côté, A. P.; Furukawa, H.; O'Keeffe, M.; Yaghi, O. M. *Nat. Mater.* 2007, 6, 501. (b) Britt, D.; Tranchemontagne, D. J.; Yaghi, O. M. *Proc. Natl. Acad. Sci. U.S.A.* 2008, 105, 11623. (c) Britt, D.; Furukawa, H.; Wang, B.; Glover, T. G.; Yaghi, O. M. *Proc. Natl. Acad. Sci. U.S.A.* 2009, 106, 20637. (d) Li, J.-R.; Kuppler, R. J.; Zhou, H.-C.; *Chem. Soc. Rev.* 2009, 38, 1477.
8. (a) Mulfort, K. L.; Hupp, J. T. *J. Am. Chem. Soc.* 2007, 129, 9604. (b) Ingleson, M. J.; Perez Barrio, J.; Guilbaud, J. B.; Khimyak, Y. Z.; Rosseinsky, M. J. *Chem. Commun.* 2008, 2680. (c) Doonan, C. J.; Morris, W.; Furukawa, H.; Yaghi, O. M. *J. Am. Chem. Soc.* 2009, 131, 9492. (d) Tanabe, K. K.; Cohen, S. M. *Angew. Chem., Int. Ed.* 2009, 48, 7424.
9. (a) Seo, J. S.; Whang, D.; Lee, H.; Jun, S. I.; Oh, J.; Jeon, Y. J.; Kim, K. *Nature* 2000, 404, 982. (b) Wu, C.-D.; Hu, A.; Zhang, L.; Lin, W. *J. Am. Chem. Soc.* 2005, 127, 8940. (c) Bloch, E. D.; Britt, D.; Lee, C.; Doonan, C. J.; Uribe-Romo, F. J.; Furukawa, H.; Long, J. R.; Yaghi, O. M. *J. Am, Chem, Soc.* 2010, 132, 14382. (d) Chavan, S.; Vitillo, J. G.; Uddin, M. J.; Bonino, F.; Lamberti, C.; Groppo, E.; Lillerud, K-P.; Bordiga, S. *Chem. Mater.* 2010, 22, 4602.
10. (a) Rosi, N. L.; Kim, J.; Eddaoudi, M.; Chen, B. L.; O'Keeffe, M.; Yaghi, O. M. *J. Am. Chem. Soc.* 2005, 127, 1504. (b) Dietzel, P. D. C.; Morita, Y.; Blom, R.; Fjellvag, H. *Angew. Chem., Int. Ed.* 2005, 44, 6354. (c) Dietzel, P. D. C.; Panella, B.; Hirscher, M.; Blom, R.; Fjellvag, H. *Chem. Commun.* 2006, 959. (d) Caskey, S. R.; Wong-Foy, A. G.; Matzger, A. J. *J. Am. Chem. Soc.* 2008, 130, 10870. (e) Zhou, W.; Wu, J.; Yildirim, T. *J. Am. Chem. Soc.* 2008, 130, 15268. (f) Dietzel, P. D. C.; Johnson, R. E.; Blom, R.; Fjellvag, H. *Chem. Eur. J.* 2008, 14, 2389. (g) Dietzel, P. D. C.; Blom, R.; Fjellvag, H. *Eur. J. Inorg. Chem.* 2008, 3624. (h) Bhattacharjee, S.; Choi, J.; Yang, S.; Choi, S. B.; Kim, J.; Ahn, W. *J. Nanosci. Nanotechnol.* 2010, 10, 135. (i) Lamberti, C.; Zecchina, A.; Groppo, E.; Bordiga, S. *Chem. Soc. Rev.* 2010, 39, 4951. (j) Valenzano, L; Civalleri, B; Chavan, S.; Palomino, G. T.; Areán, C. O.; Bordiga, S. *J. Phys. Chem. C.* 2010, 114, 11185.
11. (a) Chui, S. S. Y.; Lo, S. M. F.; Charmant, J. P.-H.; Orpen, A. G.; Williams, I. D. *Science* 1999, 283, 1148. (b) Kramer, M.; Schwarz, U.; Kaskel, S. *J. Mater. Chem.* 2006, 16, 2245. (c) Murray, L. J.; Dincă, M.; Yano, J.; Chavan, S.; Bordiga, S.; Brown, C. M.; Long, J. R. *J. Am. Chem. Soc.* 2010, 132, 7856.
12. (a) Feig, A. L.; Lippard, S. J. *Chem. Rev.* 1994, 94, 759. (b) Que, L.; Dong, Y. *Acc. Chem. Res.* 1996, 29, 190. (c) Sono, M.; Roach, M. P.; Coulter, E. D.; Dawson, J. H. *Chem. Rev.* 1996, 96, 2841. (d) Kovaleva, E. G.; Neibegall, M. B.; Chakrabarty, S.; Lipscomb, J. D. *Acc. Chem. Res.* 2007, 40, 475.
13. Liss, K.-D.; Hunter, B. A.; Hagen, M. E.; Noakes, T. J.; Kennedy, S. J. *Physica B.* 2006, 385-386, 1010.
14. (a) Toby, B. H., EXPGUI, a graphical user interface for GSAS, J. Appl. Cryst. 2001, 34, 210.
(b) Larson, A. C.; Von Dreele R. B. "General Structure Analysis System (GSAS)", Los Alamos National Laboratory Report LAUR, 1994, 86-748.
15. (a) Halder, G. J.; Chapman, K. W.; Neville, S. M.; Moubaraki, B.; Murray, K. S.; Létard, J.-F.; Kepert, C. J. *J. Am. Chem. Soc.* 2008, 130, 17552. (b) Ma, S.; Yuan, D.; Chang, J.-S.; Zhou, H.-C. *Inorg. Chem.* 2009, 48, 5398. (c) Sumida, K.; Horike, S.; Kaye, S. S.; Herm, Z. R.; Queen, W. L.; Brown, C. M.; Grandjean, F.; Long, G. J.; Dailly, A.; Long, J. R. *Chem. Sci.* 2010, 1, 184. (d) Nayak, S.; Harms, K.; Dehnen, S. *Inorg. Chem.* 2010, 50, 2714.

16. Dietzel, P. D. C.; Georgiev, P. A.; Eckert, J.; Blom, R.; Strässle, T.; Unruh, T. *Chem. Commun.* 2010, 46, 1962.
17. Figgis, B. N. *Introduction to Ligand Fields*, John Wiley & Sons Inc. 1967.
18. Sherman, D. M. *American Mineralogist* 1985, 70, 1262.
19. (a) Li, Y.; Yang, R. T. *Langmuir* 2007, 23, 12937. (b) Maji, T. K.; Matsuda, R.; Kitagawa, S. *Nat. Mater.* 2007, 6, 142. (c) Yoon, J. W.; Jhung, S. H.; Hwang, Y. K.; Humphrey, S. M.; Wood, P. T.; Chang, J.-S. *Adv. Mater.* 2007, 19, 1830. (d) Mu, B.; Schoenecker, P. M.; Walton, K. S. *J. Phys. Chem. C* 2010, 114, 6464. (e) Xue, M.; Zhang, Z.; Xiang, S.; Jin, Z.; Liang, C.; Zhu, G.-S.; Qiu, S.-L.; Chen, B. *J. Mater. Chem.* 2010, 20, 3984. (f) Bae, Y.-S.; Spokoyny, A. M.; Farha, O. K.; Snurr, R. Q.; Hupp, J. T.; Mirkin, C. A. *Chem. Commun.* 2010, 46, 3478. (g) Southon, P. D.; Price, D. J.; Nielsen, P. K.; McKenzie, C. J.; Kepert, C. J. *J. Am. Chem. Soc.* 2011, 133, 10885.
20. Krishna, R.; Long, J. R. *J. Phys. Chem. C*, 2011, ASAP.
21. (a) Kumar, R. *Separ, Sci, Technol.* 1996, 31, 877. (b) Jee, J.-G.; Lee, J.-S.; Lee, C.-H. *Ind. Eng. Chem. Res.* 2001, 40, 3647. (c)
22. Ingalls, A. *Phys. Rev.* 1964, A133, 787.
23. (a) Shenoy, G. K.; Wagner, F. E.; Kalvius, G. M. *Mössbauer Isomer Shifts*, Shenoy, G. K. Wagner, F. E.; Eds., North-Holland, Amsterdam, 1978, 49. (b) Owen, T.; Grandjean, F.; Long, G. J.; Dornasevitch, K. V.; Gerasimchuk, N. *Inorg. Chem.* 2008, 47, 8704, and references given therein.
24. (a) Vaska, L. *Accounts of Chemical Research* 1976, 9, 175. (b) Watanabe, T.; Ama, T.; Nakamoto, K. *J. Phys Chem.* 1984, 88, 440-445. (c) Zecchina, A.; Scarano D.; Spoto. G. *J. Mol. Catal.* 1986, 38, 287-293. (d) Liu, J.; Ohta, T.; Yamaguchi, S.; Ogura, T.; Sakamoto, S.; Maeda, Y.; Naruta Y. *Angew. Chem. Int. Ed.* 2009, 48, 9262.
25. (a) Ahmad, S.; McCallum, J. D.; Shiemke, A. K.; Appelman, E. H.; Loehr, T. M.; Sanders-Loehr, *J. Inorg. Chem.* 1988, 27, 2230. (b) McCandlish, E., Miksztal, A. R.; Nappa, M.; Sprenger, A. Q.; Valentine, J. S.; Stong, J. D.; Spiro, T. G. *J. Am. Chem. Soc.* 1980, 102, 4268
26. Babcock, H. D.; Herzberg, L. *Astrophys. J.* 1948, 108, 167.
27. (a) Stromberg, R.; Ainalem, I.-B. *Acta. Chem. Scand.* 1968, 22, 1439. (b) Van Atta, R. B.; Strouse, C. E.; Hanson, L. K.; Valentine, J. S. *J. Am. Chem. Soc.* 1987, 109, 1425. (c) Egan, J. W.; Haggerty, B. S.; Rheingold, A. L.; Sendlinger, S. C.; Theopold, K. H. *J. Am. Chem. Soc.* 1990, 112, 2445. (d) Yao, S.; Bill, E.; Milsmann, C.; Wiegardt, K.; Driess, M. *Angew. Chem. Int. Ed.* 2008, 47, 7110. (e) Cho, J.; Sarangi, R.; Annaraj, J.; Kim, S. Y.; Ogura, T.; Solomon, E. I.; Nam. W. *Nat. Chem.* 2009, 1, 568. (f) Annaraj, J.; Cho, J.; Lee, Y.-M.; Kim, S. J.; Latifi, R.; Visser, S. P. de; Nam, W. *Angew. Chem. Int. Ed.* 2009, 48, 4150.
28. (a) Karlsson, A.; Parales, J. V.; Parales, R. E.; Gibson, D. T.; Eklund, H.; Ramaswamy, S. *Science* 2003, 299, 1039. (b) Kovaleva, E. G.; Libscomb, J. D. *Science* 2007, 316, 453.
29. (a) Roelfes, G.; Vrajmasu, V.; Chen, K.; Ho, R. Y. N.; Rohde, J.-U. Zondervan, C.; la Crois, R. M.; Schudde, E. P.; Lutz, M.; Spek, A. L.; Hage, R.; Fering a, B. L.; Munck, E.; Que, L. *Inorg. Chem.* 2003, 42, 2639. (b) Horner, O.; Mouesca, J.-M.; Oddou, J.-L.; Jeandey, C.; Nivière, V.; Mattioli, T. A.; Mathé, C.; Fontecave, M.; Maldivi, P.; Bonville, P.; Halven, J. A.; Latour, J.-M. *Biochemistry* 2004, 43, 8815.
30. Huber, K. P.; Herzber, G. *Molecular Spectra and Molecular Structure. IV. Constants of Diatomic Molecules*, Van Nostrand Reinhold: New York, 1979; p. 420.
31. Kovaleva, E. G.; Neibergall, M. B.; Chakrabarty, S.; Lipscomb, J. D. *Acc Chem. Rec.* 2007, 40, 475.

What is claimed:

1. A method of separating a mixture stream comprising a paraffin and an olefin comprising:
    contacting the mixture stream with $Fe_2(dobdc)$ (dobdc=2,5-dioxido-1,4-benzenedicarboxylate); and
    obtaining a first stream richer in the paraffin as compared to the mixture stream.

2. The method of claim 1, wherein the paraffin is ethane and the olefin is ethene.

3. The method of claim 1, wherein the paraffin is propane and the olefin is propene.

4. The method of claim 1, wherein the paraffin in the obtained first stream has a purity greater than 99.5 percent.

5. The method of claim 1, further comprising obtaining a second stream richer in the olefin as compared to the mixture stream.

6. The method of claim 1, wherein the temperature of the mixture stream when contacting with $Fe_2(dobdc)$(dobdc=2,5-dioxido-1,4-benzenedicarboxylate) is 318 to 353 K.

7. The method of claim 6, wherein the pressure of the mixture stream when contacting with $Fe_2(dobdc)$(dobdc=2,5-dioxido-1,4-benzenedicarboxylate) is equal to or less than 1 bar.

8. The method of claim 1, wherein the temperature of the mixture stream when contacting with $Fe_2(dobdc)$(dobdc=2,5-dioxido-1,4-benzenedicarboxylate) is 201 to 226 K.

9. The method of claim 5, wherein the olefin in the second stream has a purity greater than 99 percent.

* * * * *

UNITED STATES PATENT AND TRADEMARK OFFICE
CERTIFICATE OF CORRECTION

PATENT NO. : 9,675,923 B2
APPLICATION NO. : 13/593914
DATED : June 13, 2017
INVENTOR(S) : Jeffrey R. Long et al.

It is certified that error appears in the above-identified patent and that said Letters Patent is hereby corrected as shown below:

In the Drawings

Sheet 8 of 41, Fig. 9, Line 1, delete "composistion" and insert --composition--, therefor.

Sheet 9 of 41, Fig. 10, Line 1, delete "composistion" and insert --composition--, therefor.

In the Specification

At Column 4, Line number 47, delete "$Fe_2(O_2)_2(dobdc)\text{-}2O_2$" and insert --$Fe_2(O_2)_2(dobdc)\text{-}2O_2$--, therefor.

At Column 5, Line number 42, delete "shownig" and insert --showing--, therefor.

At Column 6, Line number 44, delete "disply" and insert --display--, therefor.

At Column 7, Line number 34, delete "$Fe_2Cl_2H_{18}O_{10}$:" and insert --$Fe_2C_{12}H_{18}O_{10}$:--, therefor.

At Column 7, Line number 48, delete "Oar/min." and insert --µbar/min.--, therefor.

At Column 7, Line number 53, delete "Oar/min." and insert --µbar/min.--, therefor.

At Column 7, Line number 67, delete "2-cm$^{-1}$" and insert --2 cm$^{-1}$--, therefor.

At Column 9, Line number 19, delete "Lorenzian" and insert --Lorentzian--, therefor.

At Column 10, Line number 23, delete "$Fe'''$" and insert --$Fe^{II}$--, therefor.

At Column 10, Line number 35, delete "$Fe'''$" and insert --$Fe^{II}$--, therefor.

At Column 10, Line number 40, delete "16000 cm$^-$" and insert --16000 cm$^{-1}$--, therefor.

Signed and Sealed this
Tenth Day of July, 2018

Andrei Iancu
*Director of the United States Patent and Trademark Office*

CERTIFICATE OF CORRECTION (continued)
U.S. Pat. No. 9,675,923 B2

At Column 10, Line numbers 45-46, delete "pseudooctahedral" and insert --pseudo octahedral--, therefor.

At Column 10, Line number 48, delete "preferrentially" and insert --preferentially--, therefor.

At Column 11, Line number 30, delete "(ILAST)" and insert --(IAST)--, therefor.

At Column 12, Line number 9, delete "alu" and insert --$\varepsilon L/u$--, therefor.

At Column 12, Line number 11, delete "r" and insert --$\tau$--, therefor.

At Column 14, Line number 12, delete "of this".

At Column 14, Line number 15, delete "Fe.O$_{linker}$" and insert --Fe-O$_{linker}$--, therefor.

At Column 17, Line number 44, delete "agains" and insert --against--, therefor.

At Column 18, Line number 37, delete "seletvities" and insert --selectivities--, therefor.

At Column 18, Line number 50, delete "LAST" and insert --IAST--, therefor.

At Column 19, Line numbers 9-10, delete "selectivites" and insert --selectivities--, therefor.

At Column 19, Line number 39, delete "LAST" and insert --IAST--, therefor.

At Column 19, Line number 40, delete "equiations" and insert --equations--, therefor.

At Column 21, Line number 60, delete "sub-stoichiometic" and insert --sub-stoichiometric--, therefor.

At Column 23, Line number 35, insert --.--.